United States Patent
Beard et al.

(10) Patent No.: US 10,800,744 B2
(45) Date of Patent: *Oct. 13, 2020

(54) IMIDAZOLE DERIVATIVES AS FORMYL PEPTIDE RECEPTOR MODULATORS

(71) Applicant: Allergan, Inc., Irvine, CA (US)

(72) Inventors: Richard L. Beard, Newport Beach, CA (US); Tien T. Duong, Rancho Santa Margarita, CA (US); Michael E. Garst, Newport Beach, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/419,317

(22) Filed: May 22, 2019

(65) Prior Publication Data
US 2020/0115346 A1 Apr. 16, 2020

Related U.S. Application Data

(63) Continuation of application No. 15/312,367, filed as application No. PCT/US2015/032069 on May 21, 2015, now Pat. No. 10,301,269.

(60) Provisional application No. 62/001,188, filed on May 21, 2014.

(51) Int. Cl.
*C07D 233/64* (2006.01)
*A61K 31/4172* (2006.01)
*A61K 31/4174* (2006.01)

(52) U.S. Cl.
CPC ........ *C07D 233/64* (2013.01); *A61K 31/4172* (2013.01); *A61K 31/4174* (2013.01)

(58) Field of Classification Search
CPC combination set(s) only.
See application file for complete search history.

(56) References Cited

U.S. PATENT DOCUMENTS

| | | |
|---|---|---|
| 8,440,684 B2 | 5/2013 | Beard |
| 8,492,556 B2 | 7/2013 | Beard et al. |
| 8,507,560 B2 | 8/2013 | Beard |
| 8,541,577 B2 | 9/2013 | Beard et al. |
| 8,580,817 B2 | 11/2013 | Beard |
| 8,658,803 B2 | 2/2014 | Beard et al. |
| 8,809,367 B2 | 8/2014 | Beard |
| 8,816,076 B2 | 8/2014 | Beard et al. |
| 8,993,780 B2 | 3/2015 | Beard et al. |
| 9,428,549 B2 | 8/2016 | Beard |
| 10,301,269 B2 | 5/2019 | Beard |
| 2013/0109866 A1 | 5/2013 | Beard et al. |
| 2013/0274230 A1 | 10/2013 | Beard et al. |
| 2014/0256684 A1 | 9/2014 | Beard |
| 2014/0256685 A1 | 9/2014 | Beard et al. |
| 2015/0291511 A1 | 10/2015 | Beard et al. |

FOREIGN PATENT DOCUMENTS

| | | |
|---|---|---|
| FR | 2533210 | 3/1984 |
| RU | 2386622 | 4/2010 |
| WO | 2005-047899 | 5/2005 |
| WO | 2005066145 | 7/2005 |
| WO | 200900748 | 1/2009 |
| WO | 2013-062947 | 5/2013 |
| WO | 2013-0122953 | 8/2013 |
| WO | 2015-077451 | 5/2015 |
| WO | 2015-116566 | 8/2015 |
| WO | 2015-116574 | 8/2015 |
| WO | 2017172761 | 10/2017 |
| WO | 2017180323 | 10/2017 |

OTHER PUBLICATIONS

Chemical Abstract Service STN Registry Database (online), Registry Nos. 1712499-08-5 and 1712499-09-6 [Entered STN: May 26, 2015]. (Year: 2015).*
1378482-06-4, 1378391-54-8, 1378385-01-3, ACS, STN Registry Database, published on Jun. 14, 2012, 1 page.
1378970-43-4, ACS, STN Registry Database, published on Jun. 15, 2012, 1 page.
1379170-34-9, ACS, STN Registry Database, published on Jun. 17, 2012, 1 page.
1423602-69-0, ACS, STN Registry Database, published on Mar. 14, 2013, 1 page.
1424349-94-9, ACS, STN Registry Database, published on Mar. 15, 2013, 1 page.
1428092-78-7, ACS, STN Registry Database, published on Apr. 11, 2013, 1 page.
1477542-70-3, ACS, STN Registry Database, published on Nov. 20, 2013, 1 page.
1479511-24-4, ACS, STN Registry Database, published on Nov. 24, 2013, 1 page.
1483807-63-1, ACS, STN Registry Database, published on Nov. 29, 2013, 1 page.
1491331-55-5, ACS, STN Registry Database, published on Dec. 10, 2013, 1 page.
1492584-16-3, ACS, STN Registry Database, published on Dec. 11, 2013, 1 page.
1496192-08-5, ACS, STN Registry Database, published on Dec. 16, 2013, 1 page.
1497615-40-3, ACS, STN Registry Database, published on Dec. 18, 2013, 1 page.
1549726-72-8, ACS, STN Registry Database, published on Feb. 19, 2014, 1 page.
Chiang, Nan, et al., The Lipoxin Receptor ALX: Potent Ligand-Specific and Stereoselective Actions in Vivo, Pharmacological Reviews, 2006, 463-487, 58, No. 3.
Cross et al, Rules for the Nomenclature of Organic Chemistry, Pure & Appli. Chem, 1976, 11-30, vol. 45.

(Continued)

*Primary Examiner* — Amanda L. Aguirre
(74) *Attorney, Agent, or Firm* — Jonathan Bass

(57) ABSTRACT

The present invention relates to imidazole derivatives, processes for preparing them, pharmaceutical compositions containing them and their use as pharmaceuticals as modulators of the N-formyl peptide receptor.

25 Claims, No Drawings

(56) References Cited

OTHER PUBLICATIONS

Database Chemcats [Online] Chemical Abstracts; Mar. 31, 2014; Selena Chemical Building Blocks: "1-[4-(aminophenyl)phenyl]-3-[(1-methyl-1H-imidazol-2-yl)methyl]urea", XP002743162, Database accession No. 1621638745.

Dianqing Sun and Richard E, Lee, Solid-Phase Synthesis of a Thymidinyl Dipeptide Urea Library, Journal of Combinatorial Chemistry, 2007, pp. 370-385, vol. 9.

Dufton, Neil et al., Anti-inflammatory Role of Murine Formyl-Peptide Receptor 2:Ligand-Specific Effects on Leukocyte Responses and Experimental Inflammation, The Journal of Immunology, Jan. 2010, pp. 2611-2619, 184, The American Association of Immunologist, Inc., Bethesda, MD.

Gavins, Felicity N., et al., Leukocyte recruitment in the brain in sepsis: involvement of the annexin 1-FPR2/ALX anti-inflammatory system, FASEB J., Sep. 10, 2012, 4977-4989, 26.

Gronert, Karsten, Lipoxins in the eye and their role in wound healing, Prostaglandins, Leukotrienes and Essential Fatty Acids, 2005, pp. 221-229, 73, Elsevier Ltd.

Gronert, Karston, et al., A Role for the Mouse 12/15-Lipoxygenase Pathway in Promoting Epithelial Wound Healing and Host Defense, The Journal of Biological Chemistry, 2005, pp. 15267-15278, 280, No. 15.

International Search Report & Written Opinion dated Sep. 9, 2015 for PCT/US15/32069 filed May 21, 2015 in the name of ALLERGAN, INC.

Leedom, Alexander J., et al., Endogenous LXA4 Circuits are Determinants of Pathological Angiogenesis in Response to Chronic Injury, The American Journal of Pathology, Jan. 2010, pp. 74-84, 176, No. 1, American Society for Investigative Pathology.

Leoni, Giovanna, et al., Annexin A1, formyl peptide receptor, and NOX1 orchestrate epithelial repair, The Journal of Clinical Investigation, 2013, 443-54, 123.

Maderna. Paola, et al., FPR2/ALX receptor expression and internalization are critical for lipoxin A4 and annexin-derived peptide-stimulated phagocytosis, FASEB J., Nov. 2010, 4240-4249, 24 (11).

Medeiros, Rodrigo, et al., Molecular Mechanisms of Topical Anti-Inflammatory Effects of Lipoxin A4 in Endotoxi-Induced Uveitis, Molecular Pharmacology, 2008, pp. 154-161, 74.

Moller, Marianne et al., Synthesis and Spectroscopic Characterization of 4-Chlorophenyl Isocyanate(= 1-chloro-4-isocyanatobenzene) Adducts with Amino Acids . . . , Helvetica Chimica Acta, 1998, 1254-1263, vol. 81.

Perretti, Mauro et al, Therapeutic Anti-Inflammatory Potential of Formyl-Peptide Receptor Agonists, Pharmacology & Research, 2010, 175-188, 127.

Reville, Keira, et al., Lipoxin A4 Redistributes Myosin IIA and Cdc42 in Macrophages: Implications for Phagocytosis of Apoptotic Leukocytes, The Journal of Immunology, 2006, pp. 1878-1888, 176.

Serhan, Charles N., Resolution Phase of Inflammation: Novel Endogenous Anti-Inflammatory and Proresolving Lipid Mediators and Pathways, The Annual Reviews of Immunology, 2007, pp. 101-37, 25, Annual reviews.

Stahl, Heinrich et al, Handbook of Pharmaceutical Salts, Verlag Helvetica Chimica Acta—Zurich, 2002, 329-345.

Takano, Tomoko, et al., Aspirin-triggered 15-Epi-Lipoxin-A4 (LXa4) and LXA4 Stable Analogues are Potent Inbitiors of Acute Inflammation: Evidence for Anti-inflammatory Receptors, Journal of Experimental Medicine, May 5, 1997, 1693-1704, 185, No. 9, The Rockerfeller University Press.

Tsuruki, Takahiro, et al., Mechanism of the Protective Effect of Intraperitoneally Administered Agonists for Formyl Peptide Receptors against Chemotherapy-Induced Alopecia, Bioscience, Biotechnology & Biochemistry, 2007, pp. 1198-1202, 71, No. 5.

Yamasaki, Kenshi et al., Increased serine protease activity arid cathelicidin promotes skin inflammation in rosacea, Nature Medicine, Aug. 2007, pp. 975-980, vol. 13, No. 8, Nature Publishing Group.

Yingyong Huaxue, Chinese Journal of Applied Chemistry, 1990, 1-9, 7.

Litvitskiy, P.F., Inflammation, Pathophysiology, 2003, 142-144 & 192-200, Ch. 5.

* cited by examiner

IMIDAZOLE DERIVATIVES AS FORMYL PEPTIDE RECEPTOR MODULATORS

CROSS-REFERENCE TO RELATED APPLICATIONS

This application is a continuation of U.S. patent application Ser. No. 15/312,367, filed on Nov. 18, 2016, which is a national stage application under 35 U.S.C. § 371 of PCT application PCT/US2015/032069, filed May 21, 2015, which claims the benefit of U.S. Provisional Patent Application No. 62/001,188, filed May 21, 2014, each of which are incorporated herein by reference in their entireties, and serve as the basis for a priority and/or benefit claim of the present application.

FIELD OF THE INVENTION

The present invention relates to imidazole derivatives, processes for preparing them, pharmaceutical compositions containing them, and their use as pharmaceuticals as modulators of the N-formyl peptide receptor (FPR), such as the N-formyl peptide receptor 2 (FPR2). The invention relates specifically to the use of these compounds and their pharmaceutical compositions to treat disorders associated with FPR 20 modulation, such as FPR2 modulation.

BACKGROUND OF THE INVENTION

The FPR family belongs to the seven transmembrane domain G-protein-coupled receptor (GPCR) family. This family includes three members in humans. One member of this family, FPR2 (also known as FPRL-1 or ALXA4), is expressed predominantly on inflammatory cells, such as monocytes and neutrophils, as well as on T cells, and has been shown to play a critical role in leukocyte trafficking during inflammation and human pathology (See Chiang N, Serhan C N, Dahlen, S, Drazen J M, Hay D W P, Rovati E, Shimizu T, Yokomizo T, Brink, C. The lipoxin receptor ALX: Potent ligand-specific and stereoselective actions in vivo. Pharmacological Reviews 2006; 58: 463-519).

FPR2 is an exceptionally promiscuous receptor that responds to a menagerie of structurally diverse exogenous and endogenous ligands, including serum amyloid A (SAA), chemokine variant sCKβ8-1, the neuroprotective peptide humanin, anti-inflammatory eicosanoid lipoxin A4 (LXA4) and glucocorticoid-modulated protein annexin A1 (Chiang N, Serhan C N, Dahlen, S, Drazen J M, Hay D W P, Rovati E, Shimizu T, Yokomizo T, Brink, C. The lipoxin receptor ALX: Potent ligand-specific and stereoselective actions in vivo. Pharmacological Reviews 2006; 58: 463-519).

FPR2 transduces anti-inflammatory effects of arachidonic acid derived LXA4 in many systems, and has been shown to play a key role in the resolution of inflammation (Dufton N, Perretti M. Therapeutic anti-inflammatory potential of formyl peptide receptor agonists. Pharmacology & Therapeutics 2010; 127: 175-188).

FPR2 knockout mice show exaggerated inflammation in disease conditions, as expected from the biological role of the receptor (See Dufton N, Hannon R, Brancaleone V, Dalli J, Patel H B, Gray M, D'Aquisto F, Buckingham J C, Perretti M, Flower R J. Anti-inflammatory role of the murine formyl-peptide receptor 2: Ligand-specific effects on leukocyte responses and experimental inflammation. Journal of Immunology 2010; 184: 2611-2619. Gavins F N E, Hughes E L, Buss N A P S, Holloway P M, Getting S J, Buckingham J C. Leukocyte recruitment in the brain in sepsis: involvement of the annexin1 FPR2/ALX anti-inflammatory system. FASEB 2012; 26: 1-13).

Activation of FPR2 by LXA4 or its analogs and by annexin I protein has been shown to result in anti-inflammatory activity by promoting active resolution of inflammation, which involves inhibition of polymorphonuclear neutrophils (PMNs) and eosinophils migration, and also stimulating monocyte migration, enabling clearance of apoptotic cells from the site of inflammation in a nonphlogistic manner (See Gavins F N E, Hughes E L, Buss N A P S, Holloway P M, Getting S J, Buckingham J C. Leukocyte recruitment in the brain in sepsis: involvement of the annexin1 FPR2/ALX anti-inflammatory system. FASEB 2012; 26: 1-13, Madema P, Cottell D C, Toivonen T, Dufton N, Dalli J, Perretti M, Godson C. FPR2/ALX receptor expression and internalization are critical for lipoxin A4 and annexin-derived peptide-stimulated phagocytosis. FASEB 2010; 24: 4240-4249).

In addition, FPR2 has been shown to inhibit natural killer (NK) cytotoxicity and promote activation of T cells, which further contributes to down regulation of tissue damaging inflammatory signals.

FPR2 interaction with LXA4 and annexin has been shown to be beneficial in experimental models of dermal inflammation, angiogenesis, epithelial migration, edema, alopecia, ischemia reperfusion and ocular inflammation, such as endotoxin-induced uveitis and comrneal wound healing (See Reville K, Cream J K, Vivers S, Dransfield I, Godson C. Lipoxin A4 redistributes Myosin IIA and Cdc42 in macrophages: Implications for phagocytosis of apoptotic leukocytes. Journal of Immunology 2006; 176: 1878-1888; Serhan C. Resolution phase of inflammation: Novel endogenous anti-inflammatory and proresolving lipid mediators and pathways. Annual reviews of Immunology 2007; 25: 101-137; Medeiros R, Rodrigues G B, Figueiredo C P, Rodrigues E B, Grumman A Jr, Menezes-de-Lima O Jr, Passos G F, Calixto J B. Molecular mechanisms of topical anti-inflammatory effects of lipoxin A(4) in endotoxin-induced uveitis. Molecular Pharmacology 2008; 74: 154-161; Gronert K, Maheshwari N, Khan N, Hassan I R, Dunn M, Schwartzmann M L. A role for the mouse 12/15-lipoxygenase pathways in promoting epithelial wound healing and host defense. Journal of Biological Chemistry 2005; 280: 15267-15278; Gronert K. Lipoxins in the eye and their role in wound healing. *Prostaglandins, Leukotrienes and Essential fatty Acids.* 2005; 73: 221-229; Takano T, Fiore S, Maddox J F, Brady H R, Petasis N A, Serhan C N. Asprin-triggered 15-epi-lipoxin A4 and LXA4 stable analogues are potent inhibitors of acute inflammation: evidence for anti-inflammatory receptors. Journal of Experimental Medicine 1997; 185: 1693-1704; Leoni G, Alam A, Neumann P A, Lambeth J D, Cheng G, McCoy J, Hilgarth R S, Kundu K, Murthy N, Kusters D, Reutelingsperger C, Perretti M, Parkos C A, Neish A S, Nusrat A. Annexin A1, formyl peptide receptor, and NOX1 orchestrate epithelial repair. Journal of Clinical Investigation. 2013; 123:443-54; Leedom A, Sullivan A B, Dong B, Lau D, Gronert K. Endogenous LXA4 circuits are determinants of pathological angiogenesis in response to chronic injury. American Journal of Pathology 2010; 176: 74-84; Tsuruki T, Takahata K, Yoshikawa M. Mechanism of the protective effect of intraperitoneally administered agonists for formyl peptide receptors against chemotherapy-induced alopecia. Biosci Biotechnology Biochemistry. 2007; 71:1198-202).

Pharmaceutical utility of LXA4 and its analogs is hampered by inherent physicochemical properties of the natural poly-olefinic natural product. Therefore, small molecule anti-inflammatory agonists of FPR2 would have a wide variety of therapeutic benefits in inflammatory disorders, including inflammatory disorders of the eye. Targeting FPR2 selectively would also have benefits of reduced side effects as compared to more broadly acting anti-inflammatories, such as steroids or NSAIDs, which have significant side effects of elevated IOP and delays in wound healing in the eye. FPR2 is also expressed in ocular tissues in the cornea and in the posterior of eye, in addition to the inflammatory cells that migrate into the ocular tissues.

Targeting FPR2 selectively would also have benefits in skin wound healing, given its potent anti-inflammatory and pro-epithelial repair role. In addition, some skin diseases have been shown to have an abnormal expression of LL37, a pro-inflammatory cathelicidin which has been shown to be a natural ligand of FPR2. In the chronic inflammatory disease rosacea, LL37 is highly expressed and is believed to play a key role in the pathogenesis (Yamasaki K, Di Nardo A, Bardan A, Murakami M, Ohtake T, Coda A, Dorschner R A, Bonnart C, Descargues P, Hovnanian A, Morhenn V B, Gallo R L. Increased serine protease activity and cathelicidin promotes skin inflammation in rosacea. Nature Medicine. 2007; 13:975-80).

FPR2 thus represents an important novel pro-resolutionary molecular target for the development of new therapeutic agents in diseases or conditions involving excessive inflammatory responses.

Journal of Combinatorial Chemistry (2007), 9(3), 370-385 teaches a thymidinyl dipeptide urea library with structural similarity to the nucleoside peptide class of antibiotics:

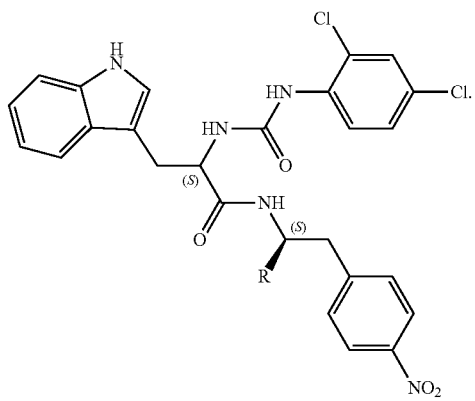

Helvetica Chimica Acta (1998), 81(7), 1254-1263 teaches the synthesis and spectroscopic characterization of 4-chlorophenyl isocyanate (1-chloro-4-isocyanatobenzene) adducts with amino acids as potential dosimeters for the biomonitoring of isocyanate exposure:

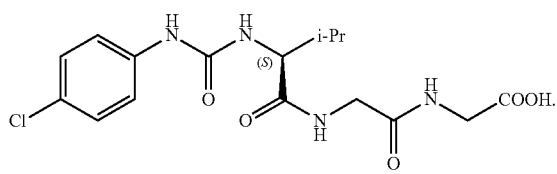

Yingyong Huaxue (1990), 7(1), 1-9 teaches the structure-activity relationships of di- and tripeptide sweeteners and of L-phenyl alanine derivatives:

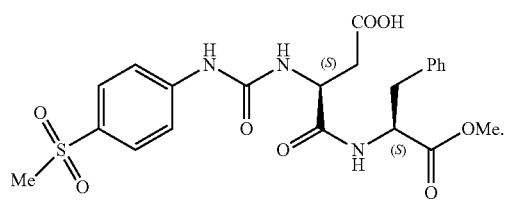

FR 2533210 discloses L-phenyl alanine derivatives as synthetic sweeteners:

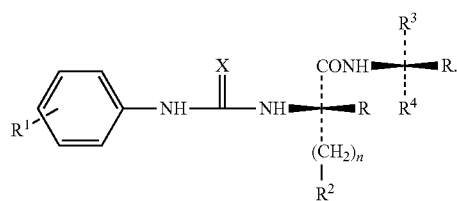

WO2005047899 discloses compounds which selectively activate the FPR2 receptor represented by the following scaffolds:

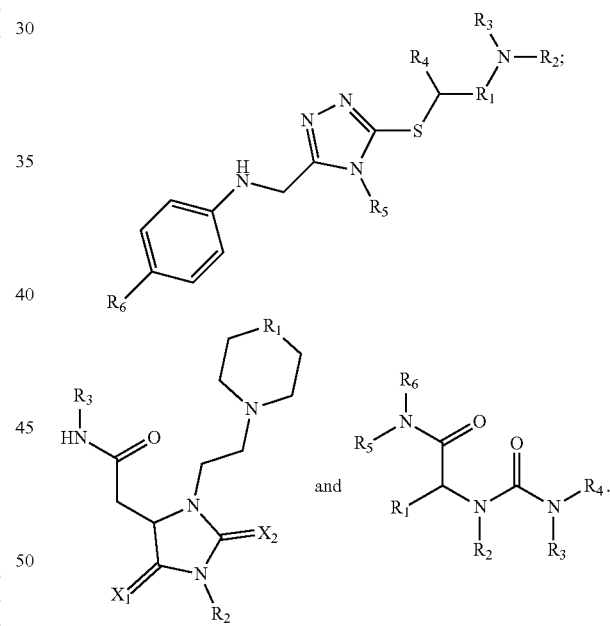

US 2013/0109866 discloses compounds of the general structure below as FPR2 modulators:

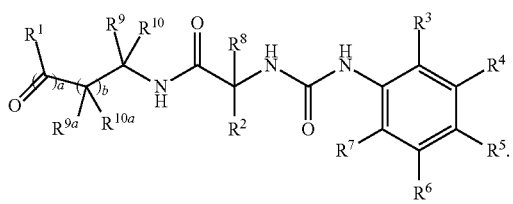

SUMMARY OF THE INVENTION

A group of imidazole urea derivatives, which are potent and selective FPR2 modulators, has been discovered. As such, the compounds described herein are useful in treating a wide variety of disorders associated with modulation of the FPR receptor, such as FPR2. The term "modulator" as used herein, includes but is not limited to: receptor agonist, antagonist, inverse agonist, inverse antagonist, partial agonist, and partial antagonist.

This invention describes compounds of Formula I, which modulate FPR2 biological activity. The compounds in accordance with the present invention are thus of use in medicine, for example, in the treatment of mammalian subjects, including humans, with diseases and/or conditions that are alleviated by FPR modulation, such as FPR2 modulation.

In one aspect, the invention provides a compound represented by Formula I:

Formula I wherein:

each $R^1$, $R^2$, $R^4$ and $R^5$ is independently selected from H, unsubstituted or substituted $C_{1-8}$ alkyl, unsubstituted or substituted $C_{3-8}$ cycloalkyl, unsubstituted or substituted heterocycle, unsubstituted or substituted $C_{6-10}$ aryl, unsubstituted or substituted $C_{3-8}$ cycloalkenyl, halogen, $-S(O)_2NR^{10}R^{11}$, $-NR^{12}R^{13}$, $-S(O)_pR^{14}$, $-C(O)R^{15}$, $-SR^{16}$ and $-OR^{16}$; wherein each said alkyl substituent is independently selected from one or more $R^{20}$; each said cycloalkyl substituent is independently selected from one or more $R^{21}$; each said heterocycle substituent is independently selected from one or more $R^{22}$; each said aryl substituent is independently selected from one or more $R^{23}$; and each said cycloalkenyl substituent is independently selected from one or more $R^{24}$;

$R^3$ is unsubstituted or substituted $C_{1-8}$ alkyl, unsubstituted or substituted $C_{3-8}$ cycloalkyl, unsubstituted or substituted heterocycle, unsubstituted or substituted $C_{6-10}$ aryl, unsubstituted or substituted $C_{3-8}$ cycloalkenyl, halogen, $-S(O)_2NR^{10}R^{11}$, $-NR^{12}R^{13}$, $-S(O)_pR^{14}$, $-C(O)R^{15}$, $-SR^{16}$ or $-OR^{17}$; wherein said alkyl substituent is selected from one or more $R^{20}$; said cycloalkyl substituent is selected from one or more $R^{21}$; said heterocycle substituent is selected from one or more $R^{22}$; said aryl substituent is selected from one or more $R^{23}$; and said cycloalkenyl substituent is selected from one or more $R^{24}$;

$R^6$ is H, or unsubstituted or substituted $C_{1-8}$ alkyl, wherein said alkyl substituent is selected from one or more $R^{25}$;

$R^7$ is H, or unsubstituted or substituted $C_{1-8}$ alkyl, wherein said alkyl substituent is selected from one or more $R^{25}$;

$R^8$ is selected from H, $OR^9$, $NR^{10}R^{11}$, sulfonate, sulfonic acid, phosphonate, phosphonic acid, phosphoric acid and unsubstituted or substituted heterocycle, wherein said heterocycle is selected from tetrazole, imidazole, thiazole, oxazole, triazole, thiophene, pyrazole and pyrrole; and wherein said heterocycle substituent is selected from unsubstituted and substituted $C_{1-8}$ alkyl, wherein said alkyl substituent is selected from OH and halogen;

$R^9$ is H or unsubstituted or substituted $C_{1-8}$ alkyl, wherein said alkyl substituent is selected from OH, halogen, $-OC_{1-8}$ alkyl and $-(OC_{1-8}$ alkylene$)_q-OC_{1-8}$ alkyl;

each $R^{10}$ is independently H or unsubstituted $C_{1-8}$ alkyl, or together with $R^{11}$ forms an unsubstituted heterocyclic ring;

each $R^{11}$ is independently H or unsubstituted $C_{1-8}$ alkyl, or together with $R^{10}$ forms an unsubstituted heterocyclic ring;

each $R^{12}$ is independently H or unsubstituted $C_{1-8}$ alkyl;

each $R^{13}$ is independently H or unsubstituted $C_{1-8}$ alkyl;

each $R^{14}$ is independently OH or unsubstituted $C_{1-8}$ alkyl;

each $R^{15}$ is independently H, unsubstituted $C_{1-8}$ alkyl, unsubstituted $C_{3-8}$ cycloalkyl, unsubstituted heterocycle, unsubstituted $C_{6-10}$ aryl or unsubstituted $C_{3-8}$ cycloalkenyl;

each $R^{16}$ is independently H, unsubstituted $C_{1-8}$ alkyl, unsubstituted $C_{3-8}$ cycloalkyl, unsubstituted heterocycle, unsubstituted $C_{6-10}$ aryl or unsubstituted $C_{3-8}$ cycloalkenyl;

$R^{17}$ is H, unsubstituted $C_{1-8}$ alkyl, unsubstituted $C_{3-8}$ cycloalkyl, unsubstituted heterocycle, unsubstituted $C_{6-10}$ aryl or unsubstituted $C_{3-8}$ cycloalkenyl;

each $R^{18}$ is independently H, unsubstituted $C_{1-8}$ alkyl, $-CH_2-(C_{3-8}$ cycloalkyl), $-CH_2-(C_{3-8}$ cycloalkenyl) or benzyl;

each $R^{19}$ is independently H, unsubstituted $C_{1-8}$ alkyl, $-CH_2-(C_{3-8}$ cycloalkyl), $-CH_2-(C_{3-8}$ cycloalkenyl) or benzyl;

each $R^{20}$ is independently selected from halogen, $-OH$, $-CN$, amino, nitro, ether, thioether, unsubstituted $C_{3-8}$ cycloalkyl, unsubstituted $C_{1-6}$ aryl, unsubstituted heterocycle, ester, aldehyde, ketone, carboxylic acid, amide, sulfonamide, sulfonic acid, phosphonic acid and phosphoric acid;

each $R^{21}$, $R^{22}$, $R^{23}$ and $R^{24}$ is independently selected from halogen, $-OH$, $-CN$, amino, nitro, ether, thioether, unsubstituted $C_{1-8}$ alkyl, unsubstituted $C_{3-8}$ cycloalkyl, unsubstituted $C_{1-6}$ aryl, unsubstituted heterocycle, ester, aldehyde, ketone, carboxylic acid, amide, sulfonamide, sulfonic acid, phosphonic acid and phosphoric acid;

each $R^{25}$ is independently selected from halogen, hydroxyl, amino, ether, thioether, unsubstituted $C_{3-8}$ cycloalkyl, unsubstituted $C_{3-8}$ cycloalkenyl, unsubstituted $C_{1-6}$ aryl, unsubstituted heterocycle, carboxylic acid, amide, sulfonic acid, phosphonic acid and phosphoric acid;

m is 0 or 1;

n is 0, 1, 2, 3, 4, 5, 6, 7 or 8;

each p is independently 1 or 2; and q is 1, 2, 3, 4, 5 or 6;

or a tautomer thereof;

or pharmaceutically acceptable salt of any one of the foregoing;

provided that:

(a) when m is 1, then n is not 0;

(b) when m is 1, then $R^8$ is $OR^9$ or $NR^{10}R^{11}$;

(c) when m is 0 and n is 0, then $R^8$ is H; and (d) when m is 0, and n is not 0, then $R^8$ is not H.

In another aspect, the invention provides for the compound of Formula I, wherein:

$R^1$ is H or halogen;

$R^2$ is H;

$R^3$ is $C_{1-3}$ haloalkyl, halogen or $-OR^{17}$;

$R^4$ is H;
$R^5$ is H or halogen;
$R^6$ is H or unsubstituted $C_{1-3}$ alkyl;
$R^7$ is H;
$R^8$ is selected from H, $OR^9$, $NR^{10}R^{11}$, sulfonate, sulfonic acid, phosphonate, phosphonic acid, phosphoric acid and unsubstituted or substituted heterocycle, wherein said heterocycle is selected from tetrazole, imidazole, thiazole, oxazole, triazole, thiophene, pyrazole and pyrrole; and wherein said heterocycle substituent is selected from unsubstituted and substituted $C_{1-8}$ alkyl, wherein said alkyl substituent is selected from OH and halogen;
$R^9$ is H or unsubstituted $C_{1-4}$ alkyl;
$R^{10}$ is H or unsubstituted $C_{1-3}$ alkyl;
$R^{11}$ is H or unsubstituted $C_{1-3}$ alkyl;
$R^{17}$ is unsubstituted $C_{1-3}$ alkyl;
each $R^{18}$ is H or unsubstituted $C_{1-3}$ alkyl;
each $R^{19}$ is H;
m is 0 or 1; and
n is 0, 1 or 2;
or a tautomer thereof;
or pharmaceutically acceptable salt of any one of the foregoing;
provided that:
(a) when m is 1, then n is not 0;
(b) when m is 1, then $R^8$ is $OR^9$ or $NR^{10}R^{11}$;
(c) when m is 0 and n is 0, then $R^8$ is H; and
(d) when m is 0, and n is not 0, then $R^8$ is not H.

In another aspect, the invention provides for the compound of Formula I, wherein:
$R^1$ is H or halogen;
$R^2$ is H;
$R^3$ is $C_{1-3}$ haloalkyl, halogen or $-OR^{17}$;
$R^4$ is H;
$R^5$ is H or halogen;
$R^6$ is H or unsubstituted $C_{1-3}$ alkyl;
$R^7$ is H;
$R^8$ is H, $OR^9$ or $NR^{10}R^{11}$;
$R^9$ is H or unsubstituted $C_{1-4}$ alkyl;
$R^{10}$ is H or unsubstituted $C_{1-3}$ alkyl;
$R^{11}$ is H or unsubstituted $C_{1-3}$ alkyl;
$R^{17}$ is unsubstituted $C_{1-3}$ alkyl;
each $R^{18}$ is H or unsubstituted $C_{1-3}$ alkyl;
each $R^{19}$ is H;
m is 0 or 1; and
n is 0, 1 or 2;
or a tautomer thereof;
or pharmaceutically acceptable salt of any one of the foregoing;
provided that:
(a) when m is 1, then n is not 0;
(b) when m is 1, then $R^8$ is $OR^9$ or $NR^{10}R^{11}$;
(c) when m is 0 and n is 0, then $R^8$ is H; and
(d) when m is 0, and n is not 0, then $R^8$ is not H.

In another aspect, the invention provides for the compound of Formula I, wherein:
m is 0;
n is 0; and
$R^8$ is H.

In another aspect, the invention provides for the compound of Formula I, wherein:
m is 1;
n is 1;
$R^8$ is $OR^9$, wherein $R^9$ is H or unsubstituted $C_{1-8}$ alkyl;
$R^{18}$ is H or unsubstituted $C_{1-8}$ alkyl; and
$R^{19}$ is H.

In another aspect, the invention provides for the compound of Formula I, wherein:
m is 1;
n is 2;
$R^8$ is $NR^{10}R^{11}$, wherein $R^{10}$ is H or unsubstituted $C_{1-8}$ alkyl, and $R^{11}$ is H or unsubstituted $C_{1-8}$ alkyl;
each $R^{18}$ is H; and
each $R^{19}$ is H.

In another aspect, the invention provides for the compound of Formula I, wherein:
m is 1;
n is 2;
$R^8$ is $OR^9$, wherein $R^9$ is H or unsubstituted $C_{1-8}$ alkyl;
each $R^{18}$ is H; and
each $R^{19}$ is H.

In another aspect, the invention provides for the compound of Formula I, wherein:
m is 0;
n is 2;
$R^8$ is $OR^9$, wherein $R^9$ is H;
each $R^{18}$ is H; and
each $R^{19}$ is H.

In another aspect, the invention provides for the compound of Formula I, wherein:
m is 0;
n is 1 or 2; and
$R^8$ is selected from sulfonate, sulfonic acid, phosphonate, phosphonic acid, phosphoric acid and unsubstituted or substituted heterocycle, wherein said heterocycle is selected from tetrazole, imidazole, thiazole, oxazole, triazole, thiophene, pyrazole and pyrrole; and wherein said heterocycle substituent is selected from unsubstituted and substituted $C_{1-8}$ alkyl, wherein said alkyl substituent is selected from OH and halogen.

In another aspect of the invention, there are provided pharmaceutical compositions comprising a therapeutically effective amount of at least one compound of the invention in a pharmaceutically acceptable carrier.

In yet another aspect of the invention, there are provided methods for treating disorders associated with modulation of the FPR, such as FPR2. Such methods can be performed, for example, by administering to a subject in need thereof a pharmaceutical composition containing a therapeutically effective amount of at least one compound of the invention. In some aspects, the disorder is an inflammatory disease or condition. In further aspects, the inflammatory disease or condition is an ocular inflammatory disease or condition, such as dry eye or post-surgical inflammation, including post-cataract surgical inflammation. In yet further aspects, the inflammatory disease or condition is a dermal inflammatory disease or condition, such as psoriasis or rosacea. In further aspects, the subject is a mammal, including a human.

Some compounds of the invention are shown below, wherein each compound is identified by its IUPAC name and structure.

| IUPAC name | Structure |
|---|---|
| 1-(4-Bromophenyl)-3-[1-(1H-imidazol-2-yl)propyl]urea | 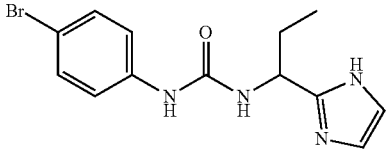 [SMILES: CCC(NC(=O)Nc1ccc(Br)cc1)c1ncc[nH]1] |
| 1-(4-Bromophenyl)-3-[(1S)-1-(1H-imidazol-2-yl)butyl]urea | 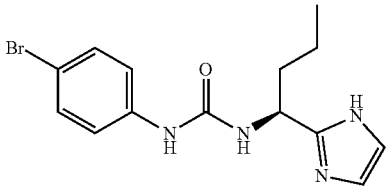 [SMILES: CCC[C@H](NC(=O)Nc1ccc(Br)cc1)c1ncc[nH]1] |
| 1-(4-Bromophenyl)-3-[(1S)-1-(1H-imidazol-2-yl)-2-methylpropyl]urea | 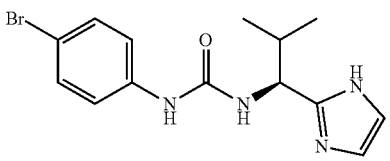 [SMILES: CC(C)[C@H](NC(=O)Nc1ccc(Br)cc1)c1ncc[nH]1] |
| 1-(4-Bromophenyl)-3-(1H-imidazol-2-ylmethyl)urea | 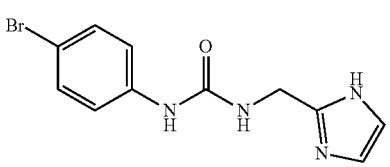 |
| 1-(4-Bromophenyl)-3-[1-(1H-imidazol-2-yl)ethyl]urea | 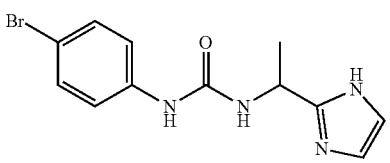 |
| 1-[1-(1H-Imidazol-2-yl)propyl]-3-[4-(trifluoromethyl) phenyl]urea | 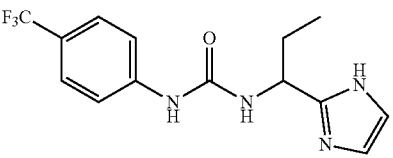 [SMILES: CCC(NC(=O)Nc1ccc(C(F)(F)F)cc1)c1ncc[nH]1] |
| Ethyl [2-(1-{[(4-Bromophenyl)carbamoyl]amino}propyl)-1H-imidazol-1-yl]acetate | 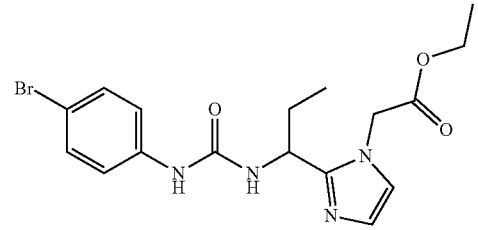 [SMILES: CCOC(=O)Cn1ccnc1C(CC)NC(=O)Nc1ccc(Br)cc1] |
| Ethyl {2-[(1S)-1-{[(4-bromophenyl)carbamoyl]amino} butyl]-1H-imidazol-1-yl}acetate | 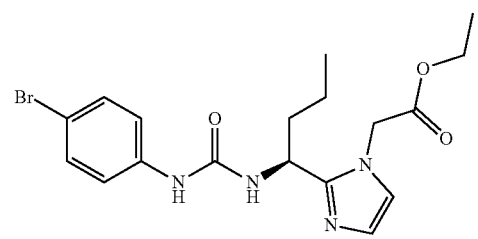 [SMILES: CCC[C@H](NC(=O)Nc1ccc(Br)cc1)c1nccn1CC(=O)OCC] |

| IUPAC name | Structure |
| --- | --- |
| tert-Butyl {2-[(1S)-1-{[(4-Bromophenyl)carbamoyl] amino}butyl]-1H-imidazol-1-yl}acetate | 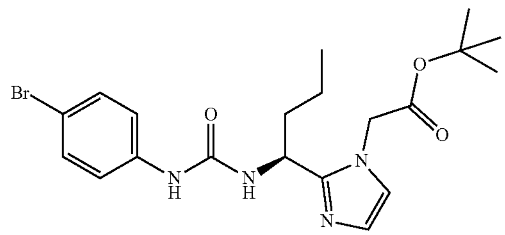 [SMILES: CCC[C@H](NC(=O)Nc1ccc(Br)cc1)c1nccn1CC(=O)OC(C)(C)C] |
| tert-Butyl {2-[(1S)-1-{[(4-Bromophenyl)carbamoyl] amino}-2-methylpropyl]-1H-imidazol-1-yl}acetate | 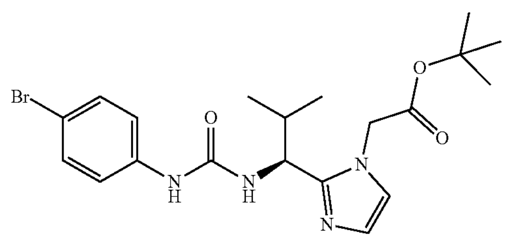 |
| Ethyl [2-({[(4-Bromophenyl)carbamoyl]amino}methyl)-1H-imidazol-1-yl]acetate | 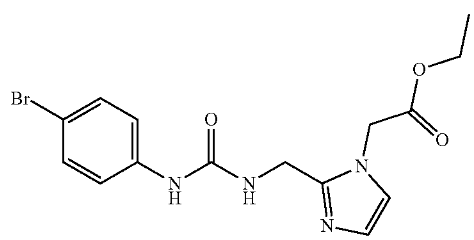 [SMILES: CCOC(=O)Cn1ccnc1CNC(=O)Nc1ccc(Br)cc1] |
| Ethyl [2-(1-{[(4-Bromophenyl)carbamoyl]amino}ethyl)-1H-imidazol-1-yl]acetate | 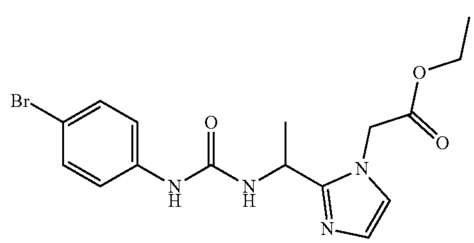 [SMILES: CCOC(=O)Cn1ccnc1C(C)NC(=O)Nc1ccc(Br)cc1] |
| 1-(4-Bromophenyl)-3-{1-[1-(2-hydroxyethyl)-1H-imidazol-2-yl]ethyl}urea | 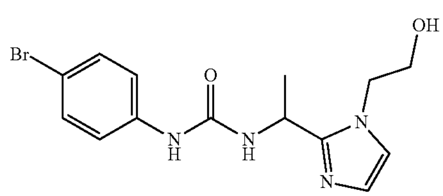 [SMILES: CC(NC(=O)Nc1ccc(Br)cc1)c1nccn1CCO] |
| Ethyl 2-[2-({[(4-Bromophenyl)carbamoyl]amino} methyl)-1H-imidazol-1-yl]propanoate | 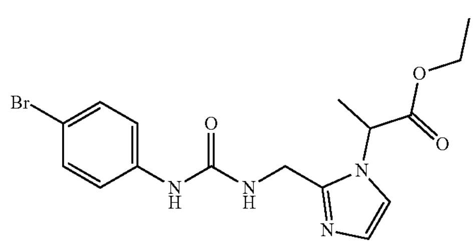 [SMILES: CCOC(=O)C(C)n1ccnc1CNC(=O)Nc1ccc(Br)cc1] |

-continued

| IUPAC name | Structure |
|---|---|
| Ethyl {2-[1-({[4-(trifluoromethyl)phenyl]carbamoyl}amino)propyl]-1H-imidazol-1-yl}acetate | 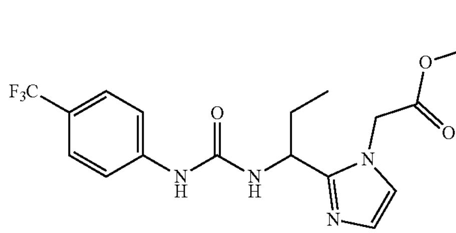 |
| [2-(1-{[(4-Bromophenyl)carbamoyl]amino}propyl)-1H-imidazol-1-yl]acetic acid | 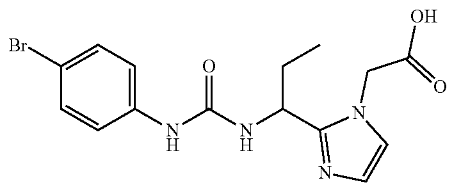 [SMILES: CCC(NC(=O)Nc1ccc(Br)cc1)c1nccn1CC(=O)O] |
| [2-({[(4-Bromophenyl)carbamoyl]amino}methyl)-1H-imidazol-1-yl]acetic acid | 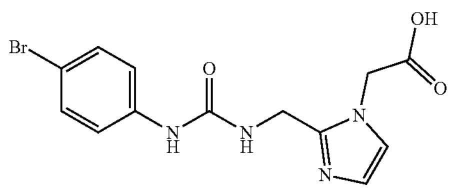 [SMILES: O=C(O)Cn1ccnc1CNC(=O)Nc1ccc(Br)cc1] |
| [2-(1-{[(4-Bromophenyl)carbamoyl]amino}ethyl)-1H-imidazol-1-yl]acetic acid | 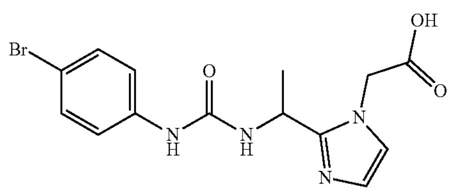 [SMILES: CC(NC(=O)Nc1ccc(Br)cc1)c1nccn1CC(=O)O] |
| 2-[2-({[(4-Bromophenyl)carbamoyl]amino}methyl)-1H-imidazol-1-yl]propanoic acid | 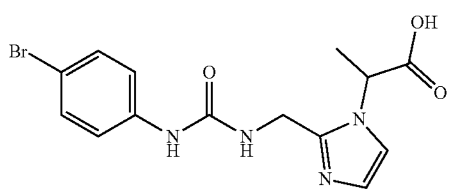 [SMILES: CC(C(=O)O)n1ccnc1CNC(=O)Nc1ccc(Br)cc1] |
| 3-[2-(1-{[(4-Bromophenyl)carbamoyl]amino}propyl)-1H-imidazol-1-yl]propanoic acid | 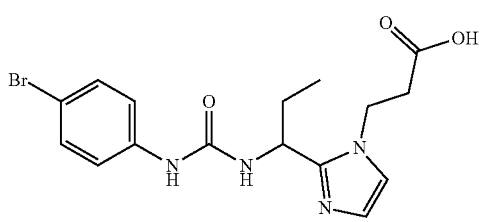 [SMILES: CCC(NC(=O)Nc1ccc(Br)cc1)c1nccn1CCC(=O)O] |
| {2-[1-({[4-(Trifluoromethyl)phenyl]carbamoyl}amino)propyl]-1H-imidazol-1-yl}acetic acid | 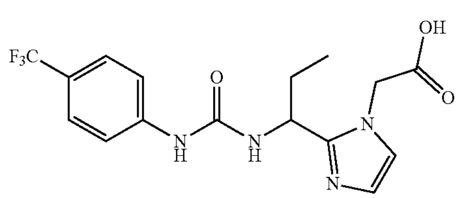 [SMILES: CCC(NC(=O)Nc1ccc(C(F)(F)F)cc1)c1nccn1CC(=O)O] |

-continued

| IUPAC name | Structure |
|---|---|
| 3-{2-[1-({[4-(Trifluoromethyl)phenyl]carbamoyl}amino) propyl]-1H-imidazol-1-yl} propanoic acid | 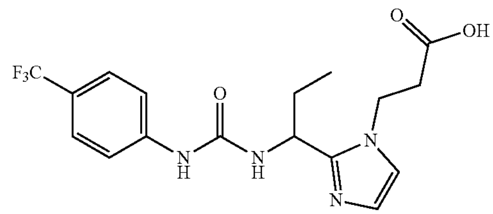 [SMILES: CCC(NC(=O)Nc1ccc(C(F)(F)F)cc1)c1nccn1CCC(=O)O] |
| Ethyl 3-[2-(1-{[(4-Bromophenyl)carbamoyl]amino}propyl)-1H-imidazol-1-yl]propanoate | 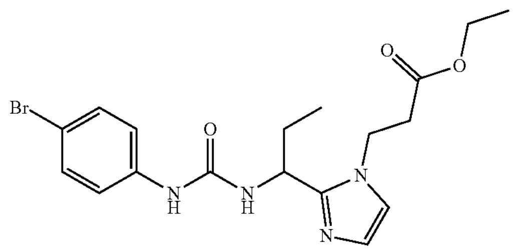 [SMILES: CCOC(=O)CCn1ccnc1C(CC)NC(=O)Nc1ccc(Br)cc1] |
| Ethyl 3-[2-(1-{[(4-Bromophenyl)carbamoyl]amino} ethyl)-1H-imidazol-1-yl]propanoate | 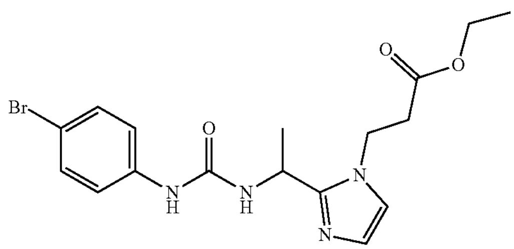 [SMILES: CCOC(=O)CCn1ccnc1C(C)NC(=O)Nc1ccc(Br)cc1] |
| Ethyl 3-{2-[1-({[4-(trifluoromethyl)phenyl]carbamoyl}amino)propyl]-1H-imidazol-1-yl}propanoate | 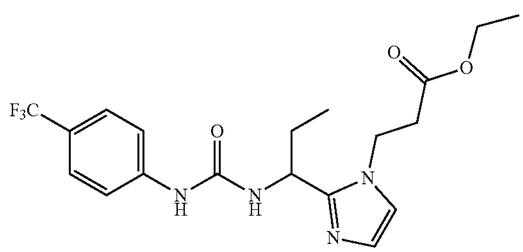 [SMILES: CCOC(=O)CCn1ccnc1C(CC)NC(=O)Nc1ccc(C(F)(F)F)cc1] |
| {2-[(1S)-1-{[(4-Bromophenyl)carbamoyl]amino}butyl]-1H-imidazol-1-yl}acetic acid | 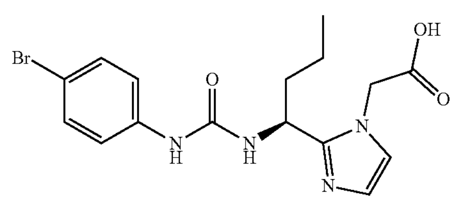 [SMILES: CCC[C@H](NC(=O)Nc1ccc(Br)cc1)c1nccn1CC(=O)O] |
| {2-[(1S)-1-{[(4-Bromophenyl)carbamoyl]amino}-2-methylpropyl]-1H-imidazol-1-yl}acetic acid | 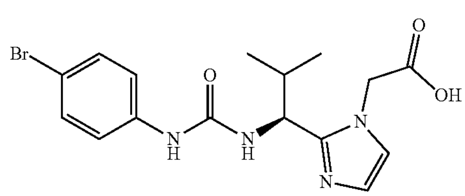 [SMILES: CC(C)[C@H](NC(=O)Nc1ccc(Br)cc1)c1nccn1CC(=O)O] |
| 1-[(1S)-1-(1H-imidazol-2-yl)-2-methyl propyl]-3-[4-(trifluoromethyl)phenyl] urea | 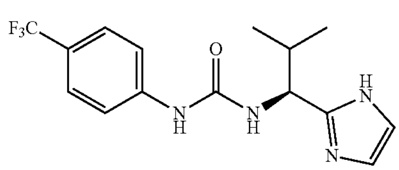 [SMILES: CC(C)[C@H](NC(=O)Nc1ccc(C(F)(F)F)cc1)c1ncc[nH]1] |

-continued

| IUPAC name | Structure |
|---|---|
| 1-(4-Chlorophenyl)-3-[(1S)-1-(1H-imidazol-2-yl)-2-methylpropyl]urea | 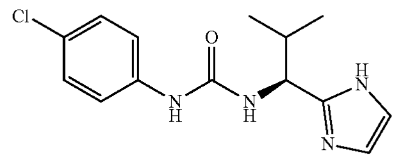 [SMILES: CC(C)[C@H](NC(=O)Nc1ccc(Cl)cc1)c1ncc[nH]1] |
| 1-(4-Bromo-2-fluorophenyl)-3-[(1S)-1-(1H-imidazol-2-yl)-2-methylpropyl]urea | 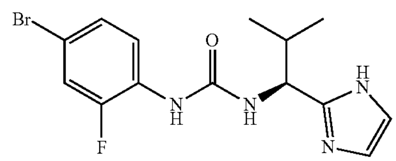 [SMILES: CC(C)[C@H](NC(=O)Nc1ccc(Br)cc1F)c1ncc[nH]1] |
| 1-[(1S)-1-(1H-imidazol-2-yl)-2-methylpropyl]-3-(4-methoxyphenyl)urea | 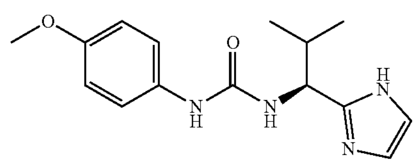 [SMILES: COc1ccc(NC(=O)N[C@H](c2ncc[nH]2)C(C)C)cc1] |
| tert-Butyl (2-{(1S)-2-methyl-1-[({[4-(trifluoromethyl)phenyl]amino}carbonyl) amino]propyl}-1H-imidazol-1-yl)acetate urea | 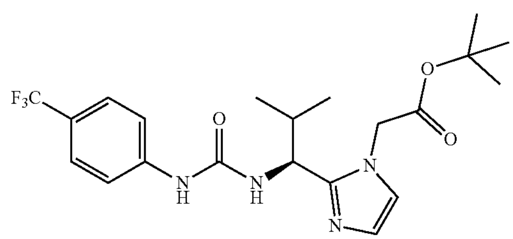 [SMILES: CC(C)[C@H](NC(=O)Nc1ccc(C(F)(F)F)cc1)c1nccn1CC(=O)OC(C)(C)C] |
| tert-Butyl {2-[(1S)-1-({[(4-chlorophenyl)amino]carbonyl}amino)-2-methylpropyl]-1H-imidazol-1-yl}acetate | 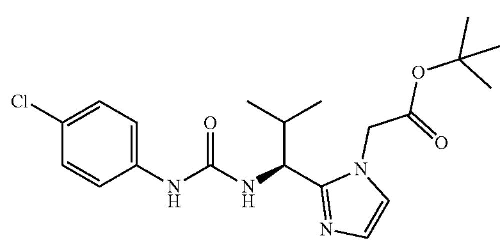 [SMILES: CC(C)[C@H](NC(=O)Nc1ccc(Cl)cc1)c1nccn1CC(=O)OC(C)(C)C] |
| tert-Butyl {2-[(1S)-1-({[(4-bromo-2-fluorophenyl)amino]carbonyl}amino)-2-methylpropyl]-1H-imidazol-1-yl}acetate | 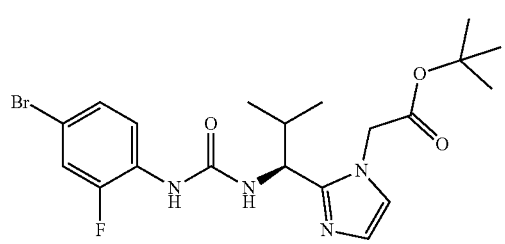 [SMILES: CC(C)[C@H](NC(=O)Nc1ccc(Br)cc1F)c1nccn1CC(=O)OC(C)(C)C] |
| tert-Butyl {2-[(1S)-1-({[(4-methoxyphenyl)amino]carbonyl}amino)-2-methylpropyl]-1H-imidazol-1-yl}acetate | 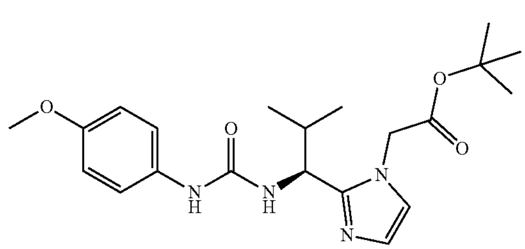 [SMILES: COc1ccc(NC(=O)N[C@H](c2nccn2CC(=O)OC(C)(C)C)C(C)C)cc1] |

| IUPAC name | Structure |
|---|---|
| (2-{(1S)-2-Methyl-1-[({[4-(trifluoromethyl)phenyl]amino}carbonyl)amino]propyl}-1H-imidazol-1-yl)acetic acid | 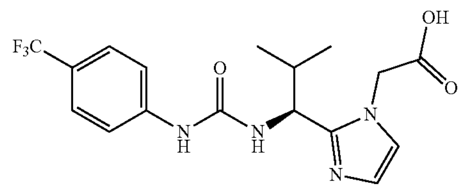 [SMILES: CC(C)[C@H](NC(=O)Nc1ccc(C(F)(F)F)cc1)c1nccn1CC(=O)O] |
| {2-[(1S)-1-({[(4-Chlorophenyl)amino]carbonyl}amino)-2-methylpropyl]-1H-imidazol-1-yl}acetic acid | 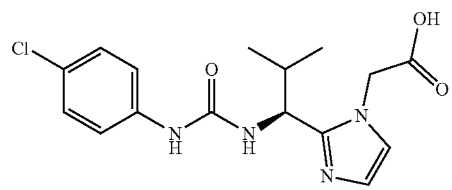 [SMILES: CC(C)[C@H](NC(=O)Nc1ccc(Cl)cc1)c1nccn1CC(=O)O] |
| {2-[(1S)-1-({[(4-bromo-2-fluorophenyl)amino]carbonyl}amino)-2-methylpropyl]-1H-imidazol-1-yl}acetic acid | 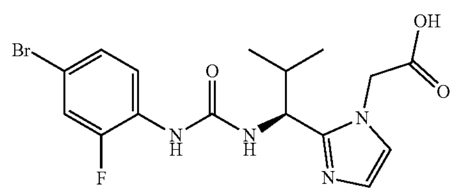 [SMILES: CC(C)[C@H](NC(=O)Nc1ccc(Br)cc1F)c1nccn1CC(=O)O] |
| {2-[(1S)-1-({[(4-methoxyphenyl)amino]carbonyl}amino)-2-methylpropyl]-1H-imidazol-1-yl}acetic acid | 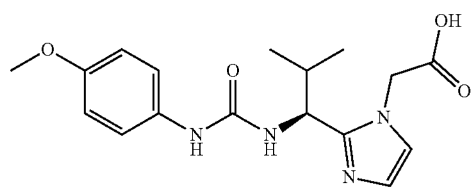 [SMILES: COc1ccc(NC(=O)N[C@H](c2nccn2CC(=O)O)C(C)C)cc1] |
| 2-(2-{(1S)-2-methyl-1-[({[4-(trifluoromethyl)phenyl]amino}carbonyl)amino] propyl}-1H-imidazol-1-yl)acetamide | 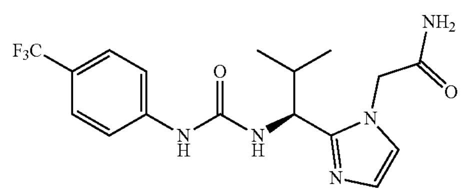 [SMILES: CC(C)[C@H](NC(=O)Nc1ccc(C(F)(F)F)cc1)c1nccn1CC(N)=O] |
| 2-(2-{(1S)-2-methyl-1-[({[4-(trifluoromethyl)phenyl]amino}carbonyl)amino] propyl}-1H-imidazol-1-yl)-N-propylacetamide | 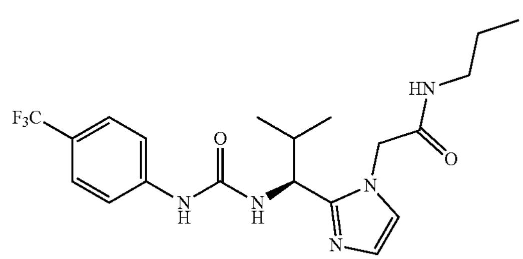 [SMILES: CCCNC(=O)Cn1ccnc1[C@@H](NC(=O)Nc1ccc(C(F)(F)F)cc1)C(C)C] |
| N,N-Dimethyl-2-(2-{(1S)-2-methyl-1-[({[4-(trifluoromethyl)phenyl]amino}carbonyl)amino]propyl}-1H-imidazol-1-yl)acetamide | 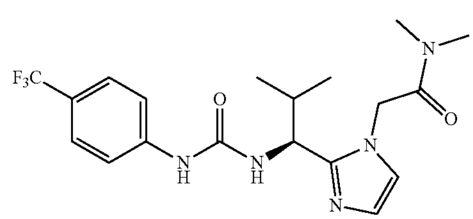 [SMILES: CC(C)[C@H](NC(=O)Nc1ccc(C(F)(F)F)cc1)c1nccn1CC(=O)N(C)C] |

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

The following abbreviations are used herein:

| The following abbreviations are used herein: | |
|---|---|
| Et$_3$N | triethylamine |
| CH$_2$Cl$_2$ | dichloromethane |
| CD$_3$OD | deuterated methanol |
| Na$_2$SO$_4$ | sodium sulfate |
| DMF | N,N-dimethylformamide |
| EtOAc | ethyl acetate |
| DMAP | 4-dimethylaminopyridine |
| HCl | hydrochloric acid |
| NaOH | sodium hydroxide |
| CDCl$_3$ | deuterated chloroform |
| EtOH | ethanol |
| K$_2$CO$_3$ | potassium carbonate |
| NH$_4$Cl | ammonium chloride |
| DMSO-d$_6$ | deuterated dimethylsulfoxide |
| TMS | tetramethylsilane |
| HOBt | hydroxybenzotriazole |

The term "alkyl", as used herein, refers to saturated, monovalent or divalent hydrocarbon moieties having linear or branched moieties or combinations thereof. Alkyl groups typically contain 1 to 8 carbon atoms (i.e., $C_{1-8}$ alkyl), but may contain a variable number of carbon atoms as specified. For example, an alkyl group may comprise 1 to 4 carbon atoms (i.e., $C_{1-4}$ alkyl), or 1 to 3 carbon atoms (i.e., $C_{1-3}$ alkyl). Alkyl groups are optionally substituted with one or more groups including, but not limited to: halogen, hydroxyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid. For example, substituted alkyl includes haloalkyl, such as perhaloalkyl (e.g., —CF$_3$). In a further example, substituted alkyl includes C$_1$ alkyl substituted with C$_{1-6}$ aryl (e.g., benzyl, which is (—CH$_2$-phenyl). One or more methylene (CH$_2$) groups of an alkyl can be replaced by oxygen, sulfur, carbonyl, sulfoxide, sulfonyl, or by a divalent $C_{3-6}$ cycloalkyl; one or more methine (CH) groups of an alkyl can be replaced by nitrogen. Unsubstituted $C_{1-4}$ alkyl includes methyl, ethyl, n-propyl, isopropyl, n-butyl, isobutyl, sec-butyl and t-butyl. Unsubstituted $C_{1-3}$ alkyl includes methyl, ethyl, n-propyl and isopropyl.

The term "alkylene" as used herein refers to a bivalent saturated aliphatic radical derived from an alkene by opening of the double bond, or from an alkane by removal of two hydrogen atoms from different carbon atoms. An alkylene may comprise 1 to 8 carbon atoms (i.e., $C_{1-8}$ alkylene), for example, a C$_1$ alkylene is methylene (—CH$_2$—); a C$_2$ alkylene is ethylene (—CH$_2$CH$_2$—), and so on.

The term "cycloalkyl", as used herein, refers to a monovalent or divalent group of 3 to 8 carbon atoms (i.e., $C_{3-8}$ cycloalkyl) derived from a saturated cyclic hydrocarbon. Cycloalkyl groups can be monocyclic or polycyclic. Cycloalkyl groups are optionally substituted with one or more groups including, but not limited to: halogen, hydroxyl, alkyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid.

The term "cycloalkenyl", as used herein, refers to a monovalent or divalent group of 3 to 8 carbon atoms (i.e., $C_{3-8}$ cycloalkenyl) derived from a saturated cycloalkyl having one or more double bonds. Cycloalkenyl groups can be monocyclic or polycyclic. Cycloalkenyl groups are optionally substituted by one or more groups including, but not limited to: halogen, hydroxyl, alkyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid.

The term "heterocycle" as used herein, refers to a 3 to 10 membered ring, which can be aromatic or non-aromatic, saturated or unsaturated, containing at least one heteroatom selected from O, N and S, or combinations of at least two thereof, interrupting the carbocyclic ring structure. The heterocyclic ring can be interrupted by one or more C=O; the S and/or N heteroatom can be oxidized. Heterocycles can be monocyclic or polycyclic. Heterocyclic ring moieties are optionally substituted with one or more groups including, but not limited to: halogen, hydroxyl, alkyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid.

The term "aryl" as used herein, refers to an aromatic hydrocarbon ring containing 6 to 10 carbon atoms (i.e., $C_{6-10}$ aryl). Aryl groups are optionally substituted by one or more groups including, but not limited to: halogen, hydroxyl, alkyl, cycloalkyl, heterocycle, aryl, ether, amine, nitro, nitrile, amide, sulfonamide, ester, aldehyde, carboxylic acid, ketone, sulfonic acid, phosphonic acid, and/or phosphoric acid. Aryl can be monocyclic or polycyclic.

The term "halogen", as used herein, refers to an atom of chlorine, bromine, fluorine and/or iodine.

The term "amine" or "amino" as used herein, represents a group of formula "—NR$^x$R$^y$", wherein R$^x$ and R$^y$ can be the same or independently H, alkyl, aryl, cycloalkyl, cycloalkenyl or heterocyclyl, as defined above.

The term "amide" as used herein, represents a group of formula "—C(O)N(R$^x$)(R$^y$)" or "—NR$^x$C(O)R$^y$" wherein R$^x$ and R$^y$ can be the same or independently H, alkyl, aryl, cycloalkyl, cycloalkenyl or heterocycyl, as defined above.

The term "sulfonamide" as used herein, represents a group of formula "—S(O)$_2$N(R$^x$)(R$^y$)" or "—NR$^x$S(O)$_2$R$^y$" wherein R$^x$ and R$^y$ can be the same or independently H, alkyl, aryl, cycloalkyl, cycloalkenyl or heterocyclyl, as defined above.

The term "aldehyde" as used herein, represents a group of formula "—C(O)H".

The term "ester" as used herein, represents a group of formula "—C(O)O(R$^x$)", wherein R$^x$ is alkyl, aryl, cycloalkyl, cycloalkenyl or heterocyclyl, as defined above.

The term "ketone" as used herein, represents a group of formula "—C(O)R$^x$" wherein R$^x$ is alkyl, aryl, cycloalkyl, cycloalkenyl or heterocyclyl, as defined above.

The term "hydroxyl" as used herein, represents a group of formula "—OH".

The term "carbonyl" as used herein, represents a group of formula "—C(O)—".

The term "carboxyl" as used herein, represents a group of formula "—C(O)O—".

The term "carboxylic acid" as used herein, represents a group of formula "—C(O)OH".

The term "carboxylate" as used herein, represents a group of formula "—C(O)O—".

The term "sulfoxide" as used herein, represents a group of formula "—S(O)—".

The term "sulfonyl" as used herein, represents a group of formula "—S$_2$—".

The term "sulfate" as used herein, represents a group of formula "—OS(O)$_2$O$^-$".

The term "sulphonic acid" as used herein, represents a group of formula "—S(O)$_2$OH".

The term "phosphonic acid" as used herein, represents a group of formula "—P(O)(OH)$_2$".

The term "phosphoric acid" as used herein, represents a group of formula "—(O)P(O)(OH)$_2$".

The term "nitro" as used herein, represents a group of formula "—NO$_2$".

The term "nitrile" as used herein, represents a group of formula "—CN".

The term "ether" as used herein, represents a group of formula "—OR$^x$", wherein R$^x$ is alkyl, aryl, cycloalkyl, cycloalkenyl or heterocyclyl, as defined above.

The term "thioether" as used herein, represents a group of formula "—SR$^x$", wherein R$^x$ is alkyl, aryl, cycloalkyl, cycloalkenyl or heterocyclyl, as defined above.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent. The term "pharmaceutically acceptable salts" refers to salts or complexes that retain the desired biological activity of compounds of the invention, and exhibit minimal or no undesired toxicological effects. The "pharmaceutically acceptable salts" according to the invention include therapeutically active, non-toxic base or acid salt forms, which the compounds of Formula I are able to form.

The term "carboxylate isostere", as used herein, refers to a group that replaces a carboxylic acid, such as a group selected from sulfonate, sulfonic acid, phosphonate, phosphonic acid, phosphoric acid, and unsubstituted or substituted heterocycle, wherein said heterocycle is selected from tetrazole, imidazole, thiazole, oxazole, triazole, thiophene, pyrazole and pyrrole; and wherein said heterocycle substituent is selected from unsubstituted and substituted C$_{1-8}$ alkyl, wherein said alkyl substituent is selected from OH and halogen.

The term "therapeutically effective amount" means the amount of a pharmaceutical composition that will elicit a biological or medical response in a subject in need thereof that is being sought by the researcher, veterinarian, medical doctor or other clinician.

In one embodiment, the present invention provides a compound represented by Formula I:

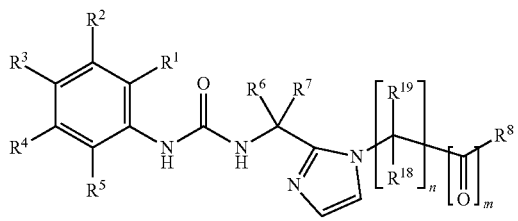

Formula I wherein:

each R$^1$, R$^2$, R$^4$ and R$^5$ is independently selected from H, unsubstituted or substituted C$_{1-8}$ alkyl, unsubstituted or substituted C$_{3-8}$ cycloalkyl, unsubstituted or substituted heterocycle, unsubstituted or substituted C$_{6-10}$ aryl, unsubstituted or substituted C$_{3-8}$ cycloalkenyl, halogen, —S(O)$_2$NR$^{10}$R$^{11}$, —NR$^{12}$R$^{13}$, —S(O)$_p$R$^{14}$, —C(O)R$^{15}$, —SR$^{16}$ and —OR$^{16}$; wherein each said alkyl substituent is independently selected from one or more R$^{20}$; each said cycloalkyl substituent is independently selected from one or more R$^{21}$; each said heterocycle substituent is independently selected from one or more R$^{22}$; each said aryl substituent is independently selected from one or more R$^{23}$; and each said cycloalkenyl substituent is independently selected from one or more R$^{24}$;

R$^3$ is unsubstituted or substituted C$_{1-8}$ alkyl, unsubstituted or substituted C$_{3-8}$ cycloalkyl, unsubstituted or substituted heterocycle, unsubstituted or substituted C$_{6-10}$ aryl, unsubstituted or substituted C$_{3-8}$ cycloalkenyl, halogen, —S(O)$_2$NR$^{10}$R$^{11}$, —NR$^{12}$R$^{13}$, —S(O)$_p$R$^{14}$, —C(O)R$^{15}$, —SR$^{11}$ or —OR$^{17}$; wherein said alkyl substituent is selected from one or more R$^{20}$; said cycloalkyl substituent is selected from one or more R$^{21}$; said heterocycle substituent is selected from one or more R$^{22}$; said aryl substituent is selected from one or more R$^{23}$; and said cycloalkenyl substituent is selected from one or more R$^{24}$;

R$^6$ is H, or unsubstituted or substituted C$_{1-8}$ alkyl, wherein said alkyl substituent is selected from one or more R$^{25}$;

R$^7$ is H, or unsubstituted or substituted C$_{1-8}$ alkyl, wherein said alkyl substituent is selected from one or more R$^{25}$;

R$^8$ is selected from H, OR$^9$, NR$^{10}$R$^{11}$, sulfonate, sulfonic acid, phosphonate, phosphonic acid, phosphoric acid and unsubstituted or substituted heterocycle, wherein said heterocycle is selected from tetrazole, imidazole, thiazole, oxazole, triazole, thiophene, pyrazole, pyrrole; and wherein said heterocycle substituent is selected from unsubstituted and substituted C$_{1-8}$ alkyl, wherein said alkyl substituent is selected from OH and halogen;

R$^9$ is H or unsubstituted or substituted C$_{1-8}$ alkyl, wherein said alkyl substituent is selected from OH, halogen, —OC$_{1-8}$ alkyl and —(OC$_{1-8}$ alkylene)$_q$-OC$_{1-8}$ alkyl;

each R$^{10}$ is independently H or unsubstituted C$_{1-8}$ alkyl, or together with R$^{11}$ forms an unsubstituted heterocyclic ring;

each R$^{11}$ is independently H or unsubstituted C$_{1-8}$ alkyl, or together with R$^{10}$ forms an unsubstituted heterocyclic ring;

each R$^{12}$ is independently H or unsubstituted C$_{1-8}$ alkyl;

each R$^{13}$ is independently H or unsubstituted C$_{1-8}$ alkyl;

each R$^{14}$ is independently OH or unsubstituted C$_{1-8}$ alkyl;

each R$^{15}$ is independently H, unsubstituted C$_{1-8}$ alkyl, unsubstituted C$_{3-8}$ cycloalkyl, unsubstituted heterocycle, unsubstituted C$_{6-10}$ aryl or unsubstituted C$_{3-8}$ cycloalkenyl;

each R$^{16}$ is independently H, unsubstituted C$_{1-8}$ alkyl, unsubstituted C$_{3-8}$ cycloalkyl, unsubstituted heterocycle, unsubstituted C$_{6-10}$ aryl or unsubstituted C$_{3-8}$ cycloalkenyl;

R$^{17}$ is H, unsubstituted C$_{1-8}$ alkyl, unsubstituted C$_{3-8}$ cycloalkyl, unsubstituted heterocycle, unsubstituted C$_{6-10}$ aryl or unsubstituted C$_{3-8}$ cycloalkenyl;

each R$^{18}$ is independently H, unsubstituted C$_{1-8}$ alkyl, —CH$_2$—(C$_{3-8}$ cycloalkyl), —CH$_2$—(C$_{3-8}$ cycloalkenyl) or benzyl;

each R$^{19}$ is independently H, unsubstituted C$_{1-8}$ alkyl, —CH$_2$—(C$_{3-8}$ cycloalkyl), —CH$_2$—(C$_{3-8}$ cycloalkenyl) or benzyl;

each R$^{20}$ is independently selected from halogen, —OH, —CN, amino, nitro, ether, thioether, unsubstituted C$_{3-8}$ cycloalkyl, unsubstituted C$_{1-6}$ aryl, unsubstituted heterocycle, ester, aldehyde, ketone, carboxylic acid, amide, sulfonamide, sulfonic acid, phosphonic acid and phosphoric acid;

each $R^{21}$, $R^{22}$, $R^{23}$ and $R^{24}$ is independently selected from halogen, —OH, —CN, amino, nitro, ether, thioether, unsubstituted $C_{1-8}$ alkyl, unsubstituted $C_{3-8}$ cycloalkyl, unsubstituted $C_{1-6}$ aryl, unsubstituted heterocycle, ester, aldehyde, ketone, carboxylic acid, amide, sulfonamide, sulfonic acid, phosphonic acid and phosphoric acid;

each $R^{25}$ is independently selected from halogen, hydroxyl, amino, ether, thioether, unsubstituted $C_{3-8}$ cycloalkyl, unsubstituted $C_{3-8}$ cycloalkenyl, unsubstituted $C_{1-6}$ aryl, unsubstituted heterocycle, carboxylic acid, amide, sulfonic acid, phosphonic acid and phosphoric acid;

m is 0 or 1;
n is 0, 1, 2, 3, 4, 5, 6, 7 or 8;
each p is independently 1 or 2; and
q is 1, 2, 3, 4, 5 or 6;
or a tautomer thereof;
or pharmaceutically acceptable salt of any one of the foregoing;
provided that:
(a) when m is 1, then n is not 0;
(b) when m is 1, then $R^6$ is $OR^9$ or $NR^{10}R^{11}$;
(c) when m is 0 and n is 0, then $R^8$ is H; and
(d) when m is 0, and n is not 0, then $R^8$ is not H.

In some embodiments, the invention provides for the compound of Formula I, wherein:
m is 0;
n is 1, 2, 3, 4, 5, 6, 7 or 8; and
$R^8$ is a carboxylate isostere selected from sulfonate, sulfonic acid, phosphonate, phosphonic acid, phosphoric acid and unsubstituted or substituted heterocycle, wherein said heterocycle is selected from tetrazole, imidazole, thiazole, oxazole, triazole, thiophene, pyrazole and pyrrole; and wherein said heterocycle substituent is selected from unsubstituted and substituted $C_{1-8}$ alkyl, wherein said alkyl substituent is selected from OH and halogen.

Some compounds of the invention may form salts with acids or bases, including pharmaceutically acceptable acids or bases. Such pharmaceutically acceptable salts of the compounds described herein are within the scope of the invention.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic acid and the like. The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-arginine, ethanolamine, betaine, benzathine, morpholine and the like. (See Handbook of Pharmaceutical Salts, P. Heinrich Stahl & Camille G. Wermuth (Eds), Verlag Helvetica Chimica Acta, Zürich, 2002, 329-345.)

Some of the compounds of Formula I and some of their intermediates may contain one or more asymmetric centers in their structure; each asymmetric center may be present in an R or S configuration, said R and S notation corresponding to the rules described in Pure and Applied Chemistry (1976), 45, 11-13. As such, the compounds may exist in enantiomeric as well as in diastereomeric forms. Unless it is specifically noted otherwise, the scope of the present invention includes all enantiomers, diastereomers and mixtures thereof, including racemic mixtures.

As will be evident to those skilled in the art, individual diastereoisomeric forms can be obtained by separation of mixtures thereof in a conventional manner. For example, chromatographic separation may be employed; chiral chromatography may be performed to separate individual enantiomers.

The present invention includes all pharmaceutically acceptable isotopically enriched compounds. Any compound of the invention may contain one or more isotopic atoms enriched or different than the natural ratio, such as deuterium $^2$H (or D) in place of hydrogen $^1$H (or H), or use of $^{13}$C enriched material in place of $^{12}$C and the like. Similar substitutions can be employed for N, O, S and P. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

In an embodiment of the invention, there are provided pharmaceutical compositions including a therapeutically effective amount of at least one compound of the invention in a pharmaceutically acceptable carrier.

The compounds of the invention and the pharmaceutical compositions comprising at least one compound of the invention are indicated for use in treating or preventing conditions in which there is likely to be a component involving the FPR, such as FPR2.

In a further embodiment of the invention, there are provided methods for treating disorders associated with modulation of the FPR, such as FPR2. Such methods can be performed, for example, by administering to a subject in need thereof a pharmaceutical composition comprising a therapeutically effective amount of at least one compound of the invention.

More specifically, the present invention provides for:
use of a compound of the invention in the manufacture of a medicament for the treatment of a mammalian subject, including a human subject, having one or more diseases or conditions that are alleviated by FPR modulation (such as FPR2 modulation); and/or a method of treating a mammalian subject, including a human subject, having one or more diseases or conditions that are alleviated by FPR modulation (such as FPR2 modulation);

wherein the disease or condition is an ocular inflammatory disease, including but not limited to: age-related macular degeneration, wet macular degeneration, dry macular degeneration, uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity, acute macular neuroretinopathy, central serous chorioretinopathy, cystoid macular edema, and diabetic macular edema; infectious keratitis, herpetic keratitis, corneal angiogenesis, lymphangiogenesis, uveitis, retinitis, choroiditis, such as acute multifocal placoid pigment epitheliopathy, Behcets disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi-and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coats disease, parafoveal telangiectasis, hemiretinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, bone marrow transplant retinopathy, corneal wound healing, post-surgical corneal wound healing and/or inflammation, and post-cataract surgical inflammation; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardts disease and fundus flavimaculatus, Bests disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, blepharitis, meibomian gland dysfunction (MDG), glaucoma, branch vein occlusion, Bests vitelliform macular degeneration, retinitis pigmentosa, proliferative vitreoretinopathy (PVR), and any other degenerative disease of either the photoreceptors or the retinal pigment epithelium (Perretti, Mauro et al. Pharmacology & Therapeutics 127 (2010) 175-188).

In other embodiments, the present invention provides for:
use of a compound of the invention in the manufacture of a medicament for the treatment of a mammalian subject, including a human subject, having one or more diseases or conditions that are alleviated by FPR modulation (such as FPR2 modulation); and/or
a method of treating a mammalian subject, including a human subject, having one or more diseases or conditions that are alleviated by FPR modulation (such as FPR2 modulation);
wherein the disease or condition is a dermal inflammatory disease or condition, including, but not limited to: dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation, alopecia, scarring and non-scarring forms.

In yet other embodiments, the present invention provides for:
use of a compound of the invention in the manufacture of a medicament for the treatment of a mammalian subject, including a human subject, having one or more diseases or conditions that are alleviated by FPR modulation (such as FPR2 modulation); and/or
a method of treating a mammalian subject, including a human subject, having one or more diseases or conditions that are alleviated by FPR modulation (such as FPR2 modulation);
wherein the disease or condition is selected from: stroke, coronary artery disease, an obstructive airway disease, an HIV-mediated retroviral infection, a cardiovascular disorder such as coronary artery disease, neuroinflammation, a neurological disorder, pain, an immunological disorder, rheumatoid arthritis, asthma, an allergic disorder, systemic lupus erythematosus, Alzheimer's disease, arthritis, sepsis, inflammatory bowel disease, cachexia and angina pectoris.

In a further embodiment of the invention, the method of treating a disease or condition alleviated by modulation of the FPR receptor, such as modulation of the FPR2, comprises administering to the subject in need of the treatment a therapeutically effective amount of at least one compound of the invention, or an enantiomer, diastereomer or tautomer thereof, or pharmaceutically acceptable salt of any one of the foregoing.

The actual amount of the compound to be administered in any given case will be determined by a physician taking into account the relevant circumstances, such as the severity of the condition, the age and weight of the subject/patient, the patients general physical condition, the cause of the condition, and the route of administration.

The subject will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back of the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose, any bland fixed oil may be employed, including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100% |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Preservative-free solutions are often formulated in non-resalable containers containing up to about ten, preferably up to about five units doses, where a typical unit dose is from one to about 8 drops, preferably one to about 3 drops. The volume of one drop usually is about 20-35 microliters.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The present invention concerns also processes for preparing the compounds of Formula I. The compounds of Formula I according to the invention can be prepared analogously to conventional methods as understood by the person skilled in the art of synthetic organic chemistry. Synthetic Scheme 1, set forth below, illustrates how the compounds according to the invention can be made.

Scheme 1. Methods of preparing compounds of the invention. The variable groups are as defined for Formula I, unless specifically indicated otherwise. Compound E is the compound of Formula 1, wherein m is 0 or 1, n is 1, 2, 3, 4, 5, 6, 7 or 8, and $R^8$ is not OH). Compound F is the compound of Formula I, wherein m is 1, n is 1, 2, 3, 4, 5, 6, 7 or 8, and $R^8$ is OH. In Intermediate D, m is 0 or 1, n is 1, 2, 3, 4, 5, 6, 7 or 8, and $R^8$ is not OH.

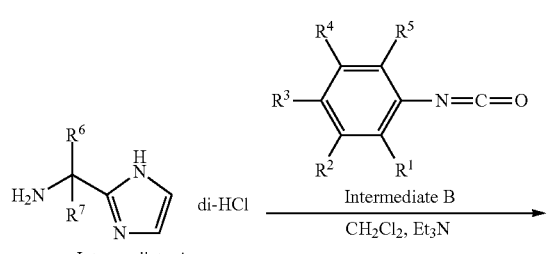

(a)

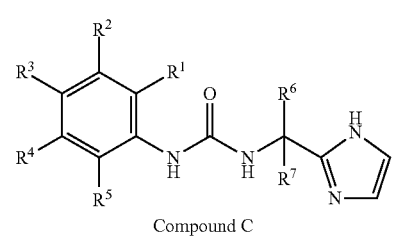

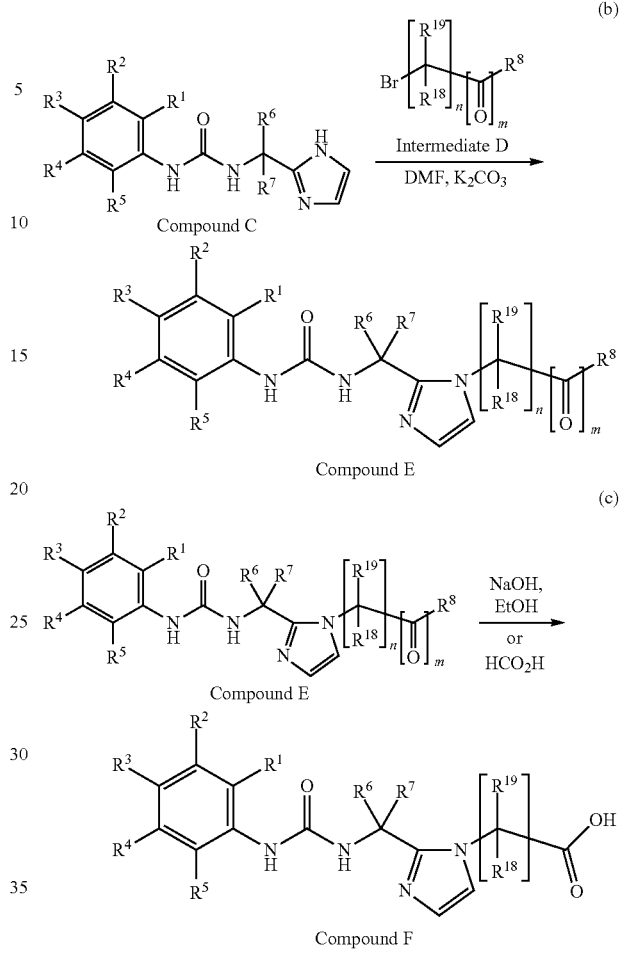

Compounds of Formula I can be prepared as depicted in Scheme 1. In general, Intermediate A is reacted with a substituted phenylisocyanate (Intermediate B) to produce Compound C (Scheme 1a). Compound C can be further modified to provide Compound E or F (Schemes 1b and 1c). For example, Compound C is reacted with Intermediate D to yield Compound E. When Compound E is an imidazole ester, the ester may be hydrolyzed to provide the corresponding carboxylic acid, Compound F. For example, when Compound E is an ethyl ester (i.e., $R^8$ is -OEt), the compound is hydrolyzed with sodium hydroxide to provide the corresponding carboxylic acid. In another example, when Compound E is a tert-butyl ester (i.e., $R^8$ is -OtBu), the compound is reacted with formic acid to yield the non-racemic phenylurea imidazole carboxylic acid.

Those skilled in the art will be able to routinely modify and/or adapt Scheme 1 to synthesize any compounds of the invention that fall within the scope of Formula I.

Each and every feature described herein, and each and every combination of two or more of such features, is included within the scope of the present invention provided that the features included in such a combination are not mutually inconsistent.

Non-limiting embodiments of the invention are as follows.

In embodiment (1), there is provided a compound of Formula I:

Formula I wherein:

each $R^1$, $R^2$, $R^4$ and $R^5$ is independently selected from H, unsubstituted or substituted $C_{1-8}$ alkyl, unsubstituted or substituted $C_{3-8}$ cycloalkyl, unsubstituted or substituted heterocycle, unsubstituted or substituted $C_{6-10}$ aryl, unsubstituted or substituted $C_{3-8}$ cycloalkenyl, halogen, $-S(O)_2NR^{10}R^{11}$, $-NR^{12}R^{13}$, $-S(O)_pR^{14}$, $-C(O)R^{15}$, $-SR^{16}$ and $-OR^{16}$; wherein each said alkyl substituent is independently selected from one or more $R^{20}$; each said cycloalkyl substituent is independently selected from one or more $R^{21}$; each said heterocycle substituent is independently selected from one or more $R^{22}$; each said aryl substituent is independently selected from one or more $R^{23}$; and each said cycloalkenyl substituent is independently selected from one or more $R^{24}$;

$R^3$ is unsubstituted or substituted $C_{1-8}$ alkyl, unsubstituted or substituted $C_{3-8}$ cycloalkyl, unsubstituted or substituted heterocycle, unsubstituted or substituted $C_{6-10}$ aryl, unsubstituted or substituted $C_{3-8}$ cycloalkenyl, halogen, $-S(O)_2NR^{10}R^{11}$, $-NR^{12}R^{13}$, $-S(O)_pR^{14}$, $-C(O)R^{15}$, $-SR^{16}$ or $-OR^{17}$; wherein said alkyl substituent is selected from one or more $R^{20}$; said cycloalkyl substituent is selected from one or more $R^{21}$; said heterocycle substituent is selected from one or more $R^{22}$; said aryl substituent is selected from one or more $R^{23}$; and said cycloalkenyl substituent is selected from one or more $R^{24}$;

$R^6$ is H, or unsubstituted or substituted $C_{1-8}$ alkyl, wherein said alkyl substituent is selected from one or more $R^{25}$;

$R^7$ is H, or unsubstituted or substituted $C_{1-8}$ alkyl, wherein said alkyl substituent is selected from one or more $R^{25}$;

$R^8$ is selected from H, $OR^9$, $NR^{10}R^{11}$, sulfonate, sulfonic acid, phosphonate, phosphonic acid, phosphoric acid and unsubstituted or substituted heterocycle, wherein said heterocycle is selected from tetrazole, imidazole, thiazole, oxazole, triazole, thiophene, pyrazole and pyrrole; and wherein said heterocycle substituent is selected from unsubstituted and substituted $C_{1-8}$ alkyl, wherein said alkyl substituent is selected from OH and halogen;

$R^9$ is H or unsubstituted or substituted $C_{1-8}$ alkyl, wherein said alkyl substituent is selected from OH, halogen, $-OC_{1-8}$ alkyl and $-(OC_{1-8}$ alkylene$)_q$-$OC_{1-8}$ alkyl;

each $R^{10}$ is independently H or unsubstituted $C_{1-8}$ alkyl, or together with $R^{11}$ forms an unsubstituted heterocyclic ring;

each $R^{11}$ is independently H or unsubstituted $C_{1-8}$ alkyl, or together with $R^{10}$ forms an unsubstituted heterocyclic ring;

each $R^{12}$ is independently H or unsubstituted $C_{1-8}$ alkyl;
each $R^{13}$ is independently H or unsubstituted $C_{1-8}$ alkyl;
each $R^{14}$ is independently OH or unsubstituted $C_{1-8}$ alkyl;
each $R^{15}$ is independently H, unsubstituted $C_{1-8}$ alkyl, unsubstituted $C_{3-8}$ cycloalkyl, unsubstituted heterocycle, unsubstituted $C_{6-10}$ aryl or unsubstituted $C_{3-8}$ cycloalkenyl;
each $R^{16}$ is independently H, unsubstituted $C_{1-8}$ alkyl, unsubstituted $C_{3-8}$ cycloalkyl, unsubstituted heterocycle, unsubstituted $C_{6-10}$ aryl or unsubstituted $C_{3-8}$ cycloalkenyl;

$R^{17}$ is H, unsubstituted $C_{1-8}$ alkyl, unsubstituted $C_{3-8}$ cycloalkyl, unsubstituted heterocycle, unsubstituted $C_{6-10}$ aryl or unsubstituted $C_{3-8}$ cycloalkenyl;

each $R^{18}$ is independently H, unsubstituted $C_{1-8}$ alkyl, $-CH_2-(C_{3-8}$ cycloalkyl), $-CH_2-(C_{3-8}$ cycloalkenyl) or benzyl;

each $R^{19}$ is independently H, unsubstituted $C_{1-8}$ alkyl, $-CH_2-(C_{3-8}$ cycloalkyl), $-CH_2-(C_{3-8}$ cycloalkenyl) or benzyl;

each $R^{20}$ is independently selected from halogen, $-OH$, $-CN$, amino, nitro, ether, thioether, unsubstituted $C_{3-8}$ cycloalkyl, unsubstituted $C_{1-6}$ aryl, unsubstituted heterocycle, ester, aldehyde, ketone, carboxylic acid, amide, sulfonamide, sulfonic acid, phosphonic acid and phosphoric acid;

each $R^{21}$, $R^{23}$, $R^{23}$ and $R^{24}$ is independently selected from halogen, $-OH$, $-CN$, amino, nitro, ether, thioether, unsubstituted $C_{1-8}$ alkyl, unsubstituted $C_{3-8}$ cycloalkyl, unsubstituted $C_{1-6}$ aryl, unsubstituted heterocycle, ester, aldehyde, ketone, carboxylic acid, amide, sulfonamide, sulfonic acid, phosphonic acid and phosphoric acid;

each $R^{25}$ is independently selected from halogen, hydroxyl, amino, ether, thioether, unsubstituted $C_{3-8}$ cycloalkyl, unsubstituted $C_{3-8}$ cycloalkenyl, unsubstituted $C_{1-6}$ aryl, unsubstituted heterocycle, carboxylic acid, amide, sulfonic acid, phosphonic acid and phosphoric acid;

m is 0 or 1;
n is 0, 1, 2, 3, 4, 5, 6, 7 or 8;
each p is independently 1 or 2; and
q is 1, 2, 3, 4, 5 or 6;
or a tautomer thereof;
or pharmaceutically acceptable salt of any one of the foregoing;
provided that:
(a) when m is 1, then n is not 0;
(b) when m is 1, then $R^6$ is $OR^9$ or $NR^{10}R^{11}$;
(c) when m is 0 and n is 0, then $R^8$ is H; and
(d) when m is 0, and n is not 0, then $R^6$ is not H.

In embodiment (2), there is provided the compound of embodiment (1), wherein:

each $R^1$, $R^2$, $R^4$ and $R^5$ is independently selected from H, unsubstituted or substituted $C_{1-8}$ alkyl, halogen, $-S(O)_2NR^{10}R^{11}$, $NR^{12}R^{13}$, $-S(O)_pR^{14}$, $-C(O)R^{15}$, $-SR^{16}$ and $-OR^{16}$; wherein each said alkyl substituent is independently selected from one or more $R^{20}$;

$R^3$ is unsubstituted or substituted $C_{1-8}$ alkyl, halogen, $-S(O)_2NR^{10}R^{11}$, $-NR^{12}R^{13}$, $-S(O)_pR^{14}$, $-C(O)R^{15}$, $-SR^{16}$ or $-OR^{17}$; wherein said alkyl substituent is selected from one or more $R^{20}$;

$R^6$ is H, or unsubstituted or substituted $C_{1-8}$ alkyl, wherein said alkyl substituent is selected from one or more $R^{25}$;

$R^7$ is H, or unsubstituted or substituted $C_{1-8}$ alkyl, wherein said alkyl substituent is selected from one or more $R^{25}$;

$R^8$ is selected from H, $OR^9$, $NR^{10}R^{11}$, sulfonate, sulfonic acid, phosphonate, phosphonic acid, phosphoric acid and unsubstituted or substituted heterocycle, wherein said heterocycle is selected from tetrazole, imidazole, thiazole, oxazole, triazole, thiophene, pyrazole and pyrrole; and wherein said heterocycle substituent is selected from unsubstituted and substituted $C_{1-8}$ alkyl, wherein said alkyl substituent is selected from OH and halogen;

$R^9$ is H or unsubstituted or substituted $C_{1-8}$ alkyl, wherein said alkyl substituent is selected from OH, halogen, $-OC_{1-8}$ alkyl and $-(OC_{1-8}$ alkylene$)_q$-$OC_{1-8}$ alkyl;

each $R^{10}$ is independently H, unsubstituted $C_{1-8}$ alkyl, or together with $R^{11}$ forms a heterocyclic ring;

each $R^{11}$ is independently H, unsubstituted $C_{1-8}$ alkyl, or together with $R^{10}$ forms a heterocyclic ring;

each $R^{12}$ is independently H or unsubstituted $C_{1-8}$ alkyl;
each $R^{13}$ is independently H or unsubstituted $C_{1-8}$ alkyl;
each $R^{14}$ is independently OH or unsubstituted $C_{1-8}$ alkyl;
each $R^{15}$ is independently H, unsubstituted $C_{1-8}$ alkyl, unsubstituted $C_{3-8}$ cycloalkyl, unsubstituted heterocycle, unsubstituted $C_{6-10}$ aryl or unsubstituted $C_{3-8}$ cycloalkenyl;
each $R^{16}$ is independently H, unsubstituted $C_{1-8}$ alkyl, unsubstituted $C_{3-8}$ cycloalkyl, unsubstituted heterocycle, unsubstituted $C_{6-10}$ aryl or unsubstituted $C_{3-8}$ cycloalkenyl;
$R^{17}$ is H or unsubstituted $C_{1-8}$ alkyl;
each $R^{18}$ is H or unsubstituted $C_{1-8}$ alkyl;
each $R^{19}$ is H or unsubstituted $C_{1-8}$ alkyl;
each $R^{20}$ is independently selected from halogen, —OH, —CN, amino, nitro, ether, thioether, unsubstituted $C_{3-8}$ cycloalkyl, unsubstituted $C_{1-6}$ aryl, unsubstituted heterocycle, ester, aldehyde, ketone, carboxylic acid, amide, sulfonamide, sulfonic acid, phosphonic acid and phosphoric acid;
each $R^{25}$ is independently selected from halogen, hydroxyl, amino, ether, thioether, unsubstituted $C_{3-8}$ cycloalkyl, unsubstituted $C_{3-8}$ cycloalkenyl, unsubstituted $C_{1-6}$ aryl, unsubstituted heterocycle, carboxylic acid, amide, sulfonic acid, phosphonic acid and phosphoric acid;
m is 0 or 1;
n is 0, 1 or 2;
each p is independently 1 or 2; and
q is 1, 2, 3, 4, 5 or 6;
or a tautomer thereof;
or pharmaceutically acceptable salt of any one of the foregoing;
provided that:
    (a) when m is 1, then n is not 0;
    (b) when m is 1, then $R^6$ is $OR^9$ or $NR^{10}R^{11}$;
    (c) when m is 0 and n is 0, then $R^8$ is H; and
    (d) when m is 0, and n is not 0, then $R^8$ is not H.

In embodiment (3), there is provided the compound of embodiment (1) or (2), wherein:
    each $R^1$, $R^2$, $R^4$ and $R^5$ is independently selected from H, unsubstituted or substituted $C_{1-8}$ alkyl, and halogen; wherein each said alkyl substituent is independently selected from one or more $R^{20}$;
    $R^3$ is unsubstituted or substituted $C_{1-8}$ alkyl, halogen or —$OR^{17}$; wherein said alkyl substituent is selected from one or more $R^{20}$;
    $R^6$ is H, or unsubstituted or substituted $C_{1-8}$ alkyl, wherein said alkyl substituent is selected from one or more $R^{25}$;
    $R^7$ is H, or unsubstituted or substituted $C_{1-8}$ alkyl, wherein said alkyl substituent is selected from one or more $R^{25}$;
    $R^8$ is selected from H, $OR^9$, $NR^{10}R^{11}$, sulfonate, sulfonic acid, phosphonate, phosphonic acid, phosphoric acid and unsubstituted or substituted heterocycle, wherein said heterocycle is selected from tetrazole, imidazole, thiazole, oxazole, triazole, thiophene, pyrazole and pyrrole; and wherein said heterocycle substituent is selected from unsubstituted and substituted $C_{1-8}$ alkyl, wherein said alkyl substituent is selected from OH and halogen;
    $R^9$ is H or unsubstituted or substituted $C_{1-8}$ alkyl, wherein said alkyl substituent is selected from OH, halogen, —$OC_{1-8}$ alkyl and —$(OC_{1-3}$ alkylene$)_q$-$OC_{1-3}$ alkyl (e.g., —$OCH_2CH_2$—$OCH_3$, or —$(OCH_2CH_2)_2$—$OCH_2CH_3$);
    $R^{10}$ is H or unsubstituted $C_{1-8}$ alkyl;
    $R^{11}$ is H or unsubstituted $C_{1-8}$ alkyl;
    $R^{17}$ is H or unsubstituted $C_{1-8}$ alkyl;
    each $R^{18}$ is H or unsubstituted $C_{1-8}$ alkyl;
    each $R^{19}$ is H or unsubstituted $C_{1-8}$ alkyl;
    each $R^{20}$ is independently selected from halogen, —OH, —CN, amino, nitro, ether, thioether, unsubstituted $C_{3-8}$ cycloalkyl, unsubstituted $C_{1-6}$ aryl, unsubstituted heterocycle, ester, aldehyde, ketone, carboxylic acid, amide, sulfonamide, sulfonic acid, phosphonic acid and phosphoric acid;
    each $R^{25}$ is independently selected from halogen, hydroxyl, amino, ether, thioether, unsubstituted $C_{3-8}$ cycloalkyl, unsubstituted $C_{3-8}$ cycloalkenyl, unsubstituted $C_{1-6}$ aryl, unsubstituted heterocycle, carboxylic acid and amide;
    m is 0 or 1;
    n is 0, 1 or 2; and
    q is 1, 2, 3, 4, 5 or 6;
or a tautomer thereof;
or pharmaceutically acceptable salt of any one of the foregoing;
provided that:
    (a) when m is 1, then n is not 0;
    (b) when m is 1, then $R^8$ is $OR^9$ or $NR^{10}R^{11}$;
    (c) when m is 0 and n is 0, then $R^8$ is H; and
    (d) when m is 0, and n is not 0, then $R^8$ is not H.

In embodiment (4), there is provided the compound of any one of embodiments (1), (2) or (3), wherein:
    each $R^1$, $R^2$, $R^4$ and $R^5$ is independently selected from H, unsubstituted $C_{1-8}$ alkyl, $C_{1-8}$ haloalkyl and halogen;
    $R^3$ is unsubstituted $C_{1-8}$ alkyl, $C_{1-8}$ haloalkyl, halogen, or —$OR^{17}$;
    $R^6$ is H, or unsubstituted or substituted $C_{1-8}$ alkyl, wherein said alkyl substituent is selected from one or more $R^{25}$;
    $R^7$ is H;
    $R^8$ is selected from H, $OR^9$, $NR^{10}R^{11}$, sulfonate, sulfonic acid, phosphonate, phosphonic acid, phosphoric acid and unsubstituted or substituted heterocycle, wherein said heterocycle is selected from tetrazole, imidazole, thiazole, oxazole, triazole, thiophene, pyrazole and pyrrole; and wherein said heterocycle substituent is selected from unsubstituted and substituted $C_{1-8}$ alkyl, wherein said alkyl substituent is selected from OH and halogen;
    $R^9$ is H or unsubstituted or substituted $C_{1-8}$ alkyl, wherein said alkyl substituent is selected from OH, halogen, —$OC_{1-8}$ alkyl and —$(OC_{1-3}$ alkylene$)_q$-$OC_{1-3}$ alkyl;
    $R^{10}$ is H or unsubstituted $C_{1-8}$ alkyl;
    $R^{11}$ is H or unsubstituted $C_{1-8}$ alkyl;
    $R^{17}$ is unsubstituted $C_{1-8}$ alkyl;
    each $R^{18}$ is H or unsubstituted $C_{1-8}$ alkyl;
    each $R^{19}$ is H;
    $R^{25}$ is independently selected from halogen, hydroxyl, amino, ether, thioether, unsubstituted $C_{3-8}$ cycloalkyl, unsubstituted $C_{3-8}$ cycloalkenyl, unsubstituted $C_{1-8}$ aryl, unsubstituted heterocycle, carboxylic acid and amide;
    m is 0 or 1;
    n is 0, 1 or 2; and
    q is 1, 2 or 3;
or a tautomer thereof;
or pharmaceutically acceptable salt of any one of the foregoing;
provided that:
    (a) when m is 1, then n is not 0;
    (b) when m is 1, then $R^8$ is $OR^9$ or $NR^{10}R^{11}$;
    (c) when m is 0 and n is 0, then $R^8$ is H; and
    (d) when m is 0, and n is not 0, then $R^8$ is not H.

In embodiment (5), there is provided the compound of any one of embodiments (1) through (4), wherein:
    each $R^1$, $R^2$, $R^4$ and $R^5$ is independently selected from H, unsubstituted $C_{1-8}$ alkyl, and halogen;
    $R^3$ is $C_{1-8}$ haloalkyl, halogen, or —$OR^{17}$;

$R^6$ is H or unsubstituted $C_{1-8}$ alkyl;
$R^7$ is H;
$R^8$ is selected from H, $OR^9$, $NR^{10}R^{11}$, sulfonate, sulfonic acid, phosphonate, phosphonic acid, phosphoric acid and unsubstituted or substituted heterocycle, wherein said heterocycle is selected from tetrazole, imidazole, thiazole, oxazole, triazole, thiophene, pyrazole and pyrrole; and wherein said heterocycle substituent is selected from unsubstituted and substituted $C_{1-8}$ alkyl, wherein said alkyl substituent is selected from OH and halogen;
$R^9$ is H or unsubstituted $C_{1-8}$ alkyl;
$R^{10}$ is H or unsubstituted $C_{1-8}$ alkyl;
$R^{11}$ is H or unsubstituted $C_{1-8}$ alkyl;
$R^{17}$ is unsubstituted $C_{1-8}$ alkyl;
each $R^{18}$ is H or unsubstituted $C_{1-8}$ alkyl;
each $R^{19}$ is H;
m is 0 or 1; and
n is 0, 1 or 2;
or a tautomer thereof;
or pharmaceutically acceptable salt of any one of the foregoing;
provided that:
(a) when m is 1, then n is not 0;
(b) when m is 1, then $R^8$ is $OR^9$ or $NR^{10}R^{11}$;
(c) when m is 0 and n is 0, then $R^8$ is H; and
(d) when m is 0, and n is not 0, then $R^8$ is not H.

In embodiment (6), there is provided the compound of any one of embodiments (1) through (5), wherein:
$R^1$ is H or halogen;
$R^2$ is H;
$R^3$ is $C_{1-3}$ haloalkyl, halogen or $—OR^{17}$;
$R^4$ is H;
$R^5$ is H or halogen;
$R^6$ is H or unsubstituted $C_{1-3}$ alkyl;
$R^7$ is H;
$R^8$ is selected from H, $OR^9$, $NR^{10}R^{11}$, sulfonate, sulfonic acid, phosphonate, phosphonic acid, phosphoric acid and unsubstituted or substituted heterocycle, wherein said heterocycle is selected from tetrazole, imidazole, thiazole, oxazole, triazole, thiophene, pyrazole and pyrrole; and wherein said heterocycle substituent is selected from unsubstituted and substituted $C_{1-8}$ alkyl, wherein said alkyl substituent is selected from OH and halogen;
$R^9$ is H or unsubstituted $C_{1-4}$ alkyl;
$R^{10}$ is H or unsubstituted $C_{1-3}$ alkyl;
$R^{11}$ is H or unsubstituted $C_{1-3}$ alkyl;
$R^{17}$ is unsubstituted $C_{1-3}$ alkyl;
each $R^{18}$ is H or unsubstituted $C_{1-3}$ alkyl;
each $R^{19}$ is H;
m is 0 or 1; and
n is 0, 1 or 2;
or a tautomer thereof;
or pharmaceutically acceptable salt of any one of the foregoing;
provided that:
(a) when m is 1, then n is not 0;
(b) when m is 1, then $R^8$ is $OR^9$ or $NR^{10}R^{11}$;
(c) when m is 0 and n is 0, then $R^8$ is H; and
(d) when m is 0, and n is not 0, then $R^8$ is not H.

In embodiment (7), there is provided the compound of embodiment (1), wherein:
each $R^{20}$ is independently selected from halogen, —OH, —CN, nitro, $—NR^xR^y$, $—OC_{1-8}$ alkyl, $—SC_{1-8}$ alkyl, $—OC(O)C_{1-8}$ alkyl, $—C(O)OC_{1-8}$alkyl, carboxylic acid, $—C(O)C_{1-8}$alkyl, $—C(O)N(R^x)(R^y)$, $—NR^xC(O)R^y$, $—S(O)_2N(R^x)(R^y)$, $—NR^xS(O)_2R^y$, sulfonic acid, phosphonic acid and phosphoric acid; wherein each $R^x$ and $R^y$ is independently selected from H and unsubstituted $C_{1-8}$ alkyl;
each $R^{21}$, $R^{22}$, $R^{23}$ and $R^{24}$ is independently selected from halogen, —OH, —CN, nitro, $—NR^xR^y$, $—OC_{1-8}$ alkyl, $—SC_{1-8}$ alkyl, unsubstituted $C_{1-8}$ alkyl, $—OC(O)C_{1-8}$ alkyl, $—C(O)OC_{1-8}$ alkyl, carboxylic acid, $—C(O)C_{1-8}$ alkyl, $—C(O)N(R^x)(R^y)$, $—NR^xC(O)R^y$, $—S(O)_2N(R^x)(R^y)$, $—NR^xS(O)_2R^y$, sulfonic acid, phosphonic acid and phosphoric acid; wherein each $R^x$ and $R^y$ is independently selected from H and unsubstituted $C_{1-8}$ alkyl; and
each $R^{25}$ is independently selected from halogen, —OH, $—NR^xR^y$, $OC_{1-8}$ alkyl, $—SC_{1-8}$ alkyl, carboxylic acid, unsubstituted $C_{3-8}$ cycloalkyl, unsubstituted $C_{3-8}$ cycloalkenyl, unsubstituted $C_{1-8}$ aryl, unsubstituted heterocycle, $C(O)N(R^x)(R^y)$, $—NR^xC(O)R^y$, sulfonic acid, phosphonic acid and phosphoric acid; wherein each $R^x$ and $R^y$ is independently selected from H and unsubstituted $C_{1-8}$ alkyl.

In embodiment (8), there is provided a compound of embodiment (1), wherein:
each $R^{20}$ is independently selected from halogen, —OH, —CN, nitro, $—NR^xR^y$, $—OC_{1-3}$ alkyl, $—SC_{1-3}$ alkyl, $—OC(O)C_{1-3}$ alkyl, $—C(O)OC_{1-3}$ alkyl, carboxylic acid, $—C(O)C_{1-3}$ alkyl, $—C(O)N(R^x)(R^y)$, $—NR^xC(O)R^y$, $—S(O)_2N(R^x)(R^y)$, $—NR^xS(O)_2R^y$, sulfonic acid, phosphonic acid and phosphoric acid; wherein each $R^x$ and $R^y$ is independently selected from H and unsubstituted $C_{1-3}$ alkyl;
each $R^{21}$, $R^{22}$, $R^{23}$ and $R^{24}$ is independently selected from halogen, —OH, —CN, nitro, $—NR^xR^y$, $—OC_{1-3}$ alkyl, $—SC_{1-3}$ alkyl, unsubstituted $C_{1-3}$ alkyl, $—OC(O)C_{1-3}$ alkyl, $—C(O)OC_{1-3}$ alkyl, carboxylic acid, $—C(O)C_{1-3}$ alkyl, $—C(O)N(R^x)(R^y)$, $—NR^xC(O)R^y$, $—S(O)_2N(R^x)(R^y)$, $—NR^xS(O)_2R^y$, sulfonic acid, phosphonic acid and phosphoric acid; wherein each $R^x$ and $R^y$ is independently selected from H and unsubstituted $C_{1-3}$ alkyl; and
each $R^{25}$ is independently selected from halogen, —OH, $—NR^xR^y$, $OC_{1-3}$ alkyl, $—SC_{1-3}$ alkyl, carboxylic acid, unsubstituted $C_{3-8}$ cycloalkyl, unsubstituted $C_{3-8}$ cycloalkenyl, unsubstituted $C_{1-6}$ aryl, unsubstituted heterocycle, $C(O)N(R^x)(R^y)$, $—NR^xC(O)R^y$, sulfonic acid, phosphonic acid and phosphoric acid; wherein each $R^x$ and $R^y$ is independently selected from H and unsubstituted $C_{1-3}$ alkyl.

In embodiment (9), there is provided a compound of any one of embodiments (1) through (3), wherein:
each $R^{20}$ is independently selected from halogen, —OH, —CN, nitro, $—NR^xR^y$, $—OC_{1-8}$ alkyl, $—SC_{1-8}$ alkyl, $—OC(O)C_{1-8}$ alkyl, $—C(O)OC_{1-8}$alkyl, carboxylic acid, $—C(O)C_{1-8}$alkyl, $—C(O)N(R^x)(R^y)$, $—NR^xC(O)R^y$, $—S(O)_2N(R^x)(R^y)$, $—NR^xS(O)_2R^y$, sulfonic acid, phosphonic acid and phosphoric acid; wherein each $R^x$ and $R^y$ is independently selected from H and unsubstituted $C_{1-8}$ alkyl.

In embodiment (10), there is provided a compound of any one of embodiments (1) through (3), wherein:
each $R^{20}$ is independently selected from halogen, —OH, —CN, nitro, $—NR^xR^y$, $—OC_{1-3}$ alkyl, $—SC_{1-3}$ alkyl, $—OC(O)C_{1-3}$ alkyl, $—C(O)OC_{1-3}$ alkyl, carboxylic acid, $—C(O)C_{1-3}$ alkyl, $—C(O)N(R^x)(R^y)$, $—NR^xC(O)R^y$, $—S(O)_2N(R^x)(R^y)$, $—NR^xS(O)_2R^y$, sulfonic acid, phosphonic acid and phosphoric acid; wherein each $R^x$ and $R^y$ is independently selected from H and unsubstituted $C_{1-3}$ alkyl.

In embodiment (11), there is provided a compound of any one of embodiments (1) through (4) and (9), wherein:
each $R^{25}$ is independently selected from halogen, —OH, $—NR^xR^y$, $OC_{1-8}$ alkyl, $—SC_{1-8}$ alkyl, carboxylic acid, unsubstituted $C_{3-8}$ cycloalkyl, unsubstituted $C_{3-8}$ cycloalkenyl, unsubstituted $C_{1-6}$ aryl, unsubstituted heterocycle, $C(O)N(R^x)(R^y)$, $—NR^xC(O)R^y$, sulfonic acid, phosphonic acid and phosphoric acid; wherein each $R^x$ and $R^y$ is independently selected from H and unsubstituted $C_{1-8}$ alkyl.

In embodiment (12), there is provided a compound of embodiment (1) through (4) and (10), wherein:

each $R^{25}$ is independently selected from halogen, —OH, —$NR^xR^y$, $OC_{1-3}$ alkyl, —$SC_{1-3}$ alkyl, carboxylic acid, unsubstituted $C_{3-8}$ cycloalkyl, unsubstituted $C_{3-8}$ cycloalkenyl, unsubstituted $C_{1-6}$ aryl, unsubstituted heterocycle, $C(O)N(R^x)(R^y)$, —$NR^xC(O)R^y$, sulfonic acid, phosphonic acid and phosphoric acid; wherein each $R^x$ and $R^y$ is independently selected from H and unsubstituted $C_{1-3}$ alkyl.

In embodiment (13), there is provided a compound of any one of embodiments (1) through (4), wherein:

each said alkyl substituent is selected from halogen, —OH, —CN, nitro, —$NR^xR^y$, —$OC_{1-3}$ alkyl, —$OC(O)C_{1-3}$ alkyl, —$C(O)OC_{1-3}$ alkyl and carboxylic acid; wherein each $R^x$ and $R^y$ is independently selected from H and unsubstituted $C_{1-3}$ alkyl;

In embodiment (14), there is provided a compound of any one of embodiments (1) through (4), wherein each said alkyl substituent is a halogen.

In embodiment (15), there is provided the compound of any one of embodiments (1) through (14), wherein $R^6$ is selected from H, $OR^9$ and $NR^{10}R^{11}$.

In embodiment (16), there is provided the compound of any one of embodiments (1) through (15), wherein:
m is 0;
n is 0; and
R is H.

In embodiment (17), there is provided the compound of any one of embodiments (1) through (15), wherein:
m is 1;
n is 1;
$R^8$ is $OR^9$, wherein $R^9$ is unsubstituted $C_{1-8}$ alkyl;
$R^{18}$ is H; and
$R^{19}$ is H.

In embodiment (18), there is provided the compound of any one of embodiments (1) through (15), wherein:
m is 1;
n is 1;
$R^8$ is $OR^9$, wherein $R^9$ is H;
$R^{18}$ is H; and
$R^{19}$ is H.

In embodiment (19), there is provided the compound of any one of embodiments (1) through (15), wherein:
m is 1;
n is 1;
$R^8$ is $OR^9$, wherein $R^9$ is unsubstituted $C_{1-8}$ alkyl;
$R^{18}$ is unsubstituted $C_{1-8}$ alkyl; and
$R^{19}$ is H.

In embodiment (20), there is provided the compound of any one of embodiments (1) through (15), wherein:
m is 1;
n is 1;
$R^8$ is $OR^9$, wherein $R^9$ is H;
$R^{18}$ is unsubstituted $C_{1-8}$ alkyl; and
$R^{19}$ is H.

In embodiment (21), there is provided the compound of any one of embodiments (1) through (15), wherein:
m is 1;
n is 2;
$R^8$ is $NR^{10}R^{11}$, wherein $R^{10}$ is H or unsubstituted $C_{1-8}$ alkyl, and $R^{11}$ is H or unsubstituted or substituted $C_{1-8}$ alkyl;
each $R^{18}$ is H; and
each $R^{19}$ is H.

In embodiment (22), there is provided the compound of any one of embodiments (1) through (15), wherein:

m is 1;
n is 2;
$R^8$ is $OR^9$, wherein $R^9$ is unsubstituted $C_{1-8}$ alkyl;
each $R^{18}$ is H; and
each $R^{19}$ is H.

In embodiment (23), there is provided the compound of any one of embodiments (1) through (15), wherein:
m is 1;
n is 2;
$R^8$ is $OR^9$, wherein $R^9$ is H;
each $R^{18}$ is H; and
each $R^{19}$ is H.

In embodiment (24), there is provided the compound of any one of embodiments (1) through (15), wherein:
m is 0;
n is 2;
$R^8$ is $OR^9$, wherein $R^9$ is H;
each $R^{18}$ is H; and
each $R^{19}$ is H.

In embodiment (25), there is provided the compound of any one of embodiments (1) through (24), provided that $R^6$ is not H.

In embodiment (26), there is provided the compound of any one of embodiments (1) through (24), provided that $R^6$ is not H, $R^{18}$ is H, and $R^{19}$ is H.

In embodiment (27), there is provided a compound of any one of embodiments (1) through (26), wherein each $C_{1-8}$ alkyl is independently optionally replaced with $C_{1-4}$alkyl, and when unsubstituted, each $C_{1-4}$ alkyl is independently selected from methyl, ethyl, n-propyl, isopropyl, butyl, tert-butyl, isobutyl and sec-butyl.

In embodiment (28), there is provided a compound selected from:

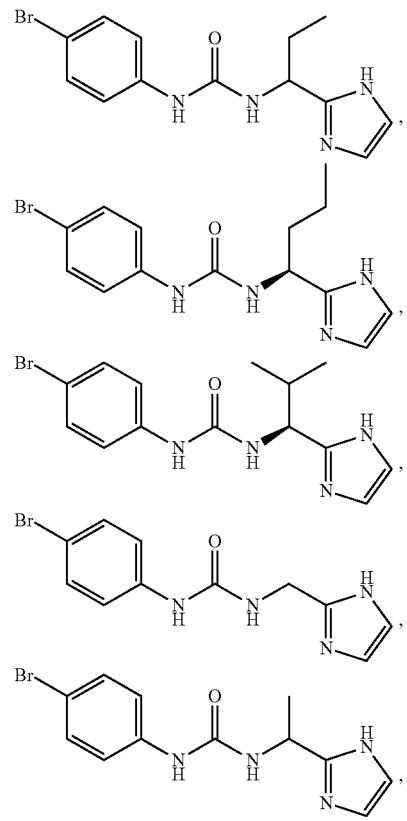

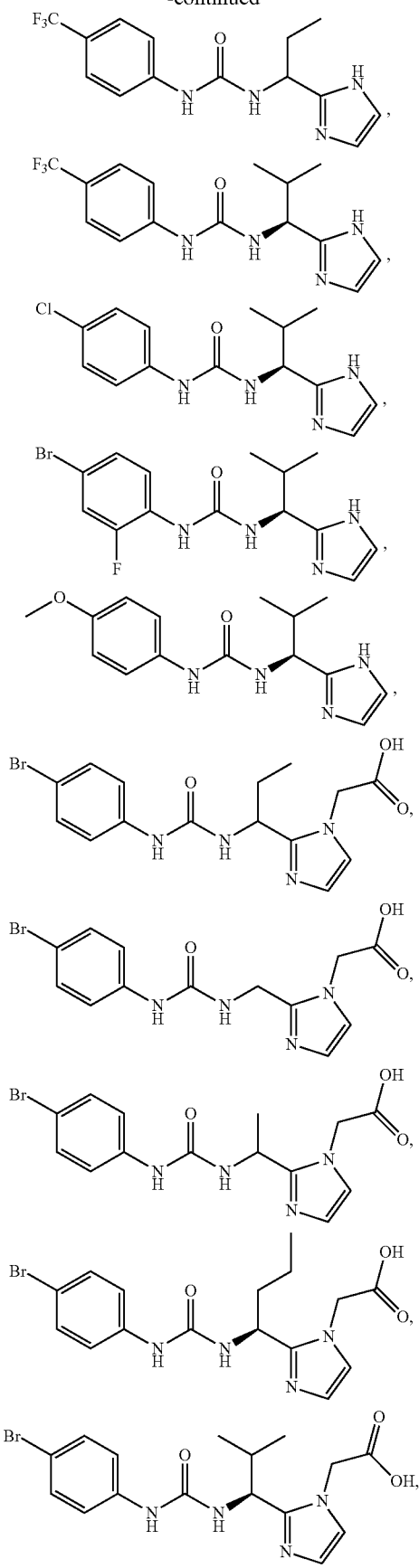
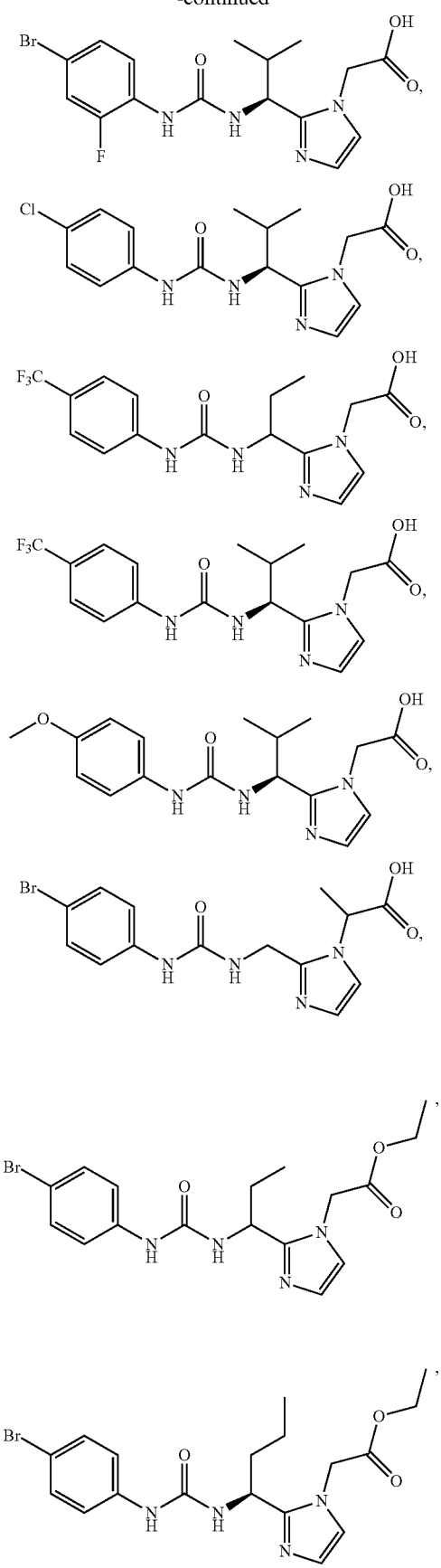

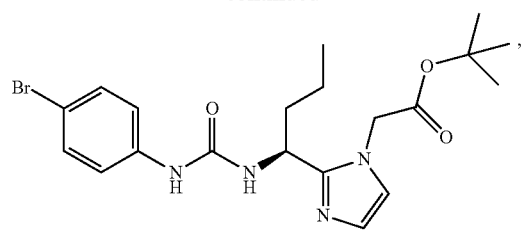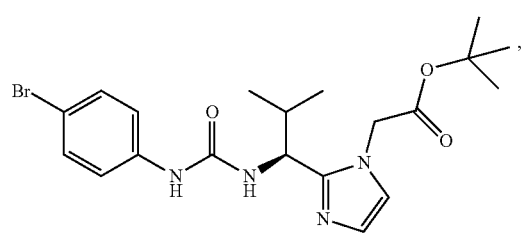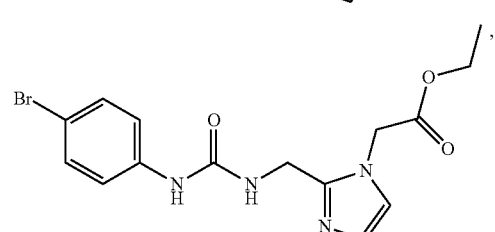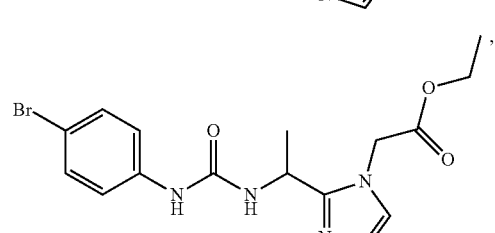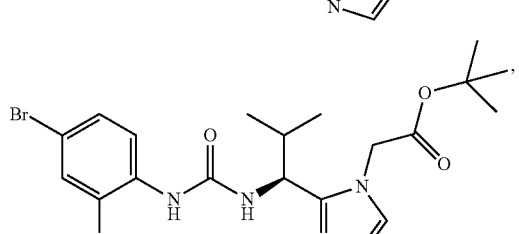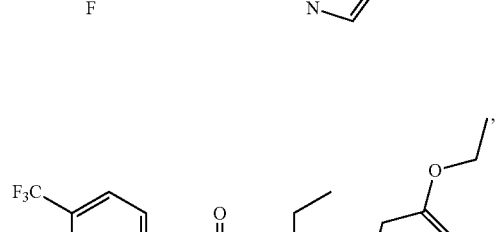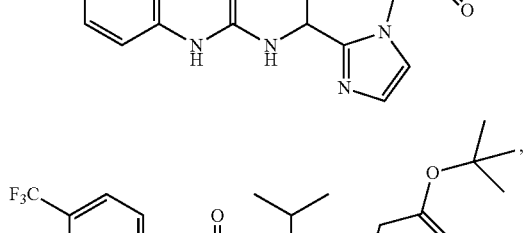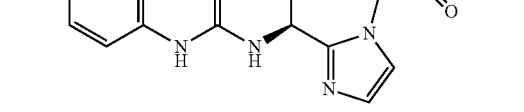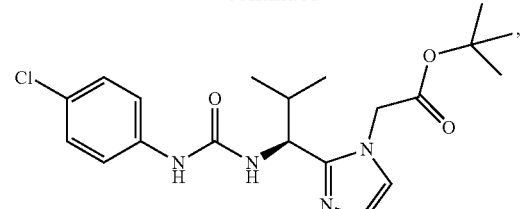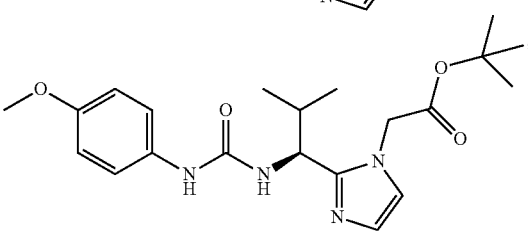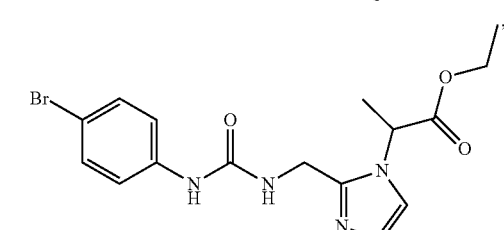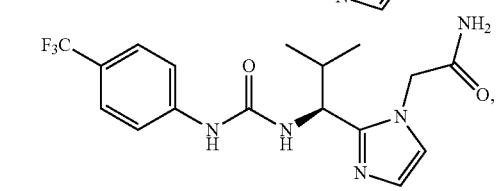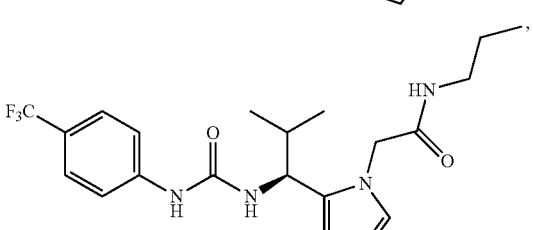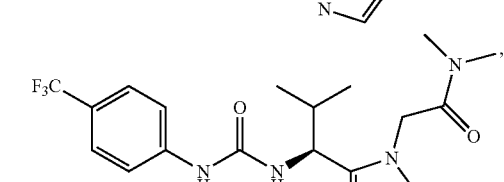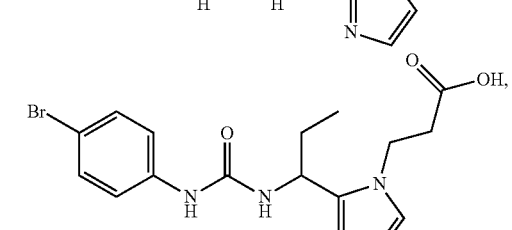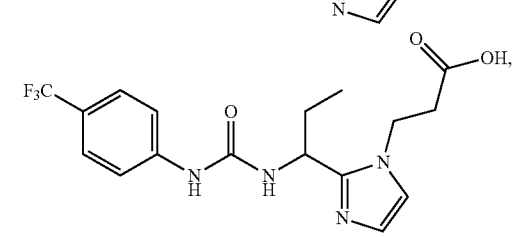

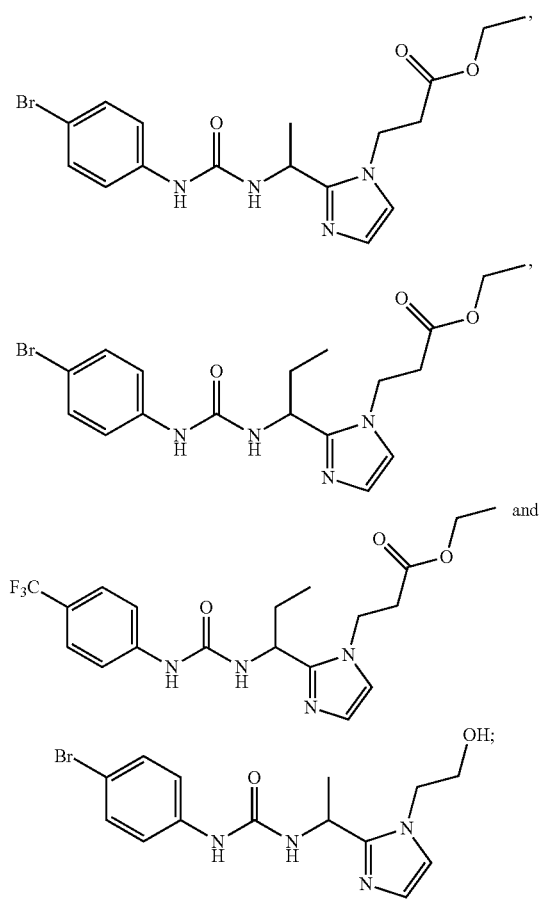

and tautomers thereof;
and pharmaceutically acceptable salts of any of the foregoing.

In embodiment (29), there is provided a pharmaceutical composition comprising as active ingredient a therapeutically effective amount of a compound according to any one of embodiments (1) through (28), and a pharmaceutically acceptable carrier.

In embodiment (30), there is provided a compound or pharmaceutical composition according to any one of embodiments (1) through (29) for use in treating an inflammatory disease or condition in a subject in need of such treatment.

In embodiment (31), there is provided a compound or pharmaceutical composition according to any one of embodiments (1) through (29) for use in treating an inflammatory disease or condition in a subject in need of such treatment, wherein the disease or condition is an ocular inflammatory disease or condition, or a dermal inflammatory disease or condition.

In embodiment (32), there is provided a method of treating a disease or condition in a subject in need of such treatment, the method comprising administering a therapeutically effective amount of a compound or pharmaceutical composition according to any one of embodiments (1) through (29) to the subject, thereby treating the disease or condition.

In embodiment (33), there is provided the method of embodiment (32), wherein the disease or condition is (a) an ocular inflammatory disease or condition; or (b) a dermal inflammatory disease or condition.

In embodiment (34), there is provided the method of embodiment (32) or (33), wherein the disease or condition is an ocular inflammatory disease or condition;

in a further embodiment, the inflammatory disease or condition is selected from: age-related macular degeneration, wet macular degeneration, dry macular degeneration, uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity, acute macular neuroretinopathy, central serous chorioretinopathy, cystoid macular edema, and diabetic macular edema; infectious keratitis, herpetic keratitis, corneal angiogenesis, lymphangiogenesis, retinitis, and choroiditis such as acute multifocal placoid pigment epitheliopathy, Behcets disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi-and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coats disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, conditions caused by laser, conditions caused by photodynamic therapy, photocoagulation, hypoperfusion during surgery, radiation retinopathy, bone marrow transplant retinopathy, post-surgical corneal wound healing or inflammation, and post-cataract surgical inflammation; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, corneal wound healing burns, rosacea, atopic dermatitis, acne, psoriasis, seborrheic dermatitis, actinic keratoses, viral warts, photoaging rheumatoid arthritis and related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the retinal pigment epithelium.

In embodiment (35), there is provided the method of embodiment (34), wherein the ocular inflammatory disease or condition is selected from: dry eye, a post-surgical corneal wound, post-surgical corneal inflammation, and post-cataract surgical inflammation.

In embodiment (36), there is provided the method of embodiment (32) or (33), wherein the disease or condition is a dermal inflammatory disease or condition;

in a further embodiment, the dermal inflammatory disease or condition is selected from: a dermal wound, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation, alopecia, scarring and non-scarring forms.

In embodiment (37), there is provided the method of embodiment (36), wherein the dermal inflammatory disease or condition is psoriasis or rosacea.

In embodiment (38), there is provided the method of any one of embodiments (32) through (37), wherein the subject is a human.

In embodiment (39), there is provided the method of embodiment (32), wherein the disease or condition is selected from stroke, coronary artery disease, an obstructive airway disease, an HIV-mediated retroviral infection, a cardiovascular disorder such as coronary artery disease, neuroinflammation, a neurological disorder, pain, an immunological disorder, rheumatoid arthritis, asthma, an allergic disorder, systemic lupus erythematosus, Alzheimer's disease, arthritis, sepsis, inflammatory bowel disease, cachexia and angina pectoris.

In embodiment (40), there is provided the method of embodiment (39), wherein the disease or condition is rheumatoid arthritis.

In embodiment (41), there is provided the method of embodiment (39) or (40), wherein the subject is a human.

The following Examples illustrate how compounds according to the invention can be made, and provide details of certain specific chemical transformations. The Examples are for illustrative purposes only and are not intended, nor should they be construed, as limiting the invention in any manner. Those skilled in the art will be able to routinely modify and/or adapt the Examples to synthesize any compound of the invention covered by Formula I, and will appreciate that variations and modifications of the Examples can be made without exceeding the spirit or scope of the invention.

All reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates were prepared according to published procedures.

Compound names were generated with ACDLab version 12.5; some intermediate and reagent names used in the Examples were generated with software such as Chem Bio Draw Ultra version 12.0, ACDLab version 12.5 or Auto Nom 2000 from MDL ISIS Draw 2.5 SPI.

In general, characterization of the compounds was performed using NMR spectroscopy. NMR spectra were recorded on a 300 or 600 MHz Varian NMR spectrometer and acquired at room temperature. Chemical shifts are given in ppm referenced either to internal TMS or to the solvent signal.

Usually, the compounds of the invention were purified by medium pressure liquid chromatography, unless noted otherwise.

Example 1

Compound 1

1-(4-Bromophenyl)-3-[1-(1H-imidazol-2-yl)propyl]urea

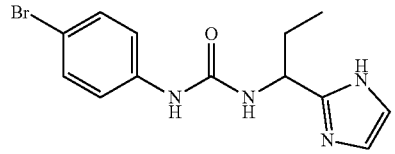 [SMILES: CCC(NC(=O)Nc1ccc(Br)cc1)c1ncc[nH]1]

To a solution of 1-(1H-imidazol-2-yl)propan-1-amine dihydrochloride (23 mg, 0.12 mmol) and 2 mL of pyridine at 25° C. was added 4-bromo-phenyl isocyanate (23 mg, 0.12 mmol). The resulting mixture was stirred at 25° C. for 1 hour. The mixture was quenched with saturated $NH_4Cl$ (2 mL), and the product was extracted with ethyl acetate (10 mL). The layers were separated, and the organic layer was washed with water, brine, dried over $Na_2SO_4$, filtered, and the filtrate was concentrated under reduced pressure. The residue was purified by medium pressure liquid chromatography on silica gel using 100% ethyl acetate to yield Compound 1 as a white solid.

$^1$H NMR (DMSO-d6, 600 MHz) δ ppm: 8.76 (s, 1H), 7.37 (q, J=9.0 Hz, 4H), 6.92 (br. s., 1H), 6.58 (d, J=8.1 Hz, 1H), 4.72-4.78 (m, 1H), 1.83 (dquin, J=13.8, 7.1 Hz, 1H), 1.73 (dquin, J=13.8, 7.1 Hz, 1H), 0.78 (t, J=7.4 Hz, 3H).

Compounds 2 through 6 and 28 through 31 were prepared from the corresponding amino imidazole in a similar manner to the procedure described in Example 1 for Compound 1. The results are tabulated in Table 1.

TABLE 1

| Comp. No. | IUPAC name Structure | ¹H NMR δ (ppm), form and optical rotation |
|---|---|---|
| 2 | 1-(4-Bromophenyl)-3-[(1S)-1-(1H-imidazol-2-yl)butyl]urea | ¹H NMR (CD₃OD, 600 MHz) δ: 7.46 (s, 2H), 7.35-7.39 (m, 2H), 7.29-7.34 (m, 2H), 5.01-5.06 (m, 1H), 1.91-2.01 (m, 2H), 1.46-1.54 (m, 1H), 1.42 (ddt, 1H), 1.01 (t, J = 7.4 Hz, 3H). white solid |
| 3 | 1-(4-Bromophenyl)-3-[(1S)-1-(1H-imidazol-2-yl)-2-methylpropyl]urea | ¹H NMR (CD₃OD, 300 MHz) δ: 7.22-7.44 (m, 4H), 6.96 (s, 2H), 4.71 (d, J = 7.0 Hz, 1H), 2.11-2.30 (m, 1H), 0.96 (d, J = 6.7 Hz, 3H), 0.88 (d, J = 6.7 Hz, 3H). white solid |
| 4 | 1-(4-Bromophenyl)-3-(1H-imidazol-2-ylmethyl)urea | ¹H NMR (CD₃OD, 300 MHz) δ: 7.22-7.47 (m, 4H), 6.96 (s, 2H), 4.42 (s, 2H). white solid |
| 5 | 1-(4-Bromophenyl)-3-[1-(1H-imidazol-2-yl)ethyl]urea | ¹H NMR (CD₃OD, 300 MHz) δ: 7.22-7.48 (m, 4H), 6.96 (s, 2H), 4.97-5.08 (m, 1H), 1.54 (d, J = 7.0 Hz, 3H). white solid |
| 6 | 1-[1-(1H-lmidazol-2-yl)propyl]-3-[4-(trifluoromethyl)phenyl]urea | ¹H NMR (CD₃OD, 300 MHz) δ: 74.7-7.59 (m, 4H), 7.00 (s, 2H), 5.48 (s, NH), 4.86-4.93 (m, 1H), 1.82-2.08 (m, 2H), 0.94 (t, J = 7.5 Hz, 3H). light yellow solid |
| 28 | 1-[(1S)-1-(1H-imidazol-2-yl)-2-methyl propyl]-3-[4-(trifluoromethyl)phenyl] urea | ¹H NMR (CD₃OD, 300 MHz) δ: 7.47-7.59 (m, 4H), 6.97 (s, 2H), 4.73 (d, J = 7.3 Hz, 1H), 2.15-2.32 (m, 1H), 0.98 (d, J = 6.7 Hz, 3H), 0.90 (d, J = 6.7 Hz, 3H). white solid [α]D = +68.8, c = 1.00, MeOH |
| 29 | 1-(4-Chlorophenyl)-3-[(1S)-1-(1H-imidazol-2-yl)-2-methylpropyl]urea | ¹H NMR (CD₃OD, 300 MHz) δ: 7.29-7.38 (m, 2H), 7.18-7.26 (m, 2H), 6.96 (s, 2H), 4.64-4.74 (m, 1H), 2.13-2.29 (m, 1H), 0.97 (d, J = 6.7 Hz, 3H), 0.89 (d, J = 6.7 Hz, 3H). white solid [α]D = +76.6, c = 1.00, MeOH |

TABLE 1-continued

| Comp. No. | IUPAC name Structure | ¹H NMR δ (ppm), form and optical rotation |
|---|---|---|
| 30 | 1-(4-Bromo-2-fluorophenyl)-3-[(1S)-1-(1H-imidazol-2-yl)-2-methylpropyl] urea | ¹H NMR (CD$_3$OD, 300 MHz) δ: 7.97 (t, J = 8.8 Hz, 1H), 7.31 (dd, J = 10.7, 2.2 Hz, 1H), 7.16-7.25 (m, 1H), 6.96 (s, 2H), 4.72 (d, J = 6.7 Hz, 1H), 2.23 (dq, J = 13.8, 6.9 Hz, 1H), 0.96 (d, J = 7.0 Hz, 3H), 0.90 (d, J = 6.7 Hz, 3H). white solid [α]D = +71.0, c = 1.00, MeOH |
| 31 | 1-[(1S)-1-(1H-imidazol-2-yl)-2-methyl propyl]-3-(4-methoxyphenyl)urea | ¹H NMR (CD$_3$OD, 300 MHz) δ: 7.22 (d, J = 8.8 Hz, 2H), 6.96 (s, 2H), 6.78-6.88 (m, 2H), 4.70 (d, J = 7.3 Hz, 1H), 3.74 (s, 3H), 2.12-2.31 (m, 1H), 0.96 (d, J = 6.7 Hz, 3H), 0.88 (d, J = 6.7 Hz, 3H). white solid [α]D = +69.9, c = 1.00, MeOH |

Example 2

Compound 7

Ethyl [2-(1-{[(4-Bromophenyl)carbamoyl]amino}propyl)-1H-imidazol-1-yl]acetate

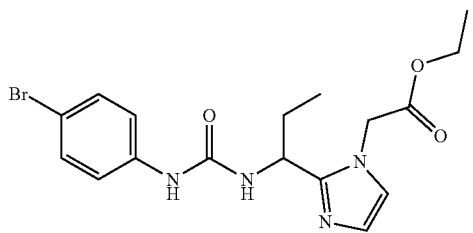 [SMILES: CCOC(=O)Cn1ccnc1C(CC)NC(=O)Nc1ccc(Br)cc1]

To a solution of Compound 1 (257 mg, 0.80 mmol) and 12 mL of DMF at 25° C. was added potassium carbonate (220 mg, 1.60 mmol) and ethyl 2-bromoacetate (0.18 mL, 1.04 mmol). The resulting mixture was stirred at 25° C. for 2 hours. The mixture was concentrated to an oil and quenched with water (4 mL), and the product was extracted with ethyl acetate (20 mL). The layers were separated, and the organic layer was washed with water, brine, dried over Na$_2$SO$_4$, filtered, and the filtrate was concentrated under reduced pressure. The residue was purified by medium pressure liquid chromatography on silica gel using 100% ethyl acetate to yield Compound 7 as white solid.

¹H NMR (CD$_3$OD, 300 MHz) δ ppm: 7.32-7.38 (m, 2H), 7.24-7.31 (m, 2H), 7.04 (s, 1H), 6.94 (s, 1H), 4.89-5.13 (m, 2H), 4.76-4.82 (m, 1H), 4.12 (t, J=6.9 Hz, 2H), 1.85-2.11 (m, 2H), 1.14-1.25 (m, 3H), 0.91-1.03 (m, 3H).

Compounds 8 through 12, 14, 18 and 32 through 36 were prepared from the corresponding urea in a similar manner to the procedure described for Compound 7. The results are tabulated in Table 2.

TABLE 2

| Comp. No. | IUPAC name Structure | ¹H NMR δ (ppm), form and optical rotation |
|---|---|---|
| 8 | Ethyl {2-[(1S)-1-{[(4-bromophenyl)carbamoyl]amino}butyl]-1H-imidazol-1-yl}acetate | ¹H NMR (CD$_3$OD, 300 MHz) δ: 7.22-7.42 (m, 4H), 7.03 (s, 1H), 6.93 (s, 1H), 4.94-5.17 (m, 2H), 4.81-4.90 (m, 1H), 4.00-4.21 (m, 2H), 1.84-2.04 (m, 2H), 1.26-1.51 (m, 2H), 1.19 (t, J = 7.2 Hz, 3H), 0.96 (t, J = 7.3 Hz, 3H). white solid |

TABLE 2-continued

| Comp. No. | IUPAC name Structure | $^1$H NMR δ (ppm), form and optical rotation |
|---|---|---|
| 9 | tert-Butyl {2-[(1S)-1-{[(4-Bromophenyl)carbamoyl]amino}butyl]-1H-imidazol-1-yl}acetate | $^1$H NMR (CD$_3$OD, 300 MHz) δ: 7.20-7.40 (m, 4H), 7.01 (s, 1H), 6.92 (s, 1H), 5.08 (m, 2H), 4.78 (m, 1H), 1.82-2.03 (m, 2H), 1.48 (s, 9H), 1.35 (m, 2H), 0.96 (t, J = 7.3 Hz, 3H). white solid |
| 10 | tert-Butyl {2-[(1S)-1-{[(4-Bromophenyl)carbamoyl]amino}-2-methylpropyl]-1H-imidazol-1-yl}acetate | $^1$H NMR (CD$_3$OD, 300 MHz) δ: 7.23-7.41 (m, 4H), 7.01 (s, 1H), 6.95 (s, 1H), 4.94-5.05 (m, 1H), 4.76-4.82 (m, 1H), 4.57 (d, J = 9.1Hz, 2H), 2.21-2.36 (m, 1H), 1.43 (s, 9H), 1.07 (d, J = 6.4 Hz, 3H), 0.85 (d, J = 6.4 Hz, 3H). white solid |
| 11 | Ethyl [2-({[(4-Bromophenyl)carbamoyl]amino}methyl)-1H-imidazol-1-yl]acetate | $^1$H NMR (CD$_3$OD, 300 MHz) δ: 7.23-7.47 (m, 4H), 7.06 (d, J = 1.2 Hz, 1H), 6.91 (s, 1H), 5.00 (s, 2H), 4.44 (s, 2H), 4.00-4.17 (m, 2H), 1.18 (t, J = 7.0 Hz, 3H). white solid |
| 12 | Ethyl [2-(1-{[(4-bromophenyl)carbamoyl]amino}ethyl)-1H-imidazol-1-yl]acetate | $^1$H NMR (CD$_3$OD, 300 MHz) δ: 7.25-7.38 (m, 4H), 7.04 (s, 1H), 6.93 (s, 1H), 4.97-5.09 (m, 3H), 4.04-4.18 (m, 2H), 1.52-1.58 (m, 3H), 1.19 (t, J = 7.2 Hz, 3H). white solid |
| 14 | Ethyl 2-[2-({[(4-Bromophenyl)carbamoyl]amino}methyl)-1H-imidazol-1-yl]propanoate | $^1$H NMR (CD$_3$OD, 300 MHz) δ: 7.26-7.42 (m, 4H), 7.21 (s, 1H), 6.94 (s, 1H), 5.39 (q, J = 7.0 Hz, 1H), 4.34-4.62 (m, 2H), 4.02-4.21 (m, 2H), 1.72 (d, J = 7.3 Hz, 3H), 1.16 (t, J = 7.0 Hz, 3H). white solid |

TABLE 2-continued

| Comp. No. | IUPAC name Structure | $^1$H NMR δ (ppm), form and optical rotation |
|---|---|---|
| 15 | Ethyl (2-{1-[({[4-(trifluoromethyl)phenyl]amino}carbonyl)amino]propyl}-1H-imidazol-1-yl)acetate 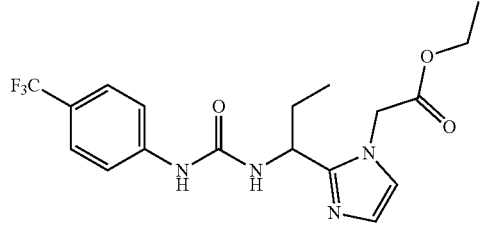 [SMILES: CCOC(=O)Cn1ccnc1C(CC)NC(=O)Nc1ccc(C(F)(F)F)cc1] | $^1$H NMR (CD$_3$OD, 300 MHz) δ 7.49-7.55 (m, 4H), 7.05 (d, J = 1.2 Hz, 1H), 6.94 (d, J = 1.2 Hz, 1H), 4.91-5.17 (m, 2H), 4.82 (m., 1H), 4.03-4.21 (m, 2H), 1.88-2.14 (m, 2H), 1.19 (t, J = 7.2 Hz, 3H), 0.97 (t, J = 7.5 Hz, 3H). Light yellow solid |
| 32 | tert-Butyl (2-{(1S)-2-methyl-1-[({[4-(trifluoromethyl)phenyl]amino}carbonyl)amino]propyl}-1H-imidazol-1-yl)acetate urea 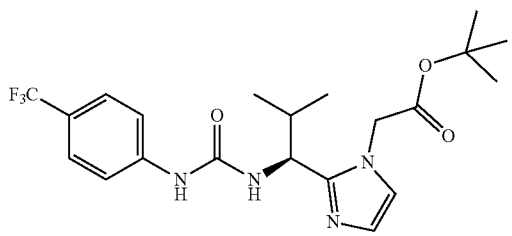 [SMILES: CC(C)[C@H](NC(=O)Nc1ccc(C(F)(F)F)cc1)c1nccn1CC(=O)OC(C)(C)C] | $^1$H NMR (CD$_3$OD, 300 MHz) δ: 7.45-7.59 (m, 4H), 7.02 (d, J = 0.9 Hz, 1H), 6.96 (s, 1H), 4.95-5.08 (m, 1H), 4.87 (m, 1H), 4.59 (d, J = 9.1Hz, 1H), 2.22-2.40 (m, 1H), 1.43 (s, 9H), 1.08 (d, J = 6.7 Hz, 3H), 0.86 (d, J = 6.7 Hz, 3H). yellow oil [α]D = +51.6, c = 1.00, MeOH |
| 33 | tert-Butyl {2-[(1S)-1-({[(4-chlorophenyl)amino]carbonyl}amino)-2-methylpropyl]-1H-imidazol-1-yl}acetate 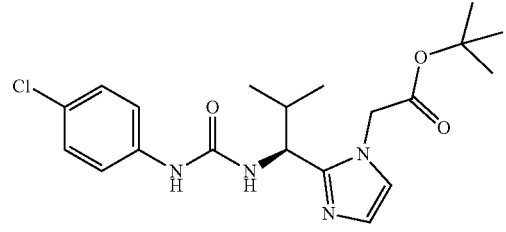 [SMILES: CC(C)[C@H](NC(=O)Nc1ccc(Cl)cc1)c1nccn1CC(=O)OC(C)(C)C] | $^1$H NMR (CD$_3$OD, 300 MHz) δ: 7.28-7.37 (m, 2H), 7.15-7.25 (m, 2H), 7.01 (d, J = 1.2 Hz, 1H), 6.95 (d, J = 1.2 Hz, 1H), 4.94-5.06 (m, 1H), 4.79-4.87 (m, 1H), 4.57 (d, J = 9.4 Hz, 1H), 2.23-2.39 (m, 1H), 1.39-1.47 (m, 9H), 1.08 (d, J = 6.7 Hz, 3H), 0.86 (d, J = 6.4 Hz, 3H). white solid [α]D = +57.8, c = 1.00, MeOH |
| 34 | tert-Butyl {2-[(1S)-1-({[(4-bromo-2-fluorophenyl)amino]carbonyl}amino)-2-methylpropyl]-1H-imidazol-1-yl}acetate 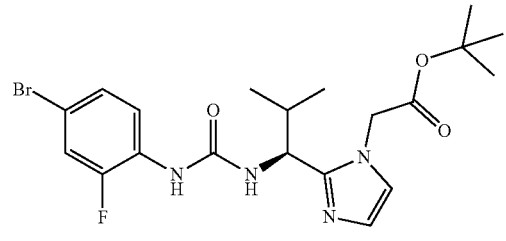 | $^1$H NMR (CD$_3$OD, 300 MHz) δ: 7.98 (t, J = 8.6 Hz, 1H), 7.29 (dd, J = 10.8, 2.1Hz, 1H), 7.22 (d, J = 8.8 Hz, 1H), 7.02 (d, J = 1.2 Hz, 1H), 6.95 (s, 1H), 4.93-5.06 (m, 1H), 4.84-4.87 (m, 1H), 4.56 (d, J = 9.4 Hz, 1H), 2.31 (dq, J = 16.0, 6.6 Hz, 1H), 1.43 (s, 9H), 1.08 (d, J = 6.7 Hz, 3H), 0.86 (d, J = 6.7 Hz, 3H). white solid [α]D = +57.0, c = 1.00, MeOH |
| 35 | tert-Butyl {2-[(1S)-1-({[(4-methoxyphenyl)amino]carbonyl}amino)-2-methylpropyl]-1H-imidazol-1-yl}acetate | $^1$H NMR (CD$_3$OD, 300 MHz) δ: 7.20 (d, J = 8.8 Hz, 2H), 7.01 (d, J = 1.2 Hz, 1H), 6.95 (s, 1H), 6.81 (d, J = 9.1Hz, 2H), 4.97-5.06 (m, |

TABLE 2-continued

| Comp. No. | IUPAC name Structure | $^1$H NMR δ (ppm), form and optical rotation |
|---|---|---|
|  | 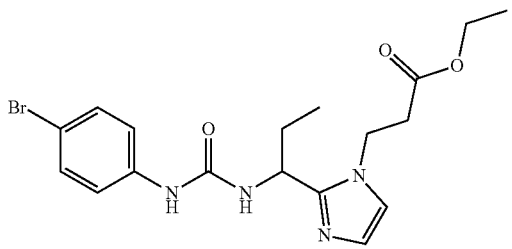 [SMILES: CCOC(=O)CCn1ccnc1C(CC)NC(=O)Nc1ccc(Br)cc1] | 1H), 4.75-4.83 (m, 1H), 4.56 (d, J = 9.4 Hz, 1H), 3.74 (s, 3H), 2.29 (dd, J = 16.0, 6.6 Hz, 1H), 1.44 (s, 9H), 1.08 (d, J = 6.7 Hz, 3H), 0.85 (d, J = 6.7 Hz, 3H). white solid [α]D = +47.5, c = 1.00, MeOH |

Example 3

Compound 23

Ethyl 3-[2-(1[{(4-Bromophenyl)carbamoyl]amino}propyl)-1H-imidazol-1-yl]propanoate To a solution of Compound 1 (137 mg, 0.43 mmol) and 10 mL of EtOH at 25° C. was added DMAP (52 mg, 0.43 mmol) and ethyl acrylate (0.47 mL, 4.3 mmol). The resulting mixture was stirred at 130° C. in a microwave for 3 hours. The mixture was concentrated to an oil and the residue was purified by medium pressure liquid chromatography on silica gel using 100% ethyl acetate to yield Compound 23 as a light yellow solid.

$^1$H NMR (CD$_3$OD, 300 MHz) δ ppm: 7.24-7.39 (m, 4H), 7.06 (s, 1H), 6.91 (s, 1H), 4.99 (t, J=7.3 Hz, 1H), 4.41-4.54 (m, 1H), 4.24-4.36 (m, 1H), 4.10 (q, J=7.1 Hz, 2H), 2.83 (t, J=6.6 Hz, 2H), 1.95 (m, 2H), 1.18 (t, J=7.0 Hz, 3H), 0.96 (t, J=7.3 Hz, 3H).

Compounds 24 and 25 were prepared from the corresponding urea, in a similar manner to the procedure described Compound 20. The results are tabulated in Table 3.

TABLE 3

| Comp. No. | IUPAC name Structure | $^1$H NMR δ (ppm), form and optical rotation |
|---|---|---|
| 24 | Ethyl 3-[2-(1-{[(4-Bromo phenyl)carbamoyl]amino}ethyl)-1H-imidazol-1-yl]propanoate | $^1$H NMR (CD$_3$OD, 600 MHz) δ: 7.36 (d, J = 9.1Hz, 2H), 7.28 (d, J = 9.1Hz, 2H), 7.07 (s, 1H), 6.90 (s, 1H), 5.22 (q, J = 6.9 Hz, 1H), 4.42-4.49 (m, 1H), 4.25-4.32 (m, 1H), 4.07-4.12 (m, 2H), 2.80-2.90 (m, 2H), 1.55 (d, J = 6.7 Hz, 3H), 1.17-1.20 (m, 3H). Off-white solid |
| 25 | Ethyl 3-(2-{1-[({[4-(Trifluoromethyl)phenyl]amino}carbonyl)amino]propyl}-1H-imidazol-1-yl)propanoate | $^1$H NMR (CD$_3$OD, 300 MHz) δ 7.52 (m, 4H), 7.08 (s, 1H), 6.93 (s, 1H), 5.01 (t, J = 7.3 Hz, 1H), 4.41-4.57 (m, 1H), 4.25-4.38 (m, 1H), 4.10 (q, J = 7.1Hz, 2H), 2.77-2.91 (m, 2H), 1.88-2.06 (m, 2H), 1.18 (t, J = 7.2 Hz, 3H), 0.97 (t, J= 7.3 Hz, 3H). white solid |

Example 4

Compound 16

[2-(1-{[(4-Bromophenyl)carbamoyl]amino}propyl)-1H-imidazol-1-yl]acetic Acid

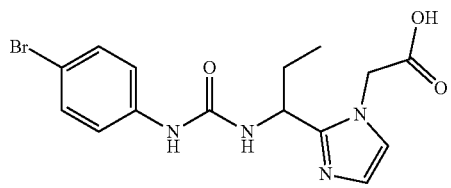 [SMILES: CCC(NC(=O)Nc1ccc(Br)cc1)c1nccn1CC(=O)O]

To a solution of Compound 2 (99 mg, 0.24 mmol) and 10 mL of ethanol was added 1 mL of 1N NaOH. The mixture was stirred at 25° C. for 3 hours. The resulting reaction was quenched with 10% HCl (1 mL), and the product was extracted with EtOAc. The organic layer was washed with water, brine, dried over $Na_2SO_4$, filtered, and concentrated under reduced pressure. The residue was rinsed four times with acetone:hexanes (1:9) to yield Compound 16 as a light yellow solid.

$^1$H NMR ($CD_3OD$, 300 MHz) δ ppm: 7.40 (d, J=8.2 Hz, 2H), 7.24-7.37 (m, 4H), 5.07-5.17 (m, 1H), 4.88-4.98 (m, 2H), 1.94-2.11 (m, 2H), 1.04 (t, J=7.3 Hz, 3H).

Compounds 17 through 22 were prepared from the corresponding esters in a similar manner to the procedure described for Compound 16. The results are tabulated in Table 4.

TABLE 4

| Comp. No. | IUPAC name Structure | $^1$H NMR δ (ppm), form and optical rotation |
|---|---|---|
| 17 | [2-({[(4-Bromophenyl)carbamoyl]amino}methyl)-1H-imidazol-1-yl]acetic Acid | $^1$H NMR ($CD_3OD$, 300 MHz) δ: 7.51 (s, 1H), 7.45 (s, 1H), 7.31-7.40 (m, 4H), 5.10 (s, 2H), 4.62 (s, 2H). white solid |
| 18 | [2-{1-{[(4-Bromophenyl)carbamoyl]amino}ethyl)-1H-imidazol-1-yl]acetic Acid | $^1$H NMR ($CD_3OD$, 300 MHz) δ: 7.50-7.54 (m, 2H), 7.33-7.40 (m, 2H), 7.24-7.31 (m, 2H), 5.07-5.39 (m, 3H), 1.66 (d, J = 7.0 Hz, 3H). Off-white solid |
| 19 | 2-[2-({[(4-Bromophenyl)carbamoyl]amino}methyl)-1H-imidazol-1-yl]propanoic acid | $^1$H NMR ($CD_3OD$, 300 MHz) δ: 7.73 (d, J = 2.1Hz, 1H), 7.52 (s, 1H), 7.35 (m, 4H), 5.48-5.60 (m, 1H), 4.69 (s, 2H), 1.87 (d, J = 7.3 Hz, 3H). white solid |
| 20 | 3-[2-(1-{[(4-Bromophenyl)carbamoyl]amino}propyl)-1H-imidazol-1-yl]propanoic acid | $^1$H NMR ($CD_3OD$, 300 MHz) δ: 8.60 (s, NH), 7.60 (s, 1H), 7.50 (s, 1H), 7.26-7.41 (m, 4H), 6.94 (s, NH), 5.14 (t, J = 7.0 Hz, 1H), 4.70 (dt, J = 14.4, 6.9 Hz, 1H), 4.43-4.54 (m, 1H), 3.00 (m, 2H), 2.04 (quin, J = 7.3 Hz, 2H), 1.09 (t, J = 7.3 Hz, 3H). white solid |

TABLE 4-continued

| Comp. No. | IUPAC name Structure | $^1$H NMR δ (ppm), form and optical rotation |
|---|---|---|
| 21 | (2-{1-[({[4-(Trifluoromethyl)phenyl]amino}carbonyl)amino]propyl}-1H-imidazol-1-yl)acetic acid | $^1$H NMR (CD$_3$OD, 300 MHz) δ 7.50-7.58 (m, 6H), 5.14-5.44 (m, 2H), 5.01 (t, J = 7.3 Hz, 1H), 1.96-2.13 (m, 2H), 1.07 (t, J = 7.3 Hz, 3H). white solid |
| 22 | 3-(2-{1-[({[4-(Trifluoromethyl)phenyl]amino}carbonyl)amino]propyl}-1H-imidazol-1-yl)propanoic acid | $^1$H NMR (CD$_3$OD, 300 MHz) δ: 7.44-7.65 (m, 6H), 5.11-5.23 (m, 1H), 4.65-4.80 (m, 1H), 4.50 (dt, J = 14.5, 5.9 Hz, 1H), 2.99-3.10 (m, 2H), 2.02-2.14 (m, 2H), 1.05-1.17 (m, 3H). white solid |

Example 5

Compound 26

{2-[(1S)-1-{[(4-Bromophenyl)carbamoyl]amino}butyl]-1H-imidazol-1-yl}acetic acid

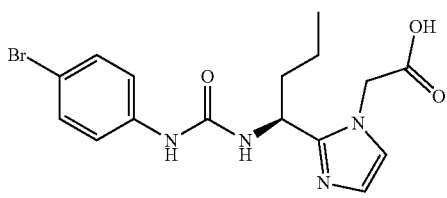 [SMILES: CCC[C@H](NC(=O)Nc1ccc(Br)cc1)c1nccn1CC(=O)O]

A solution of Compound 9 (100 mg, 0.22 mmol) and 10 mL of formic acid was stirred at 50° C. for 12 hours. The resulting reaction was quenched with water (10 mL), and the product was extracted with EtOAc. The organic layer was washed with water, brine, dried over Na$_2$SO$_4$, filtered, and concentrated under reduced pressure. The residue was rinsed two times with acetone:hexane (5:95) to yield Compound 26 as an off white solid.

$^1$H NMR (CD$_3$OD, 300 MHz) δ: 7.46 (s, 1H), 7.44 (s, 1H), 7.33-7.39 (m, 2H), 7.25-7.31 (m, 2H), 5.13-5.27 (m, 1H), 4.96-5.11 (m, 2H), 1.90-2.04 (m, 2H), 1.32-1.64 (m, 2H), 0.99 (t, J=7.3 Hz, 3H).

Compounds 27 and 36 through 39 were prepared from the corresponding ester derivative in a similar manner to the procedure described in for Compound 26. The results are tabulated in Table 8.

TABLE 5

| Comp. No. | IUPAC name Structure | $^1$H NMR δ (ppm), form and optical rotation |
|---|---|---|
| 27 | (2-[(1S)-1-{[(4-Bromophenyl)carbamoyl]amino}-2-methylpropyl]-1H-imidazol-1-yl}acetic acid | $^1$H NMR (CD$_3$OD, 300 MHz) δ: 7.43 (s, 1H), 7.40 (s, 1H), 7.31 (m, 4H), 5.16 (m, 1H), 4.89-5.02 (m, 1H), 4.80 (m, 1H), 3.52-3.52 (m, 1H), 2.25-2.46 (m, 1H), 1.11 (d, J = 6.7 Hz, 3H), 0.94 (d, J = 6.7 Hz, 3H). White solid |

TABLE 5-continued

| Comp. No. | IUPAC name Structure | $^1$H NMR δ (ppm), form and optical rotation |
|---|---|---|
| 36 | (2-{(1S)-2-Methyl-1-[({[4-(trifluoromethyl)phenyl]amino}carbonyl)amino]propyl}-1H-imidazol-1-yl)acetic acid | $^1$H NMR (CD$_3$OD, 300 MHz) δ: 7.44-7.58 (m, 4H), 7.39 (d, J = 1.8 Hz, 1H), 7.36 (s, 1H), 5.01-5.14 (m, 1H), 4.90 (m, 1H), 4.79 (m, 1H), 2.29-2.47 (m, 1H), 1.11 (d, J = 6.7 Hz, 3H), 0.95 (d, J = 6.7 Hz, 3H). white solid [α]D = +12.2, c = 1.00, MeOH |
| 37 | {2-[(1S)-1-({[(4-Chlorophenyl)amino]carbonyl}amino)-2-methylpropyl]-1H-imidazol-1-yl}acetic acid | $^1$H NMR (CD$_3$OD, 300 MHz) δ: 7.41-7.51 (m, 2H), 7.26-7.37 (m, 2H), 7.13-7.24 (m, 2H), 5.14-5.28 (m, 1H), 4.94-5.08 (m, 1H), 4.81 (d, J = 8.8 Hz, 1H), 2.26-2.45 (m, 1H), 1.12 (d, J = 6.7 Hz, 3H), 0.95 (d, J = 6.7 Hz, 3H). white solid [α]D = +16.6, c = 0.50, MeOH |
| 38 | {2-[(1S)-1-({[(4-bromo-2-fluorophenyl)amino]carbonyl}amino)-2-methylpropyl]-1H-imidazol-1-yl}acetic acid | $^1$H NMR (CD$_3$OD, 300 MHz) δ: 7.93 (t, J = 8.6 Hz, 1H), 7.43-7.53 (m, 2H), 7.32 (dd, J = 10.5, 2.1 Hz, 1H), 7.22 (d, J = 8.5 Hz, 1H), 5.16-5.30 (m, 1H), 4.98-5.11 (m, 1H), 4.82-4.84 (m, 1H), 2.27-2.45 (m, 1H), 1.08-1.17 (m, 3H), 0.96 (d, J = 6.7 Hz, 3H). white solid [α]D = +17.2, c = 1.00, MeOH |
| 39 | {2-[(1S)-1-({[(4-methoxyphenyl)amino]carbonyl}amino)-2-methylpropyl]-1H-imidazol-1-yl}acetic acid | $^1$H NMR (CD$_3$OD, 300 MHz) δ: 7.44-7.52 (m, 2H), 7.21 (d, J = 8.8 Hz, 2H), 6.80 (d, J = 9.1Hz, 2H), 5.17-5.29 (m, 1H), 4.98-5.10 (m, 1H), 4.82 (d, J = 9.1Hz, 1H), 3.73 (s, 3H), 2.28-2.44 (m, 1H), 1.12 (d, J = 6.7 Hz, 3H), 0.94 (d, J = 6.7 Hz, 3H). white solid [α]D = +13.4, c = 0.50, MeOH |

Example 6

Compound 40

2-(2-{(1S)-2-methyl-1-[({[4-(trifluoromethyl)phenyl]amino}carbonyl)amino]propyl}-1H-imidazol-1-yl)acetamide

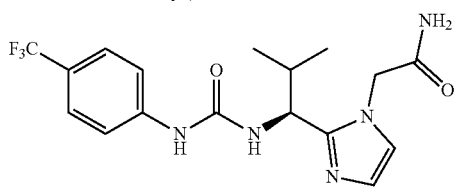

To a solution of Compound 36 (50 mg, 0.13 mmol) and 6 mL of anhydrous tetrahydrofuran under argon at −78 OC was added triethylamine (17 mg, 0.17 mmol), and ethyl chloroformate (17 mg, 0.16 mmol). The mixture was stirred at −78° C. for 30 minutes, then ammonia gas was bubbled into the reaction flask for 1 minute. The resulting mixture was stirred at 25° C. for 1 hour. The mixture was quenched with water (1 mL), then extracted with ethyl acetate (20 mL). The layers were separated, and the organic layer was washed with water, brine, dried over Na$_2$SO$_4$, filtered, and concentrated under reduced pressure. The resulting product was purified by medium pressure liquid chromatography on silica gel using methanol:dichloromethane (1:9) to yield Compound 40 as white solid. The physicochemical data for Compound 40 are shown in Table 6.

Compound 41

2-(2-{(1S)-2-methyl-1-[({[4-(trifluoromethyl)phenyl]amino}carbonyl)amino]propyl}-1H-imidazol-1-yl)-N-propylacetamide

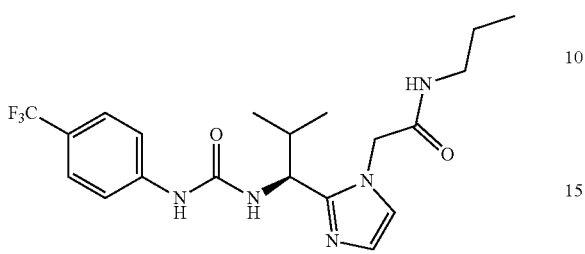

A solution of Compound 36 (47 mg, 0.12 mmol), EDC (35 mg, 0.18 mmol), HOBt (255 mg, 0.18 mmol), propylamine (9 mg, 0.14 mmol), N-methylmorpholine (25 mg, 0.24 mmol) and 8 mL of anhydrous dichloromethane was stirred at 25° C. for 12 hours. The mixture was quenched with water (10 mL), and the product was extracted with EtOAc. The organic layer was washed with water, brine, dried over $Na_2SO_4$, filtered, and concentrated under reduced pressure. The resulting product was purified by medium pressure liquid chromatography on silica gel using 100% ethyl acetate to yield Compound 41 as white solid. The physicochemical data for Compound 41 are shown in Table 6.

Compound 42

N,N-Dimethyl-2-(2-{(1S)-2-methyl-1-[({[4-(trifluoromethyl)phenyl]amino}carbonyl)amino]propyl}-1H-imidazol-1-yl)acetamide

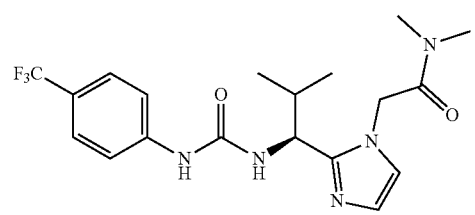

Compound 42 was prepared from the corresponding acid derivative in a similar manner to the procedure described in for Compound 41. The physicochemical data for Compound 42 are shown in Table 6.

TABLE 6

| Comp. No. | IUPAC name Structure | $^1$H NMR δ (ppm), form and optical rotation |
|---|---|---|
| 40 | 2-(2-{(1S)-2-methyl-1-[({[4-(trifluoromethyl)phenyl]amino}carbonyl)amino] propyl}-1H-imidazol-1-yl)acetamide | $^1$H NMR (CD$_3$OD, 300 MHz) δ: 7.46-7.58 (m, 4H), 7.33 (s, NH), 7.28 (s, 1H), 7.23 (s, 1H), 4.91-5.01 (m, 1H), 4.76-4.83 (m, 2H), 2.28-2.44 (m, 1H), 1.10 (d, J = 6.4 Hz, 3H), 0.95 (d, J = 6.4 Hz, 3H). white solid [α]D = +8.1, c = 1.00, MeOH |
| 41 | 2-(2-{(1S)-2-methyl-1-[({[4-(trifluoromethyl)phenyl]amino}carbonyl)amino] propyl}-1H-imidazol-1-yl)-N-propylacetamide | $^1$H NMR (CD$_3$OD, 300 MHz) δ: 7.51 (s, 4H), 7.03 (s, 1H), 6.96 (s, 1H), 4.86-4.96 (m, 1H), 4.81 (m, 1H), 4.63 (d, J = 8.8 Hz, 1H), 3.07-3.19 (m, 2H), 2.17-2.36 (m, 1H), 1.43-1.57 (m, 2H), 1.06-1.16 (m, 3H), 0.82-0.93 (m, 6H). white solid [α]D = +51.3, c = 1.00, MeOH |

TABLE 6-continued

| Comp. No. | IUPAC name Structure | $^1$H NMR δ (ppm), form and optical rotation |
|---|---|---|
| 42 | N,N-Dimethyl-2-(2-{(1S)-2-methyl-1-[({[4-(trifluoromethyl)phenyl]amino}carbonyl)amino]propyl}-1H-imidazol-1-yl)acetamide | $^1$H NMR (CD$_3$OD, 600 MHz) δ: 7.53 (br. s., 4H), 7.01-7.03 (m, 1H), 6.99 (br. s., 1H), 5.07-5.22 (m, 2H), 4.61 (d, J = 9.1Hz, 1H), 3.12 (s, 3H), 2.82 (s, 3H), 1.09 (d, J = 6.5 Hz, 3H), 0.92 (d, J = 6.5 Hz, 3H). white solid [α]D = +59.6, c = 0.666, MeOH |

Example 7

Compound 13

1-(4-Bromophenyl)-3-{1-[1-(2-hydroxyethyl)-1H-imidazol-2-yl]ethyl}urea

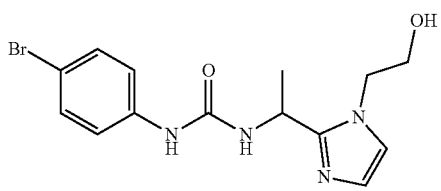

To a solution of Compound 5 (150 mg, 0.49 mmol) in a sealed tube and 2 mL of DMF at 25° C. was added potassium carbonate (100 mg, 0.75 mmol) and 2-bromoethanol (0.10 mL, 1.50 mmol). The resulting mixture was stirred at 80° C. for 36 hours. The mixture was concentrated to an oil and quenched with water (4 mL), and the product was extracted with ethyl acetate (20 mL). The layers were separated, and the organic layer was washed with water, brine, dried over Na$_2$SO$_4$, filtered, and the filtrate was concentrated under reduced pressure. The residue was purified by medium pressure liquid chromatography on silica gel using methanol:dichloromethane (1:9) to yield Compound 13 as white solid.

$^1$H NMR (CD$_3$OD, 300 MHz) δ: 7.22-7.40 (m, 4H), 7.08 (s, 1H), 6.92 (s, 1H), 5.19 (m, 1H), 4.21-4.37 (m, 1H), 4.01-4.15 (m, 1H), 3.72-3.89 (m, 2H), 1.54 (d, J=7.0 Hz, 3H).

Example 8

Biological Data

Biological activity of compounds according to Formula I is set forth in Table 7 below. CHO-Gα16 cells stably expressing FPR2 were cultured in (F12, 10% FBS, 1% PSA, 400 µg/ml geneticin and 50 µg/ml hygromycin). In general, the day before the experiment, 18,000 cells/well were plated in a 384-well clear bottom poly-D-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as EC$_{50}$ (nM) and efficacy values.

TABLE 7

| Number | IUPAC name | Structure | FPR2 Ga16-CHO EC$_{50}$ (% eff) |
|---|---|---|---|
| 1 | 1-(4-Bromophenyl)-3-[1-(1H-imidazol-2-yl)propyl]urea | 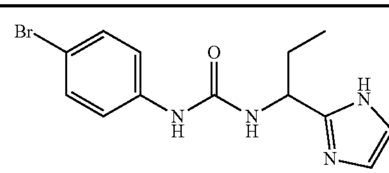 | 898 nM (0.87) |
| 2 | 1-(4-Bromophenyl)-3-[(1S)-1-(1H-imidazol-2-yl)butyl]urea | 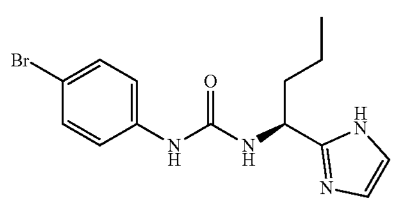 [SMILES: CCC[C@H](NC(=O)Nc1ccc(Br)cc1)c1ncc[nH]1] | 2071 nM (0.43) |

TABLE 7-continued

| Number | IUPAC name | Structure | FPR2 Gα16-CHO EC$_{50}$ (% eff) |
|---|---|---|---|
| 3 | 1-(4-Bromophenyl)-3-[(1S)-1-(1H-imidazol-2-yl)-2-methylpropyl]urea | 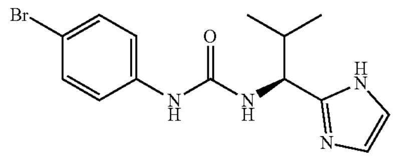 | 46 nM (0.98) |
| 4 | 1-(4-Bromophenyl)-3-(1H-imidazol-2-ylmethyl)urea | 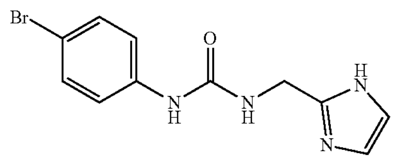 [SMILES: O=C(NCc1ncc[nH]1)Nc1ccc(Br)cc1] | 175 nM (0.83) |
| 5 | 1-(4-Bromophenyl)-3-[1-(1H-imidazol-2-yl)ethyl]urea | 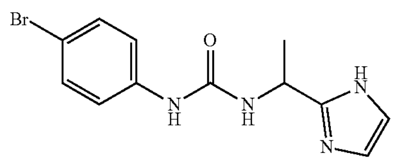 | 401 nM (0.70) |
| 6 | 1-[1-(1H-Imidazol-2-yl)propyl]-3-[4-(trifluoromethyl)phenyl]urea | 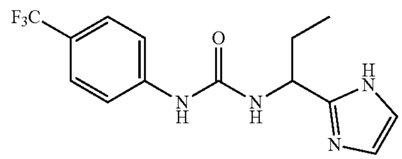 [SMILES: CCC(NC(=O)Nc1ccc(C(F)(F)F)cc1)c1ncc[nH]1] | 199 nM (1.01) |
| 7 | Ethyl [2-(1-{[(4-Bromophenyl)carbamoyl]amino}propyl)-1H-imidazol-1-yl]acetate | 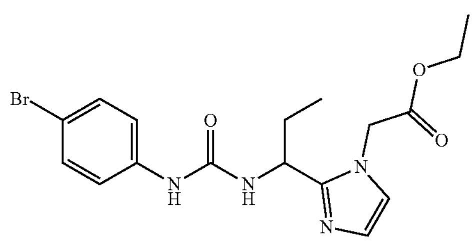 [SMILES: CCOC(=O)Cn1ccnc1C(CC)NC(=O)Nc1ccc(Br)cc1] | 439 nM (0.81) |
| 8 | Ethyl {2-[(1S)-1-{[(4-bromophenyl)carbamoyl]amino}butyl]-1H-imidazol-1-yl}acetate | 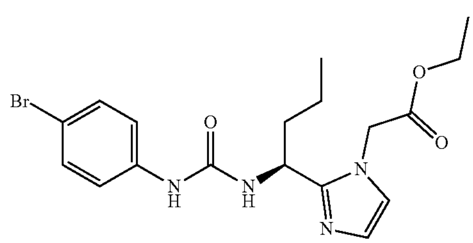 [SMILES: CCC[C@H](NC(=O)Nc1ccc(Br)cc1)c1nccn1CC(=O)OCC] | 1091 nM (0.80) |
| 9 | tert-Butyl {2-[(1S)-1-{[(4-Bromophenyl)carbamoyl]amino}butyl]-1H-imidazol-1-yl}acetate | 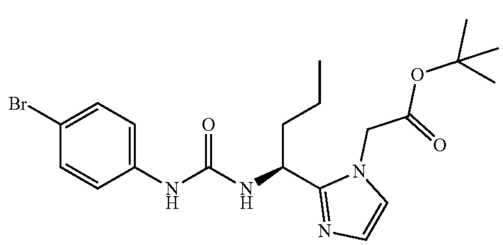 [SMILES: CCC[C@H](NC(=O)Nc1ccc(Br)cc1)c1nccn1CC(=O)OC(C)(C)C] | 1288 nM (0.09) |

TABLE 7-continued

| Number | IUPAC name | Structure | FPR2 Gα16-CHO EC$_{50}$ (% eff) |
|---|---|---|---|
| 10 | tert-Butyl {2-[(1S)-1-{[(4-Bromophenyl)carbamoyl]amino}-2-methylpropyl]-1H-imidazol-1-yl}acetate | 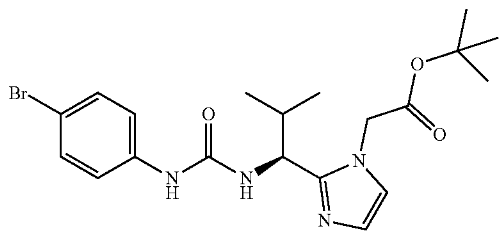 | 1107 nm (0.86) |
| 11 | Ethyl [2-({[(4-Bromophenyl)carbamoyl]amino}methyl)-1H-imidazol-1-yl]acetate | 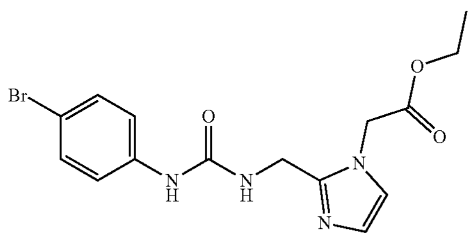 [SMILES: CCOC(=O)Cn1ccnc1CNC(=O)Nc1ccc(Br)cc1] | 400 nM (0.72) |
| 12 | Ethyl [2-(1-{[(4-Bromophenyl)carbamoyl]amino}ethyl)-1H-imidazol-1-yl]acetate | 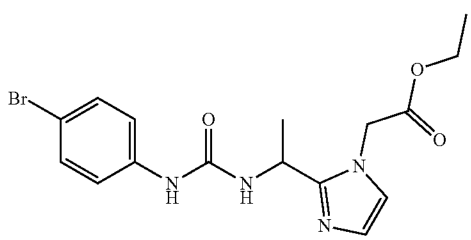 [SMILES: CCOC(=O)Cn1ccnc1C(C)NC(=O)Nc1ccc(Br)cc1] | >2000 nM (0.43) |
| 13 | 1-(4-Bromophenyl)-3-{1-[1-(2-hydroxyethyl)-1H-imidazol-2-yl]ethyl}urea | 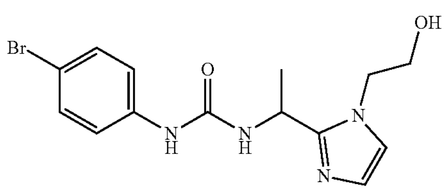 [SMILES: CC(NC(=O)Nc1ccc(Br)cc1)c1nccn1CCO] | 200 nM (0.87) |
| 14 | Ethyl 2-[2-({[(4-Bromophenyl)carbamoyl]amino}methyl)-1H-imidazol-1-yl]propanoate | 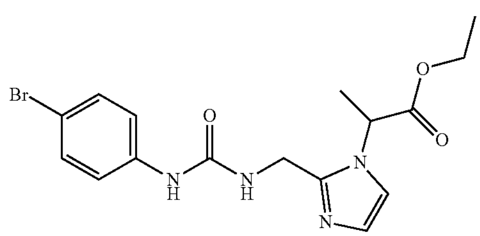 [SMILES: CCOC(=O)C(C)n1ccnc1CNC(=O)Nc1ccc(Br)cc1] | 584 nM (0.76) |
| 15 | Ethyl {2-[1-({[4-(trifluoromethyl)phenyl]carbamoyl}amino)propyl]-1H-imidazol-1-yl}acetate | 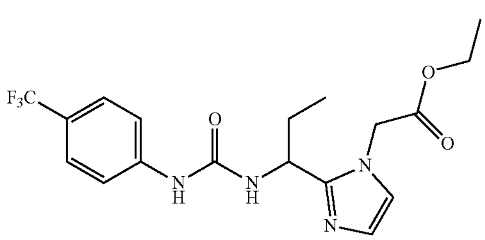 [SMILES: CCOC(=O)Cn1ccnc1C(CC)NC(=O)Nc1ccc(C(F)(F)F)cc1] | 332 nM (0.90) |

TABLE 7-continued

| Number | IUPAC name | Structure | FPR2 Gα16-CHO EC$_{50}$ (% eff) |
|---|---|---|---|
| 16 | [2-(1-{[(4-Bromophenyl)carbamoyl]amino}propyl)-1H-imidazol-1-yl]acetic acid | 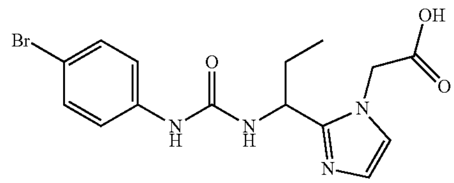 [SMILES: CCC(NC(=O)Nc1ccc(Br)cc1)c1nccn1CC(=O)O] | 47 nM (0.85) |
| 17 | [2-({[(4-Bromophenyl)carbamoyl]amino}methyl)-1H-imidazol-1-yl]acetic acid | 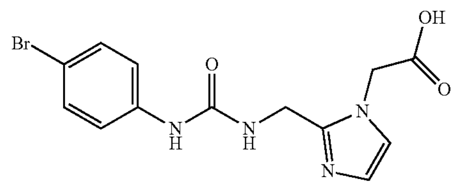 [SMILES: O=C(O)Cn1ccnc1CNC(=O)Nc1ccc(Br)cc1] | 3281 nM (0.72) |
| 18 | [2-(1-{[(4-Bromophenyl)carbamoyl]amino}ethyl)-1H-imidazol-1-yl]acetic acid | 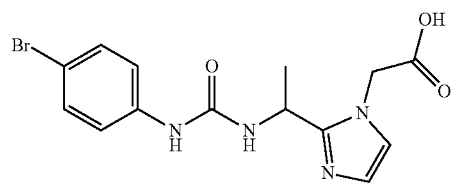 [SMILES: CC(NC(=O)Nc1ccc(Br)cc1)c1nccn1CC(=O)O] | 30 nM (0.94) |
| 19 | 2-[2-({[(4-Bromophenyl)carbamoyl]amino}methyl)-1H-imidazol-1-yl]propanoic acid | 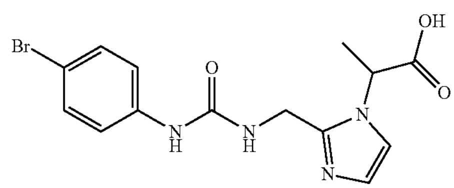 [SMILES: CC(C(=O)O)n1ccnc1CNC(=O)Nc1ccc(Br)cc1] | 270 nM (0.77) |
| 20 | 3-[2-(1-{[(4-Bromophenyl)carbamoyl]amino}propyl)-1H-imidazol-1-yl]propanoic acid | 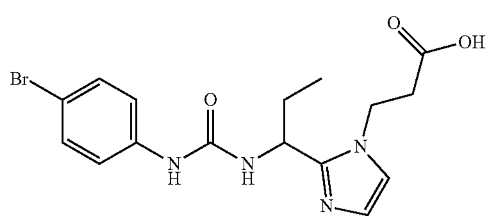 [SMILES: CCC(NC(=O)Nc1ccc(Br)cc1)c1nccn1CCC(=O)O] | 42 nM (1.12) |
| 21 | {2-[1-({[4-(Trifluoromethyl)phenyl]carbamoyl}amino)propyl]-1H-imidazol-1-yl}acetic acid | 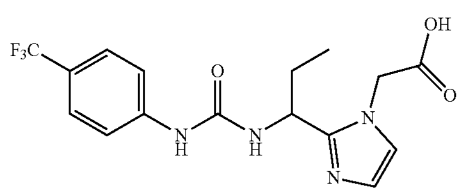 [SMILES: CCC(NC(=O)Nc1ccc(C(F)(F)F)cc1)c1nccn1CC(=O)O] | 6.6 nM (0.99) |
| 22 | 3-{2-[1-({[4-(Trifluoromethyl)phenyl]carbamoyl}amino)propyl]-1H-imidazol-1-yl}propanoic acid | 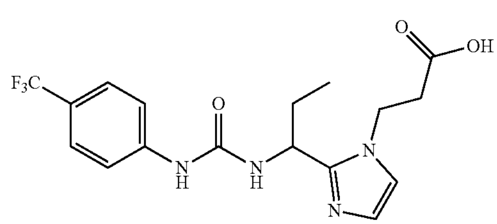 [SMILES: CCC(NC(=O)Nc1ccc(C(F)(F)F)cc1)c1nccn1CCC(=O)O] | 23 nM (0.91) |

TABLE 7-continued

| Number | IUPAC name | Structure | FPR2 Gα16-CHO EC$_{50}$ (% eff) |
|---|---|---|---|
| 23 | Ethyl 3-[2-(1-{[(4-Bromophenyl)carbamoyl]amino}propyl)-1H-imidazol-1-yl]propanoate | 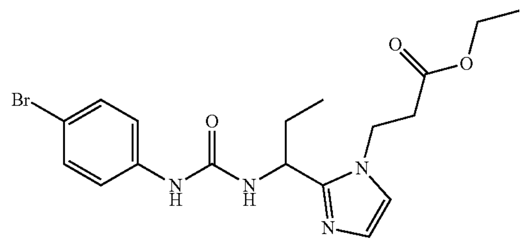 [SMILES: CCOC(=O)CCn1ccnc1C(CC)NC(=O)Nc1ccc(Br)cc1] | 1212 nM (0.96) |
| 24 | Ethyl 3-[2-(1-{[(4-Bromophenyl)carbamoyl]amino}ethyl)-1H-imidazol-1-yl]propanoate | 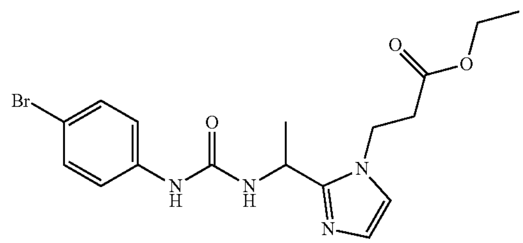 [SMILES: CCOC(=O)CCn1ccnc1C(C)NC(=O)Nc1ccc(Br)cc1] | 734 nM (0.31) |
| 25 | Ethyl 3-{2-[1-({[4-(trifluoromethyl)phenyl]carbamoyl}amino)propyl]-1H-imidazol-1-yl}propanoate | 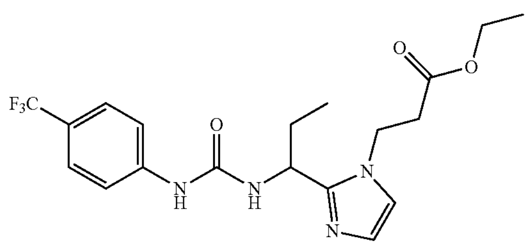 [SMILES: CCOC(=O)CCn1ccnc1C(CC)NC(=O)Nc1ccc(C(F)(F)F)cc1] | 1106 nM (0.93) |
| 26 | {2-[(1S)-1-{[(4-Bromophenyl)carbamoyl]amino}butyl]-1H-imidazol-1-yl}acetic acid | 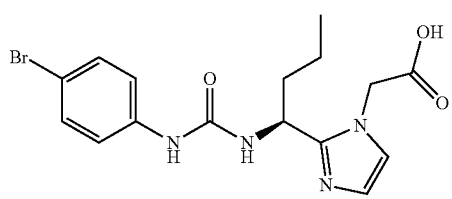 [SMILES: CCC[C@H](NC(=O)Nc1ccc(Br)cc1)c1nccn1CC(=O)O] | 173 nM (0.75) |
| 27 | {2-[(1S)-1-{[(4-Bromophenyl)carbamoyl]amino}-2-methylpropyl]-1H-imidazol-1-yl}acetic acid | 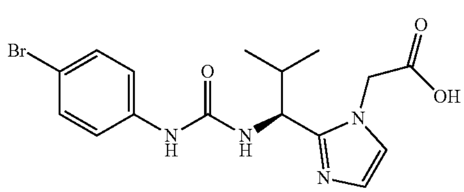 [SMILES: CC(C)[C@H](NC(=O)Nc1ccc(Br)cc1)c1nccn1CC(=O)O] | 46 nM (0.95) |
| 28 | 1-[(1S)-1-(1H-imidazol-2-yl)-2-methylpropyl]-3-[4-(trifluoromethyl)phenyl]urea | 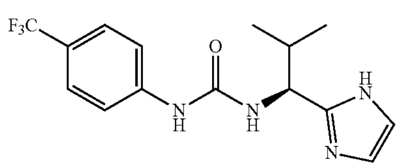 [SMILES: CC(C)[C@H](NC(=O)Nc1ccc(C(F)(F)F)cc1)c1ncc[nH]1] | 4 nM (1.05) |
| 29 | 1-(4-Chlorophenyl)-3-[(1S)-1-(1H-imidazol-2-yl)-2-methylpropyl]urea | 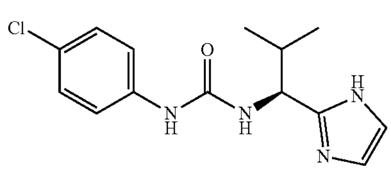 [SMILES: CC(C)[C@H](NC(=O)Nc1ccc(Cl)cc1)c1ncc[nH]1] | 9 nM (0.96) |

TABLE 7-continued

| Number | IUPAC name | Structure | FPR2 Gα16-CHO EC$_{50}$ (% eff) |
|---|---|---|---|
| 30 | 1-(4-Bromo-2-fluorophenyl)-3-[(1S)-1-(1H-imidazol-2-yl)-2-methylpropyl]urea | 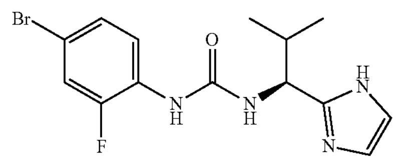 [SMILES: CC(C)[C@H](NC(=O)Nc1ccc(Br)cc1F)c1ncc[nH]1] | 8 nM (0.87) |
| 31 | 1-[(1S)-1-(1H-imidazol-2-yl)-2-methylpropyl]-3-(4-methoxyphenyl)urea | 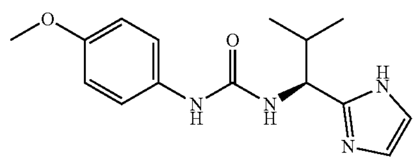 [SMILES: COc1ccc(NC(=O)N[C@H](c2ncc[nH]2)C(C)C)cc1] | 109 nM (1.24) |
| 32 | tert-Butyl (2-{(1S)-2-methyl-1-[({[4-(trifluoromethyl)phenyl]amino}carbonyl)amino]propyl}-1H-imidazol-1-yl)acetate urea | 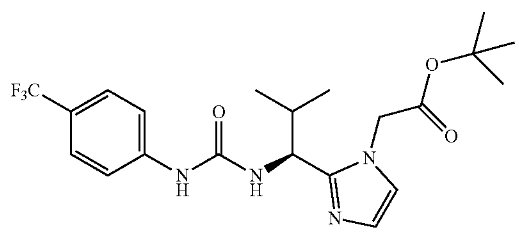 [SMILES: CC(C)[C@H](NC(=O)Nc1ccc(C(F)(F)F)cc1)c1nccn1CC(=O)OC(C)(C)C] | ND |
| 33 | tert-Butyl {2-[(1S)-1-({[(4-chlorophenyl)amino]carbonyl}amino)-2-methylpropyl]-1H-imidazol-1-yl}acetate | 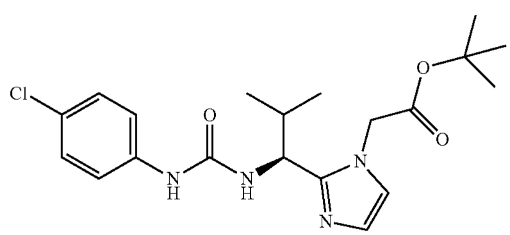 [SMILES: CC(C)[C@H](NC(=O)Nc1ccc(Cl)cc1)c1nccn1CC(=O)OC(C)(C)C] | 361 nM (0.77) |
| 34 | tert-Butyl {2-[(1S)-1-({[(4-bromo-2-fluorophenyl)amino]carbonyl}amino)-2-methylpropyl]-1H-imidazol-1-yl}acetate | 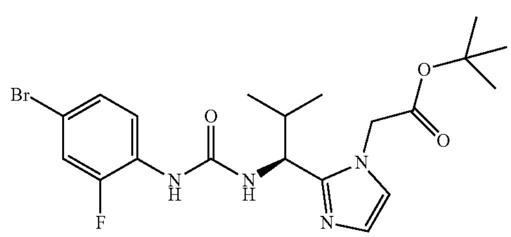 [SMILES: CC(C)[C@H](NC(=O)Nc1ccc(Br)cc1F)c1nccn1CC(=O)OC(C)(C)C] | 855 nM (0.87) |
| 35 | tert-Butyl {2-[(1S)-1-({[(4-methoxyphenyl)amino]carbonyl}amino)-2-methlpropyl]-1H-imidazol-1-yl}acetate | 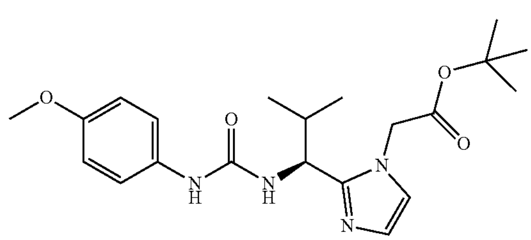 [SMILES: COc1ccc(NC(=O)N[C@H](c2nccn2CC(=O)OC(C)(C)C)C(C)C)cc1] | 139 nM (0.78) |
| 36 | (2-{(1S)-2-Methyl-1-[({[4-(trifluoromethyl)phenyl]amino}carbonyl)amino]propyl}-1H-imidazol-1-yl)acetic acid | 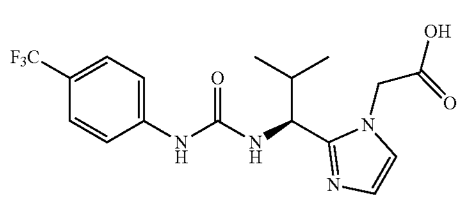 [SMILES: CC(C)[C@H](NC(=O)Nc1ccc(C(F)(F)F)cc1)c1nccn1CC(=O)O] | 3 nM (1.00) |

TABLE 7-continued

| Number | IUPAC name | Structure | FPR2 Gα16-CHO EC$_{50}$ (% eff) |
|---|---|---|---|
| 37 | {2-[(1S)-1-({[(4-Chlorophenyl)amino]carbonyl}amino)-2-methylpropyl]-1H-imidazol-1-yl}acetic acid | 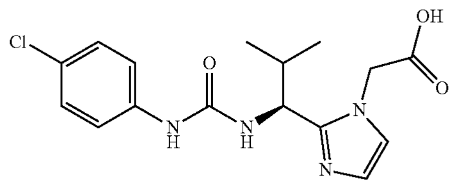 [SMILES: CC(C)[C@H](NC(=O)Nc1ccc(Cl)cc1)c1nccn1CC(=O)O] | 40 nM (0.95) |
| 38 | {2-[(1S)-1-({[(4-bromo-2-fluorophenyl)amino]carbonyl}amino)-2-methylpropyl]-1H-imidazol-1-yl}acetic acid | 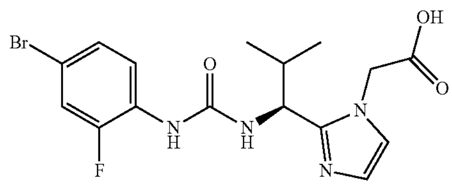 [SMILES: CC(C)[C@H](NC(=O)Nc1ccc(Br)cc1F)c1nccn1CC(=O)O] | 14 nM (1.21) |
| 39 | {2-[(1S)-1-({[(4-methoxyphenyl)amino]carbonyl}amino)-2-methylpropyl]-1H-imidazol-1-yl}acetic acid | 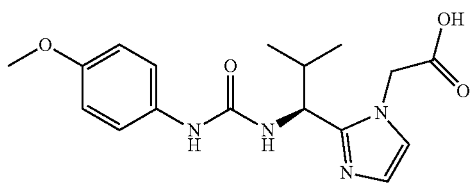 [SMILES: COc1ccc(NC(=O)N[C@H](c2nccn2CC(=O)O)C(C)C)cc1] | 106 nM (0.85) |
| 40 | 2-(2-{(1S)-2-methyl-1-[({[4-(trifluoromethyl)phenyl]amino}carbonyl)amino]propyl}-1H-imdazol-1-yl)acetamide | 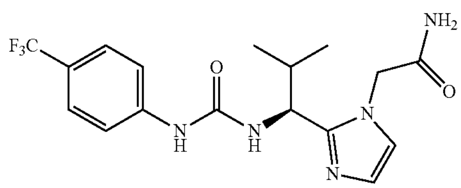 [SMILES: CC(C)[C@H](NC(=O)Nc1ccc(C(F)(F)F)cc1)c1nccn1CC(N)=O] | 43 nM (0.96) |
| 41 | 2-(2-{(1S)-2-methyl-1-[({[4-(trifluoromethyl)phenyl]amino}carbonyl)amino]propyl}-1H-imidazol-1-yl)-N-propylacetamide | 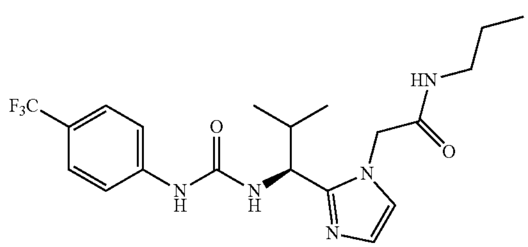 [SMILES: CCCNC(=O)Cn1ccnc1[C@@H](NC(=O)Nc1ccc(C(F)(F)F)cc1)C(C)C] | 206 nM (1.01) |
| 42 | N,N-Dimethyl-2-(2-{(1S)-2-methyl-1-[({[4-(trifluoromethyl)phenyl]amino}carbonyl)amino]propyl}-1H-imidazol-1-yl)acetamide | 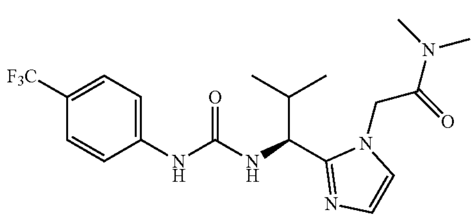 [SMILES: CC(C)[C@H](NC(=O)Nc1ccc(C(F)(F)F)cc1)c1nccn1CC(=O)N(C)C] | 277 nM (0.96) |

ND: Not determined

What is claimed is:

1. A method of treating a disease or condition mediated by FPR2 in a subject in need thereof, the method comprising administering to the subject a therapeutically effective amount of a compound of Formula I:

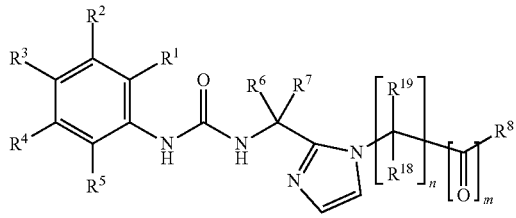

Formula I wherein:
each $R^1$, $R^2$, $R^4$ and $R^5$ is independently selected from the group consisting of H, optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, —S(O)$_2$NR$^{10}$R$^{11}$, —NR$^{12}$R$^{13}$, —S(O)$_p$R$^{14}$, —C(O)R$^{15}$, —SR$^{16}$ and —OR$^{16}$; wherein:
each said optional alkyl substituent is independently selected from one or more $R^{20}$; each said optional cycloalkyl substituent is independently selected from one or more $R^{21}$; each said optional heterocycle substituent is independently selected from one or more $R^{22}$; each said optional aryl substituent is independently selected from one or more $R^{23}$; and each said optional cycloalkenyl substituent is independently selected from one or more $R^{24}$;
$R^3$ is selected from the group consisting of optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, halogen, —S(O)$_2$NR$^{10}$R$^{11}$, —NR$^{12}$R$^{13}$, —S(O)$_p$R$^{14}$, —C(O)R$^{15}$, —SR$^{16}$ and —OR$^{17}$, wherein said optional alkyl substituent is selected from one or more $R^{20}$; said optional cycloalkyl substituent is selected from one or more $R^{21}$; said optional heterocycle substituent is selected from one or more $R^{22}$; said optional aryl substituent is selected from one or more $R^{23}$; and said optional cycloalkenyl substituent is selected from one or more $R^{24}$;
$R^6$ is H, or optionally substituted $C_{1-8}$ alkyl, wherein said optional alkyl substituent is selected from one or more $R^{25}$;
$R^7$ is H, or optionally substituted $C_{1-8}$ alkyl, wherein said optional alkyl substituent is selected from one or more $R^{25}$;
$R^8$ is selected from the group consisting of H, OR$^9$, NR$^{10}$R$^{11}$, sulfonate, sulfonic acid, phosphonate, phosphonic acid, phosphoric acid and optionally substituted heterocycle, wherein said heterocycle is selected from the group consisting of tetrazole, imidazole, thiazole, oxazole, triazole, thiophene, pyrazole and pyrrole; and wherein said optional heterocycle substituent is an optionally substituted $C_{1-8}$ alkyl, wherein said optional alkyl substituent is selected from OH and halogen;
$R^9$ is H or optionally substituted $C_{1-8}$ alkyl, wherein said optional alkyl substituent is selected from the group consisting of OH, halogen, —OC$_{1-8}$ alkyl and —(OC$_{1-8}$ alkylene)$_q$-OC$_{1-8}$ alkyl;

each $R^{10}$ is independently H or unsubstituted $C_{1-8}$ alkyl, or together with $R^{11}$ forms an unsubstituted heterocyclic ring;
each $R^{11}$ is independently H or unsubstituted $C_{1-8}$ alkyl, or together with $R^{10}$ forms an unsubstituted heterocyclic ring;
each $R^{12}$ is independently H or unsubstituted $C_{1-8}$ alkyl;
each $R^{13}$ is independently H or unsubstituted $C_{1-8}$ alkyl;
each $R^{14}$ is independently OH or unsubstituted $C_{1-8}$ alkyl;
each $R^{15}$ is independently H, unsubstituted $C_{1-8}$ alkyl, unsubstituted $C_{3-8}$ cycloalkyl, unsubstituted heterocycle, unsubstituted $C_{6-10}$ aryl or unsubstituted $C_{3-8}$ cycloalkenyl;
each $R^{16}$ is independently H, unsubstituted $C_{1-8}$ alkyl, unsubstituted $C_{3-8}$ cycloalkyl, unsubstituted heterocycle, unsubstituted $C_{6-10}$ aryl or unsubstituted $C_{3-8}$ cycloalkenyl;
$R^{17}$ is H, unsubstituted $C_{1-8}$ alkyl, unsubstituted $C_{3-8}$ cycloalkyl, unsubstituted heterocycle, unsubstituted $C_{6-10}$ aryl or unsubstituted $C_{3-8}$ cycloalkenyl;
each $R^{18}$ is independently H, unsubstituted $C_{1-8}$ alkyl, —CH$_2$—(C$_{3-8}$ cycloalkyl), —CH$_2$—(C$_{3-8}$ cycloalkenyl) or benzyl;
each $R^{19}$ is independently H, unsubstituted $C_{1-8}$ alkyl, —CH$_2$—(C$_{3-8}$ cycloalkyl), —CH$_2$—(C$_{3-8}$ cycloalkenyl) or benzyl;
each $R^{20}$ is independently selected from the group consisting of halogen, —OH, —CN, amino, nitro, ether, thioether, unsubstituted $C_{3-8}$ cycloalkyl, unsubstituted $C_{1-6}$ aryl, unsubstituted heterocycle, ester, aldehyde, ketone, carboxylic acid, amide, sulfonamide, sulfonic acid, phosphonic acid and phosphoric acid;
each $R^{21}$, $R^{22}$, $R^{23}$ and $R^{24}$ is independently selected from the group consisting of halogen, —OH, —CN, amino, nitro, ether, thioether, unsubstituted $C_{1-8}$ alkyl, unsubstituted $C_{3-8}$ cycloalkyl, unsubstituted $C_{1-6}$ aryl, unsubstituted heterocycle, ester, aldehyde, ketone, carboxylic acid, amide, sulfonamide, sulfonic acid, phosphonic acid and phosphoric acid;
each $R^{25}$ is independently selected from the group consisting of halogen, hydroxyl, amino, ether, thioether, unsubstituted $C_{3-8}$ cycloalkyl, unsubstituted $C_{3-8}$ cycloalkenyl, unsubstituted $C_{1-6}$ aryl, unsubstituted heterocycle, carboxylic acid, amide, sulfonic acid, phosphonic acid and phosphoric acid;
m is 0 or 1;
n is 1, 2, 3, 4, 5, 6, 7 or 8;
each p is independently 1 or 2; and
q is 1, 2, 3, 4, 5 or 6;
or a tautomer thereof;
or pharmaceutically acceptable salt of any one of the foregoing; provided that:
(a) when m is 1, then $R^8$ is OR$^9$ or NR$^{10}$R$^{11}$;
and (b) when m is 0, then $R^5$ is not H;
thereby treating the disease or condition by activating FPR2.

2. The method of claim 1, wherein in the compound of Formula I, or pharmaceutically acceptable salt thereof:
each $R^1$, $R^2$, $R^4$ and $R^5$ is independently H, optionally substituted $C_{1-8}$ alkyl or halogen; wherein each said optional alkyl substituent is independently selected from one or more $R^{20}$;
$R^3$ is optionally substituted $C_{1-8}$ alkyl, halogen or —OR$^{17}$; wherein said optional alkyl substituent is selected from one or more $R^{20}$;
$R^6$ is H or optionally substituted $C_{1-8}$ alkyl, wherein said optional alkyl substituent is selected from one or more $R^{25}$;

R[7] is H or optionally substituted $C_{1-8}$ alkyl, wherein said optional alkyl substituent is selected from one or more R[25];

R[5] is selected from the group consisting of H, OR[9], NR[10]R[11], sulfonate, sulfonic acid, phosphonate, phosphonic acid, phosphoric acid and optionally substituted heterocycle, wherein said heterocycle is selected from the group consisting of tetrazole, imidazole, thiazole, oxazole, triazole, thiophene, pyrazole and pyrrole; and wherein said optional heterocycle substituent an optionally substituted $C_{1-8}$ alkyl, wherein said optional alkyl substituent is OH or halogen;

R[9] is H or optionally substituted $C_{1-8}$ alkyl, wherein said optional alkyl substituent is OH, halogen, —O$C_{1-8}$ alkyl or —(O$C_{1-3}$ alkylene)$_q$-O$C_{1-3}$ alkyl;

R[10] is H or unsubstituted $C_{1-8}$ alkyl; R[11] is H or unsubstituted $C_{1-8}$ alkyl;

R[17] is H or unsubstituted $C_{1-8}$ alkyl;

each R[18] is H or unsubstituted $C_{1-8}$ alkyl;

each R[19] is H or unsubstituted $C_{1-8}$ alkyl;

each R[20] is independently selected from the group consisting of halogen, —OH, —CN, amino, nitro, ether, thioether, unsubstituted $C_{3-8}$ cycloalkyl, unsubstituted $C_{1-6}$ aryl, unsubstituted heterocycle, ester, aldehyde, ketone, carboxylic acid, amide, sulfonamide, sulfonic acid, phosphonic acid and phosphoric acid;

each R[25] is independently selected from the group consisting of halogen, hydroxyl, amino, ether, thioether, unsubstituted $C_{3-8}$ cycloalkyl, unsubstituted $C_{3-8}$ cycloalkenyl, unsubstituted $C_{1-6}$ aryl, unsubstituted heterocycle, carboxylic acid and amide; and n is 1 or 2; or a tautomer thereof.

3. The method of claim 1, wherein in the compound of Formula I, or pharmaceutically acceptable salt thereof:
R[1] is H or halogen;
R[2] is H;
R[3] is $C_{1-3}$ haloalkyl, halogen or —OR[17];
R[4] is H;
R[5] is H or halogen;
R[6] is H or unsubstituted $C_{1-3}$ alkyl;
R[7] is H;
R[5] is selected from the group consisting of H, OR[9], NR[10]R[11], sulfonate, sulfonic acid, phosphonate, phosphonic acid, phosphoric acid and optionally substituted heterocycle, wherein said heterocycle is selected from the group consisting of tetrazole, imidazole, thiazole, oxazole, triazole, thiophene, pyrazole and pyrrole; and wherein said optional heterocycle substituent is an optionally substituted $C_{1-8}$ alkyl, wherein said optional alkyl substituent is OH or halogen;
R[9] is H or unsubstituted $C_{1-4}$ alkyl;
R[10] is H or unsubstituted $C_{1-3}$ alkyl;
R[11] is H or unsubstituted $C_{1-3}$ alkyl;
R[17] is unsubstituted $C_{1-3}$ alkyl;
each R[18] is H or unsubstituted $C_{1-3}$ alkyl;
each R[19] is H; m is 0 or 1; and
n is 1 or 2;
or a tautomer thereof.

4. The method of claim 3, wherein in the compound of Formula I, or pharmaceutically acceptable salt thereof:
R[8] is H, OR[9] or NR[10]R[11].

5. The method of claim 1, wherein in the compound of Formula I, or pharmaceutically acceptable salt thereof:
m is 1;
n is 1;
R[8] is OR[9], wherein R[9] is H or unsubstituted $C_{1-8}$ alkyl;
R[18] is H or unsubstituted $C_{1-8}$ alkyl; and
R[19] is H.

6. The method of claim 1, wherein in the compound of Formula I, or pharmaceutically acceptable salt thereof:
m is 1;
n is 2;
R[8] is NR[10]R[11], wherein R[10] is H or unsubstituted $C_{1-8}$ alkyl, and R[11] is H or optionally substituted $C_{1-8}$ alkyl;
each R[18] is H; and
each R[19] is H.

7. The method of claim 1 wherein in the compound of Formula I, or pharmaceutically acceptable salt thereof:
m is 1;
n is 2;
R[8] is OR[9], wherein R[9] is H or unsubstituted $C_{1-8}$ alkyl;
each R[18] is H; and
each R[19] is H.

8. The method of claim 1, wherein in the compound of Formula I, or pharmaceutically acceptable salt thereof:
m is 0;
n is 2;
R[8] is OR[9], wherein R[9] is H;
each R[18] is H; and
each R[19] is H.

9. A method of claim 1, wherein the compound of Formula I is selected from the group consisting of:

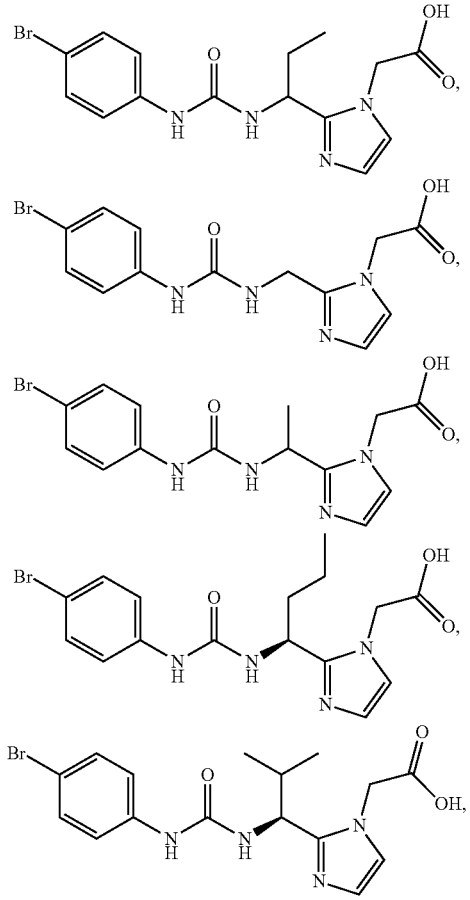

85
-continued
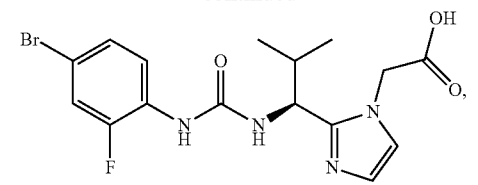
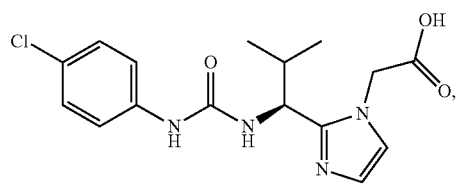
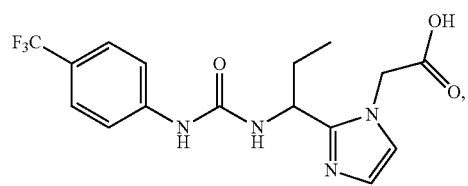
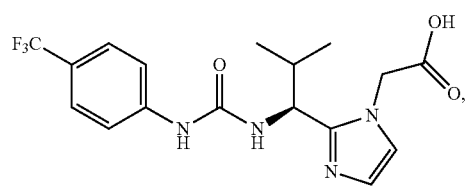
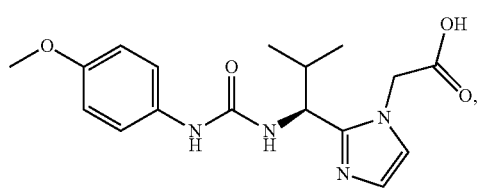
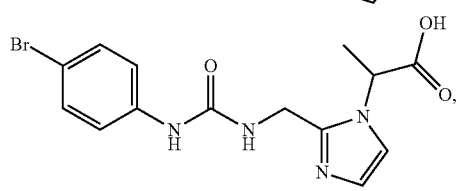
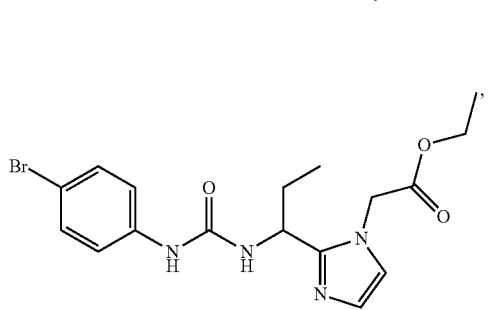
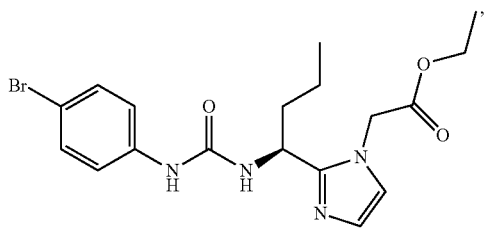
86
-continued
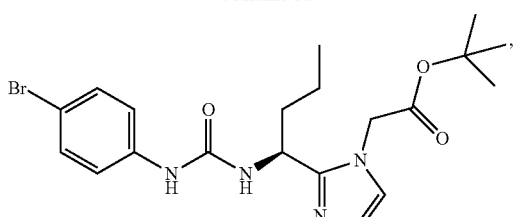
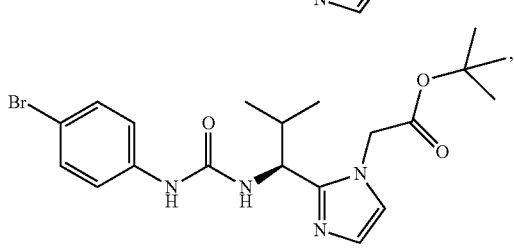
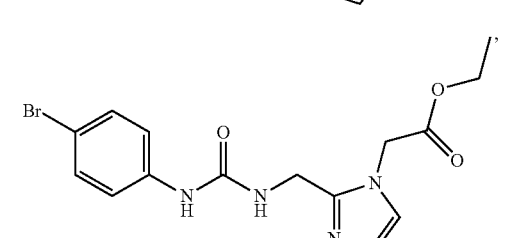
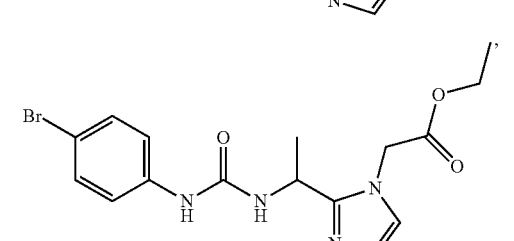
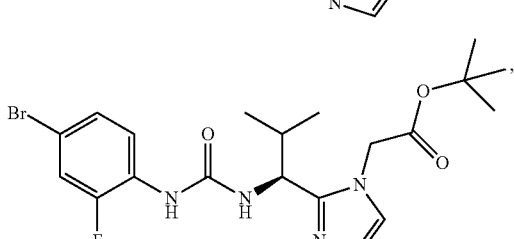
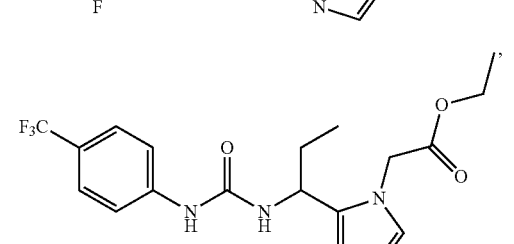
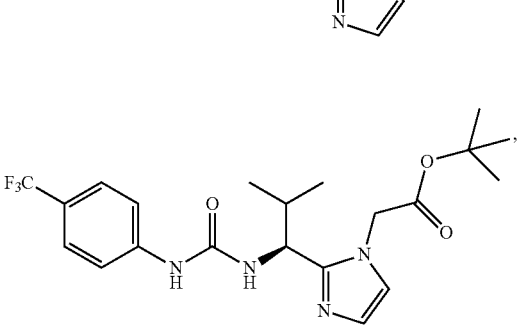

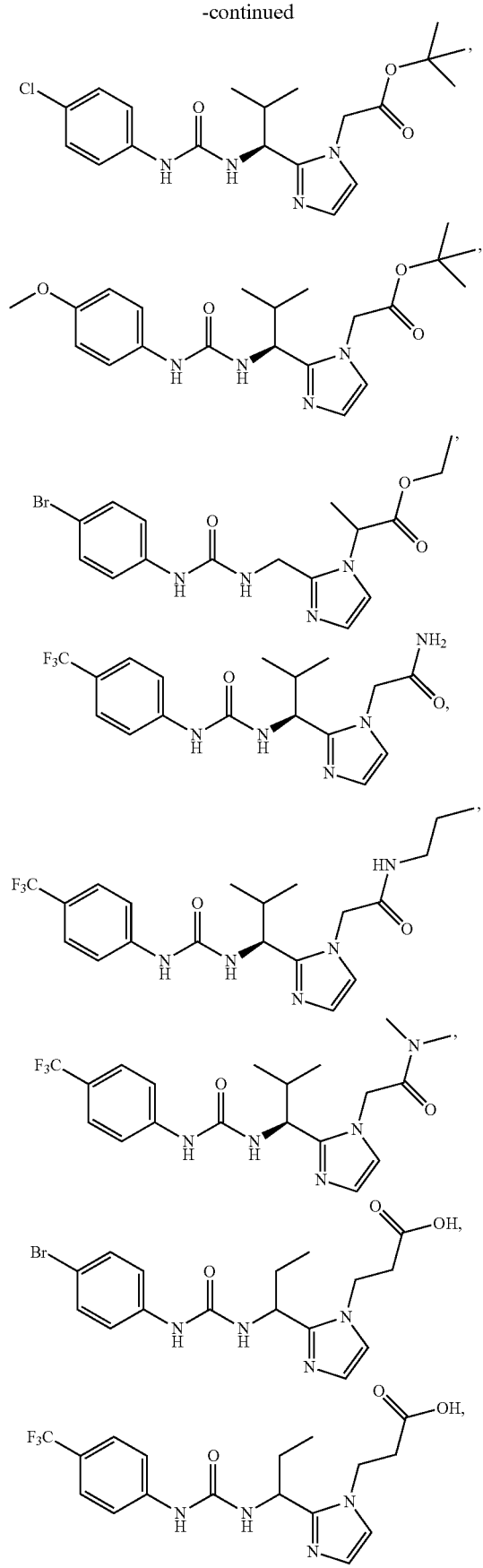

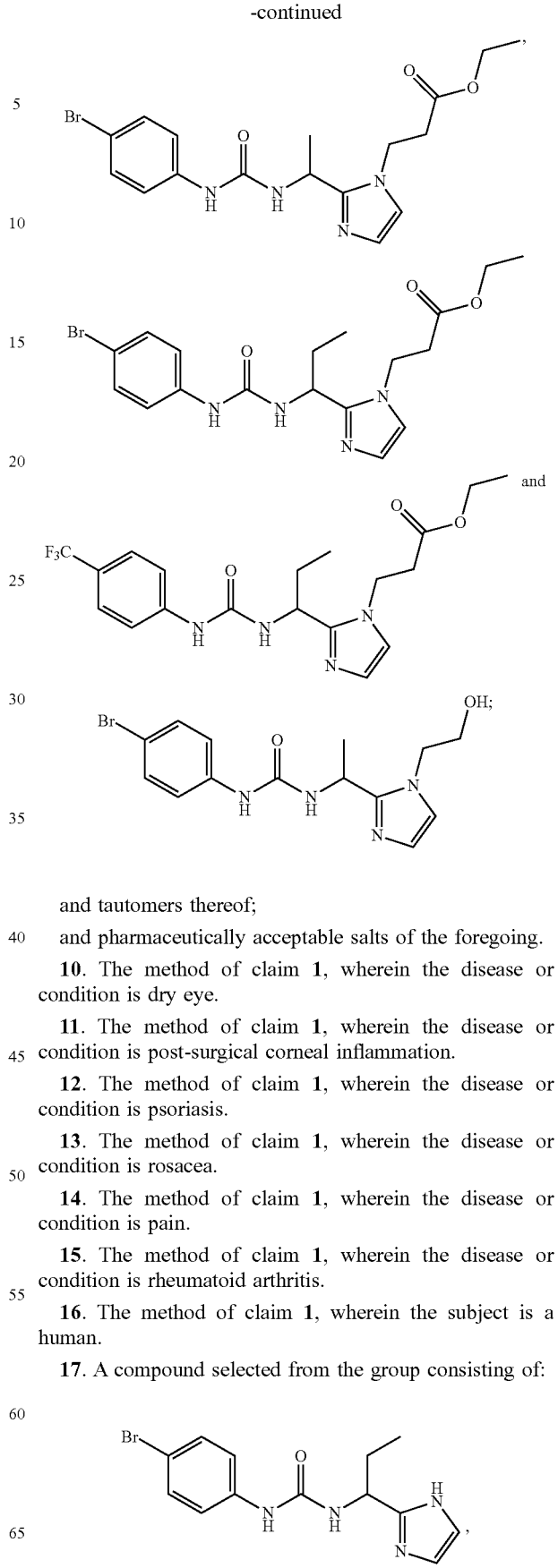

and tautomers thereof;

and pharmaceutically acceptable salts of the foregoing.

10. The method of claim 1, wherein the disease or condition is dry eye.

11. The method of claim 1, wherein the disease or condition is post-surgical corneal inflammation.

12. The method of claim 1, wherein the disease or condition is psoriasis.

13. The method of claim 1, wherein the disease or condition is rosacea.

14. The method of claim 1, wherein the disease or condition is pain.

15. The method of claim 1, wherein the disease or condition is rheumatoid arthritis.

16. The method of claim 1, wherein the subject is a human.

17. A compound selected from the group consisting of:

-continued

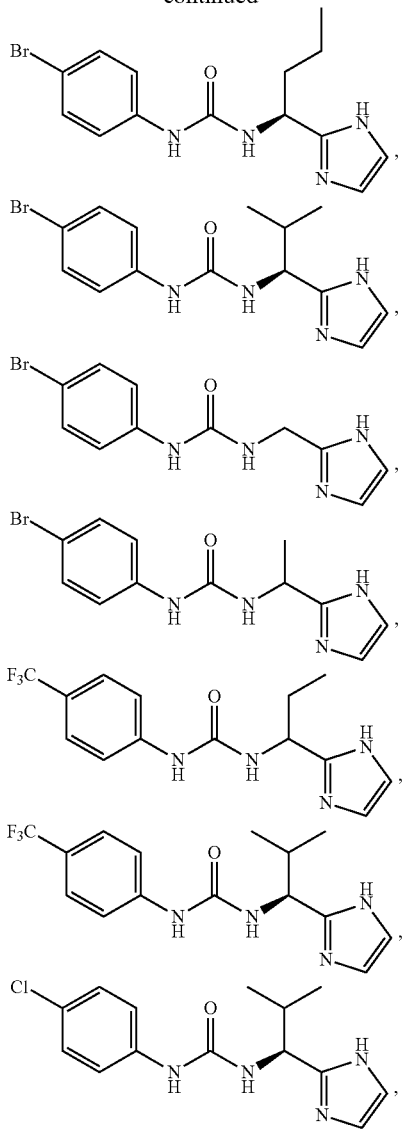

-continued

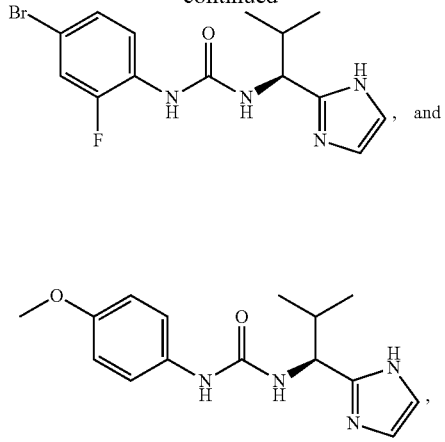

or a pharmaceutically acceptable salt thereof.

18. A method of treating a disease or condition mediated by FPR2 in a subject in need thereof, the method comprising administering a therapeutically effective amount of a compound of claim 17, or a pharmaceutically acceptable salt thereof, to the subject, thereby treating the disease or condition by activating FPR2.

19. The method of claim 18, wherein the disease or condition is dry eye.

20. The method of claim 18, wherein the disease or condition is post-surgical corneal inflammation.

21. The method of claim 18, wherein the disease or condition is psoriasis.

22. The method of claim 18, wherein the disease or condition is rosacea.

23. The method of claim 18, wherein the disease or condition is pain.

24. The method of claim 18, wherein the disease or condition is rheumatoid arthritis.

25. The method of claim 18, wherein the subject is a human.

* * * * *